United States Patent [19]

Inoue et al.

[11] Patent Number: 5,635,308
[45] Date of Patent: Jun. 3, 1997

[54] PHENYLANTHRACENE DERIVATIVE AND ORGANIC EL ELEMENT

[75] Inventors: Tetsushi Inoue; Kenji Nakaya, both of Chiba, Japan

[73] Assignee: TDK Corporation, Tokyo, Japan

[21] Appl. No.: 427,873

[22] Filed: Apr. 26, 1995

[30] Foreign Application Priority Data

Apr. 26, 1994 [JP] Japan .................... 6-110569

[51] Int. Cl.$^6$ .................... H05B 33/14; C07C 69/76
[52] U.S. Cl. .................... 428/690; 428/917; 313/503; 313/504; 313/506; 548/528
[58] Field of Search .................... 313/501–509; 428/690, 917; 548/528

[56] References Cited

FOREIGN PATENT DOCUMENTS

| 0403739 | 12/1990 | European Pat. Off. . |
| 3-162485 | 7/1991 | Japan . |
| 6-116552 | 4/1994 | Japan . |
| 6-206865 | 7/1994 | Japan . |

OTHER PUBLICATIONS

Appl. Phys. Lett., vol. 56, No. 9, pp. 799–801, Feb. 26, 1990, Chihaya Adachi, et al., "Blue Light–Emitting Organic Electrluminescent Devices".

J. Org. Chem., vol. 57, No. 6, 1992, No. 9, pp. 1883–1887, Hans–Dieter Becker, et al., "Molecular Conformations of 9,9'–Bianthryl, DI-9–Anthrylmethane, and Some Related Twisted Anthracene Derivatives".

*Primary Examiner*—Charles Nold
*Attorney, Agent, or Firm*—Oblon, Spivak, McClelland, Maier & Neustadt, P.C.

[57] ABSTRACT

Phenylanthracene derivatives of the formula: $A_1$—L—$A_2$ wherein $A_1$ and $A_2$ each are a monophenylanthryl or diphenylanthryl group and L is a valence bond or a divalent linkage group, typically arylene are novel opto-electronic functional materials. They are used as an organic compound layer of organic EL device, especially a light emitting layer for blue light emission.

12 Claims, 37 Drawing Sheets

PHENYLANTHRACENE DERIVATIVE AND ORGANIC EL ELEMENT

This invention generally relates to an organic electroluminescent (EL) element and more particularly, to an organic EL element of the type wherein an electric field is applied across an organic compound layer in a multilayer structure to emit light.

BACKGROUND OF THE INVENTION

Organic electroluminescent (EL) elements include a thin film containing a luminescent organic compound interleaved between a cathode and an anode. Electrons and holes are injected into the thin film where they are recombined to create excitons. Light is emitted by utilizing luminescence (phosphorescence or fluorescence) upon deactivation of excitons. The organic EL elements are characterized by plane light emission at a high luminance of about 100 to 100,000 cd/m$^2$ with a low voltage of about 10 volts and light emission in a spectrum from blue to red color by a simple choice of the type of fluorescent material.

The organic EL elements, however, are undesirably short in effective life, less durable during storage and less reliable because of the following factors.

(1) Physical changes of organic compounds: Growth of crystal grain domains renders the interface non-uniform, which causes deterioration of electric charge injecting ability, short-circuiting and dielectric breakdown of the element. Particularly when a low molecular weight compound having a molecular weight of less than 500 is used, grains develop and grow, substantially detracting from film quality. Even when the interface with indium tin oxide (ITO) is rough, significant development and growth of grains occur to lower luminous efficiency and allow current leakage, ceasing to emit light. Local dark spots are also formed.

(2) Oxidation and stripping of the cathode: Although metals having a low work function such as Na, Mg, and Al are used as the cathode in order to facilitate electron injection, these metals are reactive with oxygen and moisture in air. As a result, the cathode can be stripped from the organic compound layer, prohibiting electric charge injection. Particularly when a polymeric compound is applied as by spin coating, the residual solvent and decomposed products resulting from film formation promote oxidation reaction of the electrodes which can be stripped to create local dark spots.

(3) Low luminous efficiency and increased heat build-up: Since electric current is conducted across an organic compound, the organic compound is placed under an electric field of high strength and cannot help heating. The heat causes melting, crystallization or decomposition of the organic compound, leading to deterioration or failure of the element.

(4) Photo-chemical and electro-chemical changes of organic compound layers.

With respect to blue light-emitting devices, in particular, there are available few blue light-emitting substances which can provide for reliable stable devices. In general, blue light-emitting substances are highly crystalline. For example, diphenylanthracene has high crystallinity despite a high fluorescent quantum yield. Using this compound as a light emitting material fails to manufacture a reliable device having high luminance and high efficiency. See C. Adachi et al., Applied Phys. Lett., 56, 799 (1990).

SUMMARY OF THE INVENTION

Therefore, an object of the present invention is to provide a phenylanthracene derivative which is novel as an optoelectronic functional material and experiences minimal physical changes, photo-chemical changes and electro-chemical changes.

Another object of the present invention is to provide a novel and improved organic EL element using the phenylanthracene derivative, the element featuring high reliability, high luminous efficiency and an ability to emit a wide spectrum of light, especially blue light.

A further object of the present invention is to provide a high reliability, high luminance light emitting element having an organic thin film formed by evaporation of a high molecular weight compound, the element featuring minimized voltage rise, luminance drop, current leakage, and development or growth of local dark spots during operation of the element.

In a first aspect, the present invention provides a phenylanthracene derivative of the following general formula (1):

$$A_1-L-A_2 \qquad (1)$$

wherein each of $A_1$ and $A_2$, which may be identical or different, is a monophenylanthryl or diphenylanthryl group, and L is a valence bond or a divalent linkage group.

In one preferred embodiment, the phenylanthracene derivative is of the following formula (2):

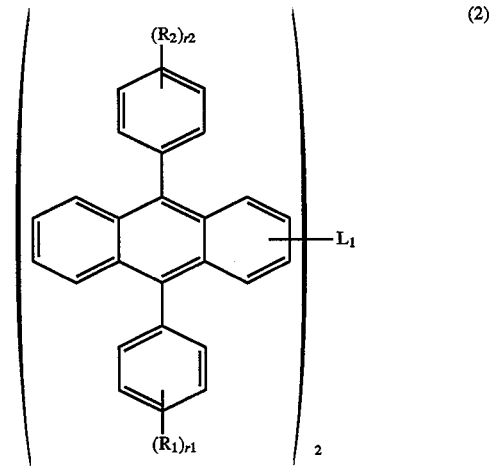

wherein each of $R_1$ and $R_2$, which may be identical or different, is selected from the group consisting of an alkyl, cycloalkyl, aryl, alkenyl, alkoxy, aryloxy, amino and heterocyclic group, each of r1 and r2 is 0 or an integer of 1 to 5, and $L_1$ is a valence bond or an arylene group which may have an intervening group in the form of an alkylene group, —O—, —S— or —NR— wherein R is an alkyl or aryl group. Where r1 is an integer of 2 to 5, the $R_1$ groups may be identical or different or the $R_1$ groups, taken together, may form a ring. Similarly, where r2 is an integer of 2 to 5, the $R_2$ groups may be identical or different or the $R_2$ groups, taken together, may form a ring.

In one preferred embodiment, the phenylanthracene derivative is of the following formula (3):

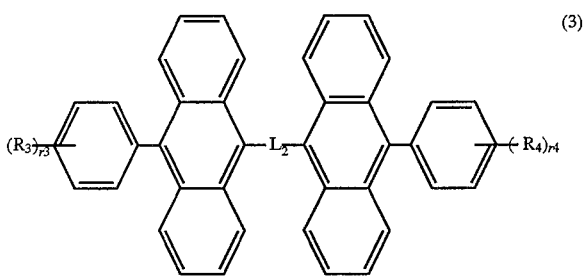

(3)

wherein each of $R_3$ and $R_4$, which may be identical or different, is selected from the group consisting of an alkyl, cycloalkyl, aryl, alkenyl, alkoxy, aryloxy, amino and heterocyclic group, each of r3 and r4 is 0 or an integer of 1 to 5, and $L_2$ is a valence bond or an arylene group which may have an intervening group in the form of an alkylene group, —O—, —S— or —NR— wherein R is an alkyl or aryl group. Where r3 is an integer of 2 to 5, the $R_3$ groups may be identical or different or the $R_3$ groups, taken together, may form a ring. Where r4 is an integer of 2 to 5, the $R_4$ groups may be identical or different or the $R_4$ groups, taken together, may form a ring.

In a second aspect, the present invention provides an organic electroluminescent (EL) element comprising at least one organic compound layer containing the phenylanthracene derivative defined above.

In one preferred embodiment, the organic compound layer containing the phenylanthracene derivative is a light emitting layer. The organic EL element may further include at least one hole injecting layer, at least one hole transporting layer, and at least one electron injecting and transporting layer. Alternatively, the organic EL element may further include at least one hole injecting layer, at least one hole transporting layer, at least one electron transporting layer, and at least one electron injecting layer.

In another preferred embodiment, the organic compound layer containing the phenylanthracene derivative is an electron injecting and transporting layer. In this case, the element further includes a light emitting layer.

In a further preferred embodiment, the organic EL element includes at least one light emitting layer which is a mix layer formed of a mixture of an electron injecting and transporting compound and a hole injecting and transporting compound. The phenylanthracene derivative is contained in the mix layer.

ADVANTAGES

Where an inventive compound of formula (1), preferably formula (2) or (3) is used in a light emitting layer, the organic EL element of the present invention can emit light at a luminance as high as about 10,000 cd/m² or more in a stable manner. The element insures stable driving with a current density of about 1,000 mA/cm². The element is resistant to heat and durable.

The inventive compound can be evaporated to deposit thin films in a stable amorphous state. Owing to good physical properties, the thin films are capable of uniformly emitting light with minimal variation. In the ambient air they remain stable over one year without crystallization. The compound can also be spin coated from a chloroform solution, forming stable amorphous thin films.

The organic EL element is capable of efficient light emission with a low driving voltage. Note that the element emits light with a maximum wavelength of about 400 nm to about 700 nm.

BRIEF DESCRIPTION OF THE DRAWINGS

The foregoing aspects and other features of the invention are explained in the following description, taken in connection with the accompanying drawings.

BEST MODE FOR CARRYING OUT THE INVENTION

Figure 1:
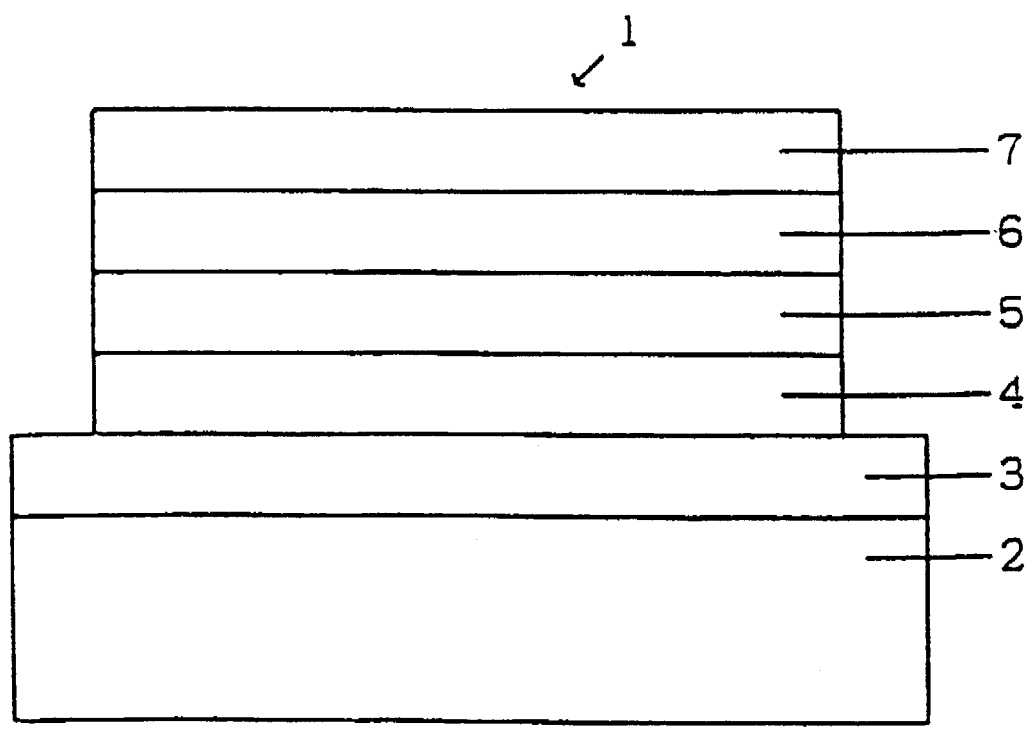
FIG. 1 is a side elevation of an exemplary organic EL element according to one embodiment of the invention.

The novel phenylanthracene derivatives of the present invention are of formula (1).

(1)

$A_1$ and $A_2$ each are a monophenylanthryl or diphenylanthryl group. $A_1$ and $A_2$ may be identical or different. The monophenylanthryl or diphenylanthryl group represented by $A_1$ and $A_2$ may be a substituted or unsubstituted one. Where substituted, exemplary substituents include alkyl, aryl, alkoxy, aryloxy, and amino groups, which may be further substituted. These substituents will be described later. Although the position of such substituents on the phenylanthryl group is not critical, the substituents are preferably positioned on the phenyl group bonded to the anthracene ring rather than on the anthracene ring. Preferably the phenyl group is bonded to the anthracene ring at its 9- and/or 10-position.

In formula (1), L is a valence bond or a divalent linkage group. The preferred divalent linkage group is an arylene group which may have an intervening alkylene group, as will be described later.

Preferred among the phenylanthracene derivatives of formula (1) are those of formulae (2) and (3).

First, formula (2) is described.

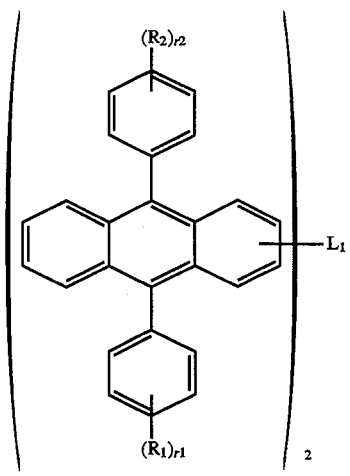

(2)

$R_1$ and $R_2$ are independently an alkyl, cycloalkyl, aryl, alkenyl, alkoxy, aryloxy, amino or heterocyclic group.

The alkyl group represented by $R_1$ and $R_2$ may be a straight or branched, substituted or unsubstituted alkyl group, preferably having 1 to 10 carbon atoms, more preferably 1 to 4 carbon atoms. Especially preferred are unsubstituted alkyl groups having 1 to 4 carbon atoms, for example, methyl, ethyl, n- and i-propyl, and n-, i-, s- and t-butyl groups. Examples of the cycloalkyl group represented by $R_1$ and $R_2$ include cyclohexyl and cyclopentyl groups. The aryl group represented by $R_1$ and $R_2$ preferably has 6 to 20 carbon atoms and may have a substituent such as phenyl and tolyl. Exemplary aryl groups are phenyl, o-, man- and p-tolyl, pyrenyl, naphthyl, anthryl, biphenyl, phenylanthryl, and tolylanthryl groups. The alkenyl group represented by $R_1$ and $R_2$ preferably has 6 to 50 carbon atoms in total and may be a substituted or unsubstituted one, preferably a substituted one wherein preferred substituents are aryl groups such as phenyl. Exemplary alkenyl groups are triphenylvinyl, tritolylvinyl and tribiphenylvinyl. The alkoxy group represented by $R_1$ and $R_2$ preferably has 1 to 6 carbon atoms in the alkyl moiety. Typical are methoxy and ethoxy groups. The alkoxy group may be a substituted one. Phenoxy is typical of the aryloxy group represented by $R_1$ and $R_2$. The amino group represented by $R_1$ and $R_2$ may be a substituted or unsubstituted one, preferably substituted one. Exemplary substituents are alkyl groups such as methyl and ethyl and aryl groups such as phenyl. Examples of the amino group include diethylamino, diphenylamino, and di(m-tolyl) amino groups. Examples of the heterocyclic group represented by $R_1$ and $R_2$ include bipyridyl, pyrimidyl, quinolyl, pyridyl, thienyl, furyl, and oxadiazoyl groups. They may have a substituent such as methyl and phenyl.

In formula (2), each of r1 and r2 is 0 or an integer of 1 to 5, preferably 0 or 1. Where each of r1 and r2 is an integer of 1 to 5, especially 1 or 2, each of $R_1$ and $R_2$ is preferably an alkyl, aryl, alkenyl, alkoxy, aryloxy or amino group.

$R_1$ and $R_2$ may be identical or different. Where more than one group is included as $R_1$ (that is, r1≧2), the $R_1$ groups may be identical or different or the $R_1$ groups, taken together, may form a ring such as a benzene ring. Likewise, where more than one group is included as $R_2$ (that is, r2≧2), the $R_2$ groups may be identical or different or the $R_2$ groups, taken together, may form a ring such as a benzene ring. Those derivatives wherein the $R_1$ or $R_2$ groups form a ring are also preferred.

$L_1$ is a valence bond or an arylene group. The arylene group represented by $L_1$ is preferably an unsubstituted one. Examples include ordinary arylene groups such as phenylene, biphenylene, and anthrylene while two or more directly bonded arylene groups are also included. Preferably $L_1$ is a valence bond, p-phenylene group, and 4,4'-biphenylene group.

The arylene group represented by $L_1$ may be a group having two arylene groups separated by an alkylene group, —O—, —S— or —NR—. R is an alkyl or aryl group. Exemplary alkyl groups are methyl and ethyl and an exemplary aryl group is phenyl. Preferably R is an aryl group which is typically phenyl as just mentioned while it may be $A_1$ or $A_2$ or phenyl having $A_1$ or $A_2$ substituted thereon. Preferred alkylene groups are methylene and ethylene groups.

Examples of the arylene group represented by $L_1$ are shown below.

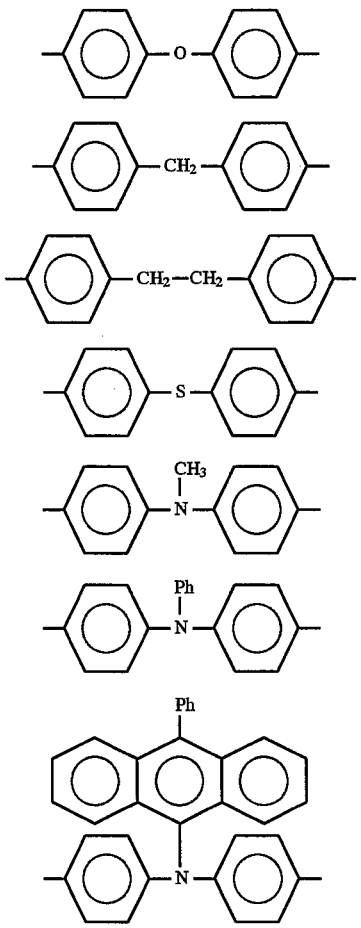

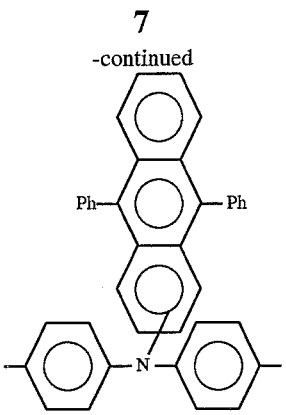

Next, formula (3) is described.

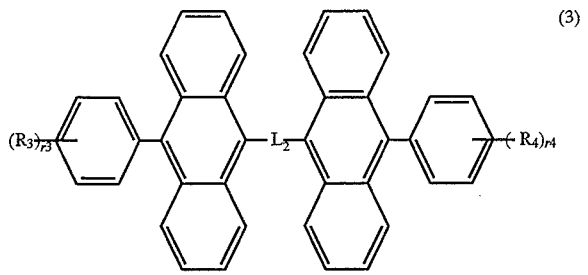
(3)

In formula (3), $R_3$ and $R_4$ are as defined for $R_1$ and $R_2$ in formula (2), r3 and r4 are as defined for r1 and r2 in formula (2), and $L_2$ is as defined for $L_1$ in formula (2). Their preferred examples are also the same.

Also in formula (3), $R_3$ and $R_4$ may be identical or different. Where more than one group is included as $R_3$ or $R_4$, the $R_3$ groups may be identical or different as well as the $R_4$ groups. Alternatively, the $R_3$ or $R_4$ groups, taken together, may form a ring such as a benzene ring.

Illustrative, non-limiting examples of the compounds formulae (2) and (3) are shown below. Examples are represented by general formulae (I) to (VII) wherein substituents $R_{11}$ to $R_{15}$, $R_{21}$ to $R_{25}$, $R_{31}$ to $R_{35}$, and $R_{41}$ to $R_{45}$ have the meaning and combination shown in Tables 1 to 7, respectively. Formulae (VIII), (IX), and (X) show specific structures.

I

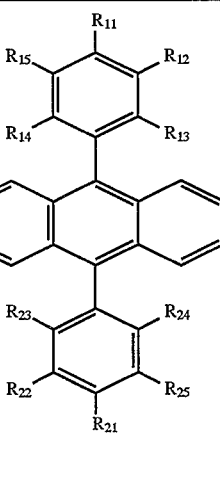

| Compound No. | $R_{11}$ | $R_{12}$ | $R_{13}$ | $R_{14}$ | $R_{15}$ | $R_{21}$ | $R_{22}$ | $R_{23}$ | $R_{24}$ | $R_{25}$ |
|---|---|---|---|---|---|---|---|---|---|---|
| I-1 | H | H | H | H | H | H | H | H | H | H |
| I-2 | $CH_3$ | H | H | H | H | $CH_3$ | H | H | H | H |
| I-3 | $t\text{-}C_4H_9$ | H | H | H | H | $t\text{-}C_4H_9$ | H | H | H | H |
| I-4 | $OCH_3$ | H | H | H | H | $OCH_3$ | H | H | H | H |
| I-5 | OPh | H | H | H | H | OPh | H | H | H | H |
| I-6 | $N(C_2H_5)_2$ | H | H | H | H | $N(C_2H_5)_2$ | H | H | H | H |
| I-7 | $N(Ph)_2$ | H | H | H | H | $N(Ph)_2$ | H | H | H | H |
| I-8 | Ph | H | H | H | H | Ph | H | H | H | H |
| I-9 | —⟨Ph⟩—$CH_3$ | H | H | H | H | —⟨Ph⟩—$CH_3$ | H | H | H | H |

-continued

| | | | | | | | | | | |
|---|---|---|---|---|---|---|---|---|---|---|
| I-10 | H | CH₃ | H | H | H | H | CH₃ | H | H | H |
| I-11 | H | CH₃ | H | CH₃ | H | H | CH₃ | H | CH₃ | H |
| I-12 | H | H | CH₃ | H | H | H | H | CH₃ | H | H |
| I-13 | H | CH₃ | H | H | CH₃ | H | CH₃ | H | H | CH₃ |
| I-14 | CH₃ | CH₃ | CH₃ | CH₃ | CH₃ | CH₃ | CH₃ | CH₃ | CH₃ | CH₃ |
| I-15 | t-C₄H₉ | H | H | H | H | H | H | H | H | H |
| I-16 | —C₆H₄—C₆H₅ | H | H | H | H | —C₆H₄—C₆H₅ | H | H | H | H |
| I-17 | H | Ph | H | H | H | H | Ph | H | H | H |
| I-18 | H | H | Ph | H | H | H | H | Ph | H | H |
| I-19 | C(Ph)=C(Ph)(Ph)– | H | H | H | H | C(Ph)=C(Ph)(Ph)– | H | H | H | H |
| I-20 | n-C₄H₉ | H | H | H | H | n-C₄H₉ | H | H | H | H |

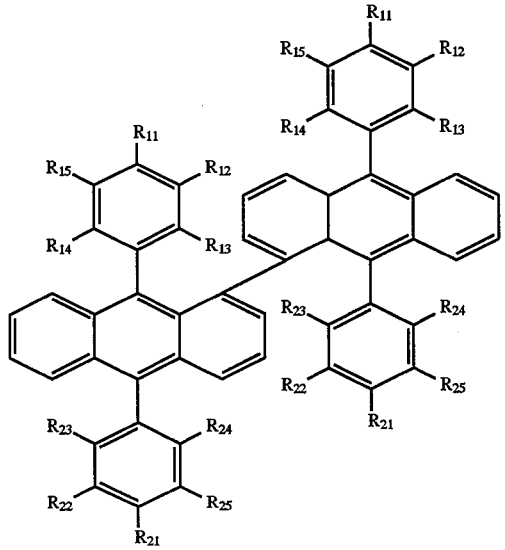

II

| Compound No. | $R_{11}$ | $R_{12}$ | $R_{13}$ | $R_{14}$ | $R_{15}$ | $R_{21}$ | $R_{22}$ | $R_{23}$ | $R_{24}$ | $R_{25}$ |
|---|---|---|---|---|---|---|---|---|---|---|
| II-1 | H | H | H | H | H | H | H | H | H | H |
| II-2 | CH₃ | H | H | H | H | CH₃ | H | H | H | H |
| II-3 | t-C₄H₉ | H | H | H | H | t-C₄H₉ | H | H | H | H |
| II-4 | OCH₃ | H | H | H | H | OCH₃ | H | H | H | H |
| II-5 | OPh | H | H | H | H | OPh | H | H | H | H |
| II-6 | N(C₂H₅)₂ | H | H | H | H | N(C₂H₅)₂ | H | H | H | H |
| II-7 | N(Ph)₂ | H | H | H | H | N(Ph)₂ | H | H | H | H |
| II-8 | Ph | H | H | H | H | Ph | H | H | H | H |
| II-9 | —C₆H₄—CH₃ | H | H | H | H | —C₆H₄—CH₃ | H | H | H | H |
| II-10 | H | CH₃ | H | H | H | H | CH₃ | H | H | H |
| II-11 | H | H | CH₃ | H | H | H | H | CH₃ | H | H |
| II-12 | H | H | CH₃ | CH₃ | H | H | H | CH₃ | CH₃ | H |
| II-13 | H | H | CH₃ | H | CH₃ | H | H | CH₃ | H | CH₃ |
| II-14 | CH₃ | CH₃ | CH₃ | CH₃ | CH₃ | CH₃ | CH₃ | CH₃ | CH₃ | CH₃ |
| II-15 | t-C₄H₉ | H | H | H | H | H | H | H | H | H |
| II-16 | —C₆H₄—C₆H₅ | H | H | H | H | —C₆H₄—C₆H₅ | H | H | H | H |

-continued

| | | | | | | | | | |
|---|---|---|---|---|---|---|---|---|---|
| II-17 | H | Ph | H | H | H | H | Ph | H | H |
| II-18 | H | H | Ph | H | H | H | H | Ph | H | H |

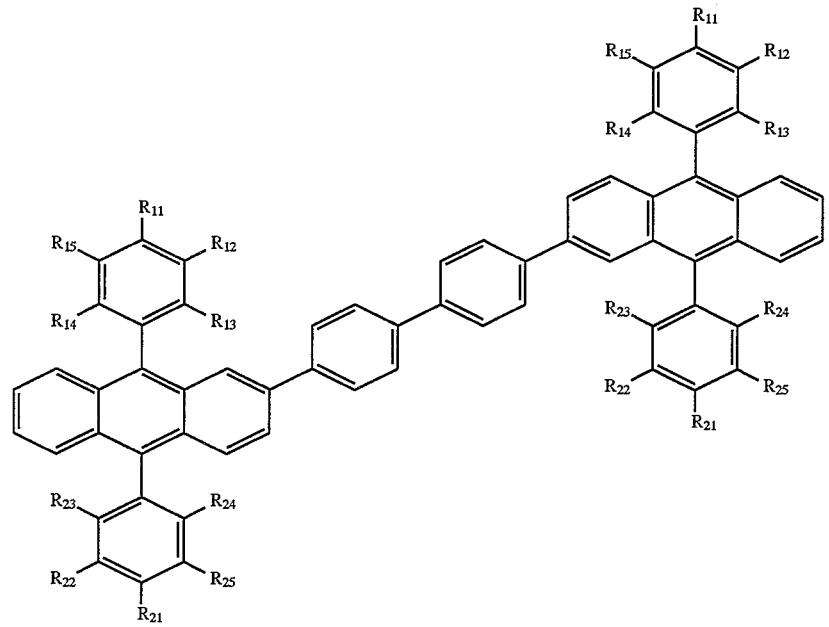

III

| Compound No. | $R_{11}$ | $R_{12}$ | $R_{13}$ | $R_{14}$ | $R_{15}$ | $R_{21}$ | $R_{22}$ | $R_{23}$ | $R_{24}$ | $R_{25}$ |
|---|---|---|---|---|---|---|---|---|---|---|
| III-1 | H | H | H | H | H | H | H | H | H | H |
| III-2 | $CH_3$ | H | H | H | H | $CH_3$ | H | H | H | H |
| III-3 | $t-C_4H_9$ | H | H | H | H | $t-C_4H_9$ | H | H | H | H |
| III-4 | $OCH_3$ | H | H | H | H | $OCH_3$ | H | H | H | H |
| III-5 | OPh | H | H | H | H | OPh | H | H | H | H |
| III-6 | $N(C_2H_5)_2$ | H | H | H | H | $N(C_2H_5)_2$ | H | H | H | H |
| III-7 | $N(Ph)_2$ | H | H | H | H | $N(Ph)_2$ | H | H | H | H |
| III-8 | Ph | H | H | H | H | Ph | H | H | H | H |
| III-9 | ―⟨⟩―$CH_3$ | H | H | H | H | ―⟨⟩―$CH_3$ | H | H | H | H |
| III-10 | H | $CH_3$ | H | H | H | H | $CH_3$ | H | H | H |
| III-11 | H | H | $CH_3$ | H | H | H | H | $CH_3$ | H | H |
| III-12 | H | H | $CH_3$ | $CH_3$ | H | H | H | $CH_3$ | $CH_3$ | H |
| III-13 | H | H | $CH_3$ | H | $CH_3$ | H | H | $CH_3$ | H | $CH_3$ |
| III-14 | $CH_3$ | $CH_3$ | $CH_3$ | $CH_3$ | $CH_3$ | $CH_3$ | $CH_3$ | $CH_3$ | $CH_3$ | $CH_3$ |
| III-15 | H | Ph | H | H | H | H | Ph | H | H | H |
| III-16 | H | H | Ph | H | H | H | H | Ph | H | H |
| III-17 | ―⟨⟩―⟨⟩ | H | H | H | H | ―⟨⟩―⟨⟩ | H | H | H | H |
| III-18 | $t-C_4H_9$ | H | H | H | H | H | H | H | H | H |
| III-19 | ―⟨cyclohexyl⟩ | H | H | H | H | ―⟨cyclohexyl⟩ | H | H | H | H |
| III-20 | N―N / ―⟨O⟩―Ph | H | H | H | H | N―N / ―⟨O⟩―Ph | H | H | H | H |
| III-21 | ―⟨S⟩―$CH_3$ | H | H | H | H | ―⟨S⟩―$CH_3$ | H | H | H | H |

-continued

| | | | | | | | | | | |
|---|---|---|---|---|---|---|---|---|---|---|
| III-22 | 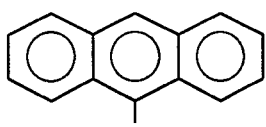 | H | H | H | H | 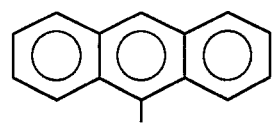 | H | H | H | H |

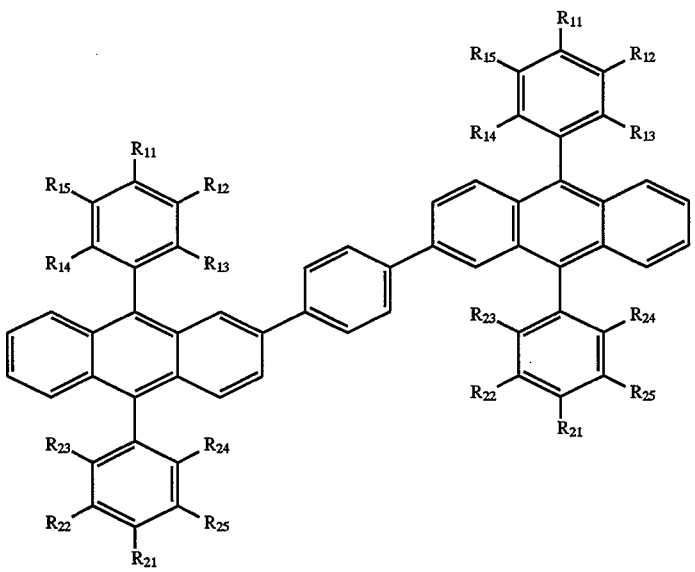

IV

| Compound No. | $R_{11}$ | $R_{12}$ | $R_{13}$ | $R_{14}$ | $R_{15}$ | $R_{21}$ | $R_{22}$ | $R_{23}$ | $R_{24}$ | $R_{25}$ |
|---|---|---|---|---|---|---|---|---|---|---|
| IV-1 | H | H | H | H | H | H | H | H | H | H |
| IV-2 | $CH_3$ | H | H | H | H | $CH_3$ | H | H | H | H |
| IV-3 | $t-C_4H_9$ | H | H | H | H | $t-C_4H_9$ | H | H | H | H |
| IV-4 | $OCH_3$ | H | H | H | H | $OCH_3$ | H | H | H | H |
| IV-5 | OPh | H | H | H | H | OPh | H | H | H | H |
| IV-6 | $N(C_2H_5)_2$ | H | H | H | H | $N(C_2H_5)_2$ | H | H | H | H |
| IV-7 | $N(Ph)_2$ | H | H | H | H | $N(Ph)_2$ | H | H | H | H |
| IV-8 | Ph | H | H | H | H | Ph | H | H | H | H |
| IV-9 | 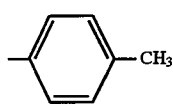 | H | H | H | H | 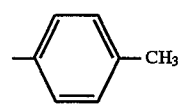 | H | H | H | H |
| IV-10 | H | $CH_3$ | H | H | H | H | $CH_3$ | H | H | H |
| IV-11 | H | H | $CH_3$ | H | H | H | H | $CH_3$ | H | H |
| IV-12 | H | H | $CH_3$ | $CH_3$ | H | H | H | $CH_3$ | $CH_3$ | H |
| IV-13 | H | H | $CH_3$ | H | $CH_3$ | H | H | $CH_3$ | H | $CH_3$ |
| IV-14 | $CH_3$ | $CH_3$ | $CH_3$ | $CH_3$ | $CH_3$ | $CH_3$ | $CH_3$ | $CH_3$ | $CH_3$ | $CH_3$ |
| IV-15 | H | Ph | H | H | H | H | Ph | H | H | H |
| IV-16 | H | H | Ph | H | H | H | H | Ph | H | H |
| IV-17 | [biphenyl] | H | H | H | H | [biphenyl] | H | H | H | H |
| IV-18 | $t-C_4H_9$ | H | H | H | H | H | H | H | H | H |
| IV-19 | [cyclohexyl] | H | H | H | H | [cyclohexyl] | H | H | H | H |
| IV-20 | [N=N oxadiazole-Ph] | H | H | H | H | [N=N oxadiazole-Ph] | H | H | H | H |

-continued

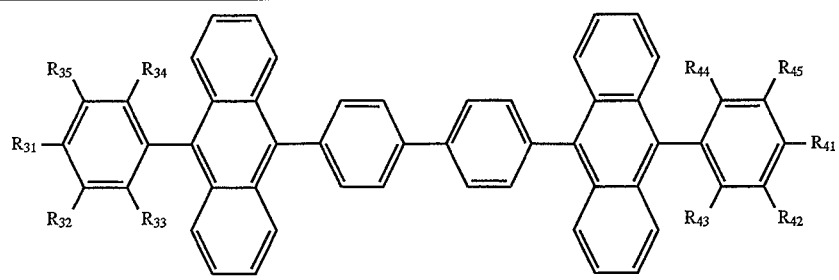

V

| Compound No. | $R_{11}$ | $R_{12}$ | $R_{13}$ | $R_{14}$ | $R_{15}$ | $R_{21}$ | $R_{22}$ | $R_{23}$ | $R_{24}$ | $R_{25}$ |
|---|---|---|---|---|---|---|---|---|---|---|
| V-1 | H | H | H | H | H | H | H | H | H | H |
| V-2 | CH₃ | H | H | H | H | CH₃ | H | H | H | H |
| V-3 | t-C₄H₉ | H | H | H | H | t-C₄H₉ | H | H | H | H |
| V-4 | OCH₃ | H | H | H | H | OCH₃ | H | H | H | H |
| V-5 | OPh | H | H | H | H | OPh | H | H | H | H |
| V-6 | N(C₂H₅)₂ | H | H | H | H | N(C₂H₅)₂ | H | H | H | H |
| V-7 | N(Ph)₂ | H | H | H | H | N(Ph)₂ | H | H | H | H |
| V-8 | Ph | H | H | H | H | Ph | H | H | H | H |
| V-9 | 4-tolyl | H | H | H | H | 4-tolyl | H | H | H | H |
| V-10 | H | CH₃ | H | H | H | H | CH₃ | H | H | H |
| V-11 | H | H | CH₃ | H | H | H | H | CH₃ | H | H |
| V-12 | H | H | CH₃ | CH₃ | H | H | H | CH₃ | CH₃ | H |
| V-13 | H | H | CH₃ | H | CH₃ | H | H | CH₃ | H | CH₃ |
| V-14 | CH₃ | CH₃ | CH₃ | CH₃ | CH₃ | CH₃ | CH₃ | CH₃ | CH₃ | CH₃ |
| V-15 | H | Ph | H | H | H | H | Ph | H | H | H |
| V-16 | H | H | Ph | H | H | H | H | Ph | H | H |
| V-17 | biphenyl | H | H | H | H | biphenyl | H | H | H | H |
| V-18 | t-C₄H₉ | H | H | H | H | t-C₄H₉ | H | H | H | H |
| V-19 | anthracenyl | H | H | H | H | anthracenyl | H | H | H | H |
| V-20 | naphthyl | H | H | H | H | naphthyl | H | H | H | H |
| V-21 | cyclohexyl | H | H | H | H | cyclohexyl | H | H | H | H |
| V-22 | oxadiazolyl-Ph | H | H | H | H | oxadiazolyl-Ph | H | H | H | H |
| V-23 | methylthienyl | H | H | H | H | methylthienyl | H | H | H | H |

-continued

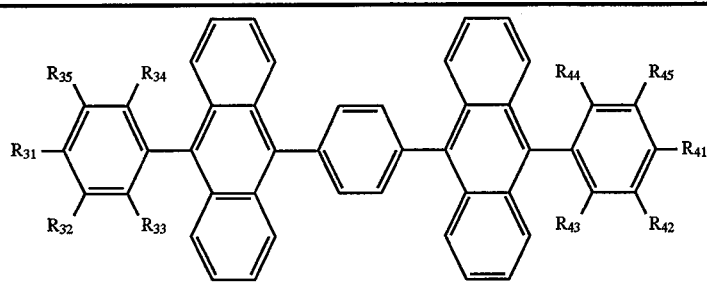
VI

| Compound No. | $R_{31}$ | $R_{32}$ | $R_{33}$ | $R_{34}$ | $R_{35}$ | $R_{41}$ | $R_{42}$ | $R_{43}$ | $R_{44}$ | $R_{45}$ |
|---|---|---|---|---|---|---|---|---|---|---|
| VI-1 | H | H | H | H | H | H | H | H | H | H |
| VI-2 | $CH_3$ | H | H | H | H | $CH_3$ | H | H | H | H |
| VI-3 | $t-C_4H_9$ | H | H | H | H | $t-C_4H_9$ | H | H | H | H |
| VI-4 | $OCH_3$ | H | H | H | H | $OCH_3$ | H | H | H | H |
| VI-5 | OPh | H | H | H | H | OPh | H | H | H | H |
| VI-6 | $N(C_2H_5)_2$ | H | H | H | H | $N(C_2H_5)_2$ | H | H | H | H |
| VI-7 | $N(Ph)_2$ | H | H | H | H | $N(Ph)_2$ | H | H | H | H |
| VI-8 | Ph | H | H | H | H | Ph | H | H | H | H |
| VI-9 | *p-tolyl* | H | H | H | H | *p-tolyl* | H | H | H | H |
| VI-10 | H | $CH_3$ | H | H | H | H | $CH_3$ | H | H | H |
| VI-11 | H | H | $CH_3$ | H | H | H | H | $CH_3$ | H | H |
| VI-12 | H | H | $CH_3$ | $CH_3$ | H | H | H | $CH_3$ | $CH_3$ | H |
| VI-13 | H | H | $CH_3$ | H | $CH_3$ | H | H | $CH_3$ | H | $CH_3$ |
| VI-14 | $CH_3$ | $CH_3$ | $CH_3$ | $CH_3$ | $CH_3$ | $CH_3$ | $CH_3$ | $CH_3$ | $CH_3$ | $CH_3$ |
| VI-15 | H | Ph | H | H | H | H | Ph | H | H | H |
| VI-16 | H | H | Ph | H | H | H | H | Ph | H | H |
| VI-17 | *biphenyl* | H | H | H | H | *biphenyl* | H | H | H | H |
| VI-18 | $t-C_4H_9$ | H | H | H | H | H | H | H | H | H |
| VI-19 | *anthryl* | H | H | H | H | *anthryl* | H | H | H | H |
| VI-20 | *naphthyl* | H | H | H | H | *naphthyl* | H | H | H | H |
| VI-21 | *10-Ph-anthryl* | H | H | H | H | H | H | H | H | H |
| VI-22 | *10-(p-tolyl)anthryl* | H | H | H | H | $CH_3$ | H | H | H | H |

-continued

| | | | | | | | | | | |
|---|---|---|---|---|---|---|---|---|---|---|
| VI-23 | cyclohexyl | H | H | H | H | cyclohexyl | H | H | H | H |
| VI-24 | N=N / \\ =/ \\-Ph / O | H | H | H | H | N=N / \\ =/ \\-Ph / O | H | H | H | H |

VII

Structure VII: 9,9'-bianthracene with aryl substituents bearing R31–R35 on one ring and R41–R45 on the other.

| Compound No. | R31 | R32 | R33 | R34 | R35 | R41 | R42 | R43 | R44 | R45 |
|---|---|---|---|---|---|---|---|---|---|---|
| VII-1 | H | H | H | H | H | H | H | H | H | H |
| VII-2 | CH₃ | H | H | H | H | CH₃ | H | H | H | H |
| VII-3 | t-C₄H₉ | H | H | H | H | t-C₄H₉ | H | H | H | H |
| VII-4 | OCH₃ | H | H | H | H | OCH₃ | H | H | H | H |
| VII-5 | OPh | H | H | H | H | OPh | H | H | H | H |
| VII-6 | N(C₂H₅)₂ | H | H | H | H | N(C₂H₅)₂ | H | H | H | H |
| VII-7 | N(Ph)₂ | H | H | H | H | N(Ph)₂ | H | H | H | H |
| VII-8 | Ph | H | H | H | H | Ph | H | H | H | H |
| VII-9 | p-tolyl | H | H | H | H | p-tolyl | H | H | H | H |
| VII-10 | H | H | CH₃ | CH₃ | H | H | H | CH₃ | CH₃ | H |
| VII-11 | H | H | CH₃ | H | CH₃ | H | H | CH₃ | H | CH₃ |
| VII-12 | H | CH₃ | H | H | H | H | CH₃ | H | H | H |
| VII-13 | H | H | CH₃ | H | H | H | H | CH₃ | H | H |
| VII-14 | CH₃ | CH₃ | CH₃ | CH₃ | CH₃ | CH₃ | CH₃ | CH₃ | CH₃ | CH₃ |
| VII-15 | H | Ph | H | H | H | H | Ph | H | H | H |
| VII-16 | H | H | Ph | H | H | H | H | Ph | H | H |
| VII-17 | biphenyl | H | H | H | H | biphenyl | H | H | H | H |
| VII-18 | t-C₄H₉ | H | H | H | H | H | H | H | H | H |
| VII-19 | 9-anthryl | H | H | H | H | 9-anthryl | H | H | H | H |
| VII-20 | cyclohexyl | H | H | H | H | cyclohexyl | H | H | H | H |
| VII-21 | N=N / \\ =/ \\-Ph / O | H | H | H | H | N=N / \\ =/ \\-Ph / O | H | H | H | H |
| VII-22 | 5-methylthien-2-yl | H | H | H | H | 5-methylthien-2-yl | H | H | H | H |

-continued
| | | | | | | | | | | |
|---|---|---|---|---|---|---|---|---|---|---|
| VII-23 | CH₃\C=C/Ph, Ph/ \Ph | H | H | H | H | CH₃\C=C/Ph, Ph/ \Ph | H | H | H | H |
| VII-24 | n-C₄H₉ | H | H | H | H | n-C₄H₉ | H | H | H | H |
| VII-25 | H | H | OCH₃ | H | H | H | H | OCH₃ | H | H |
| VII-26 | H | $R_{32}$ and $R_{33}$ condensed to form benzene ring | | H | H | H | $R_{42}$ and $R_{43}$ condensed to form benzene ring | | H | H |
| VII-27 | N(–C₆H₄–CH₃)₂ | H | H | H | H | N(–C₆H₄–CH₃)₂ | H | H | H | H |
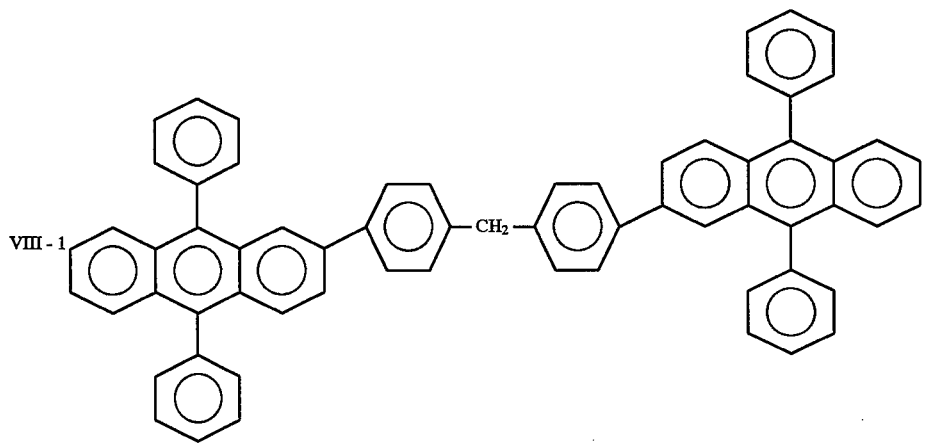
VIII-1
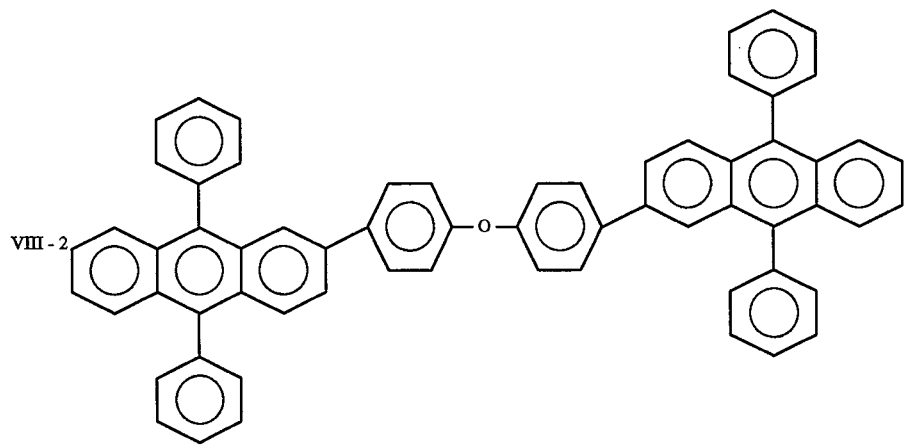
VIII-2

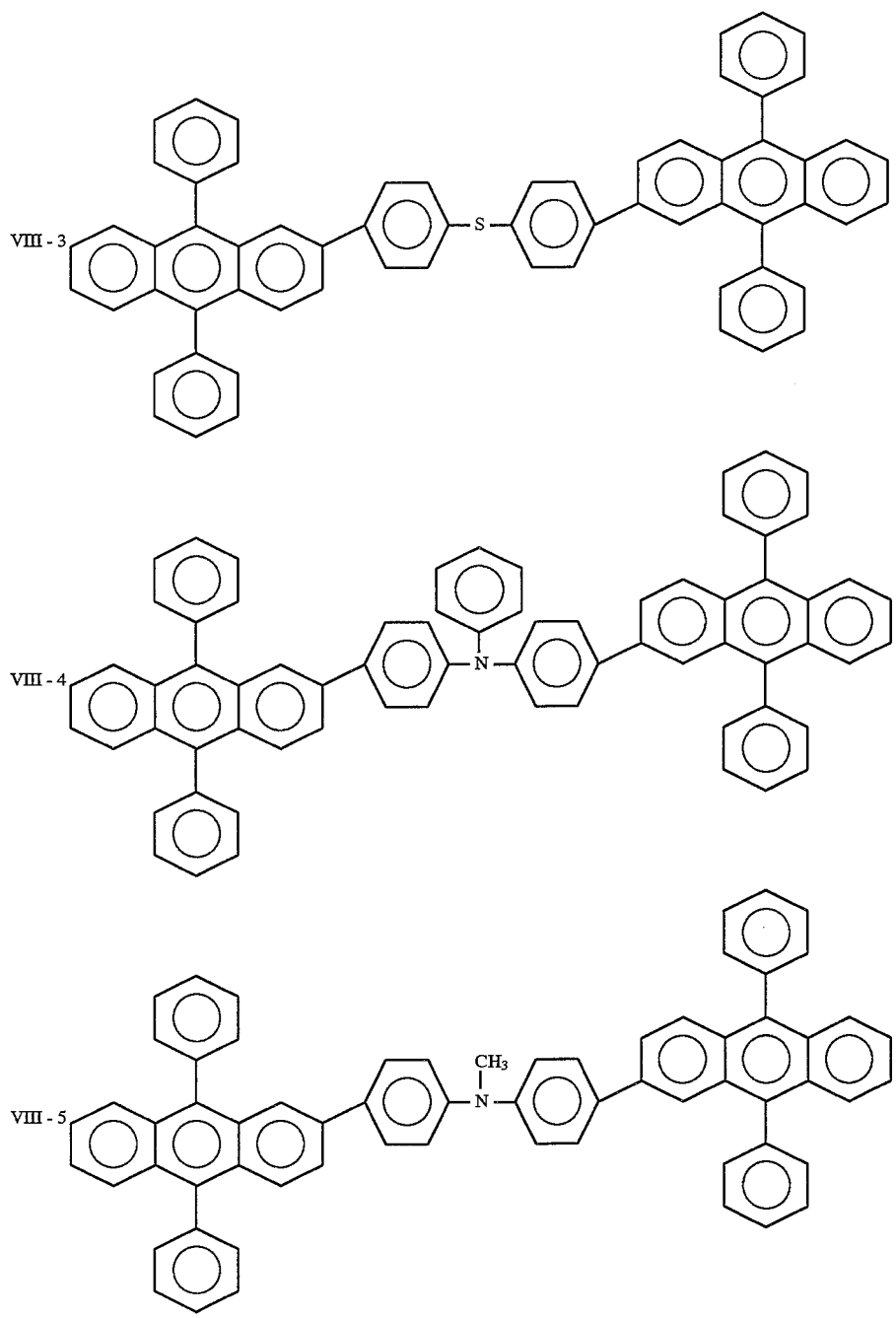

-continued
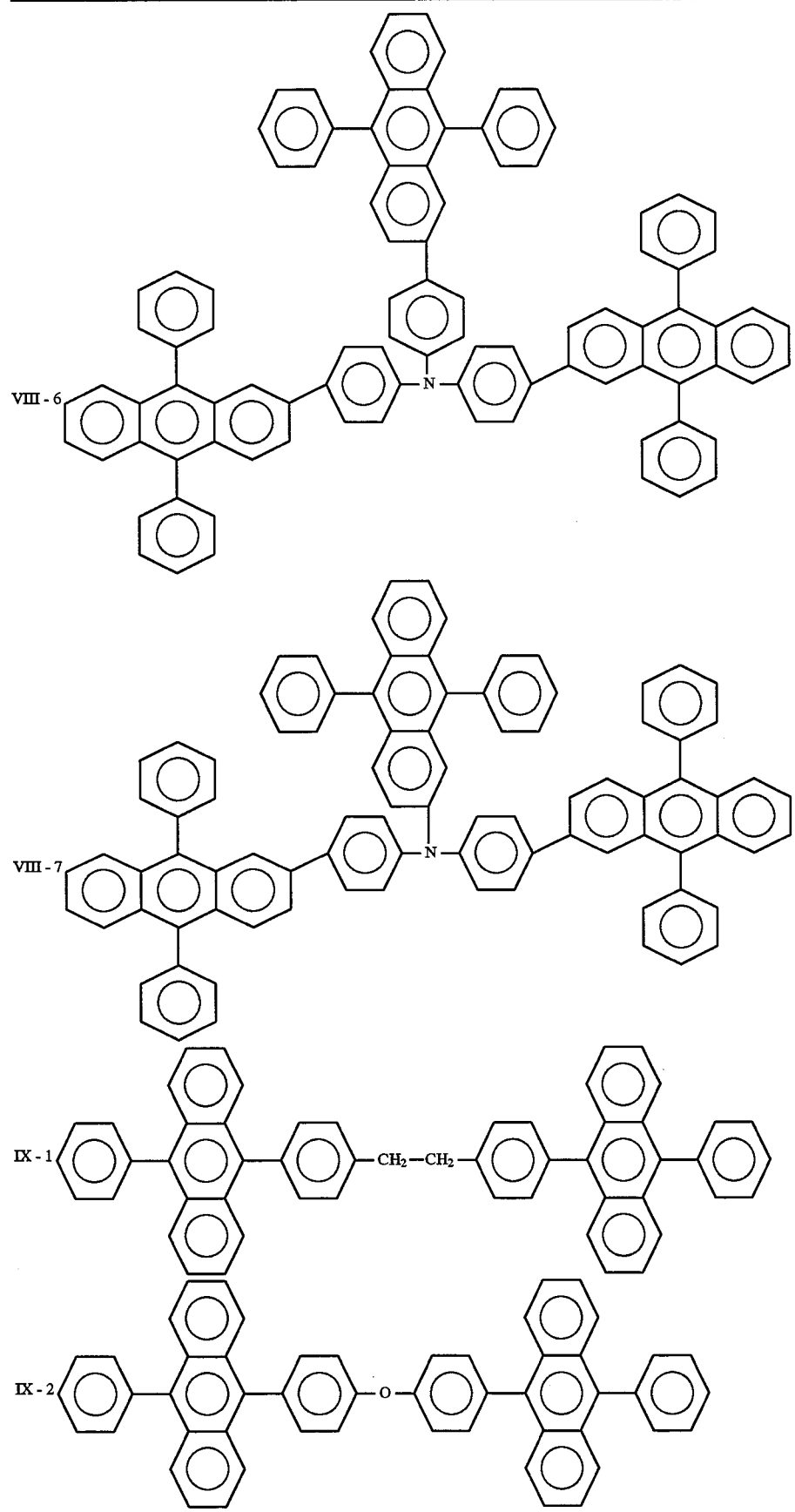

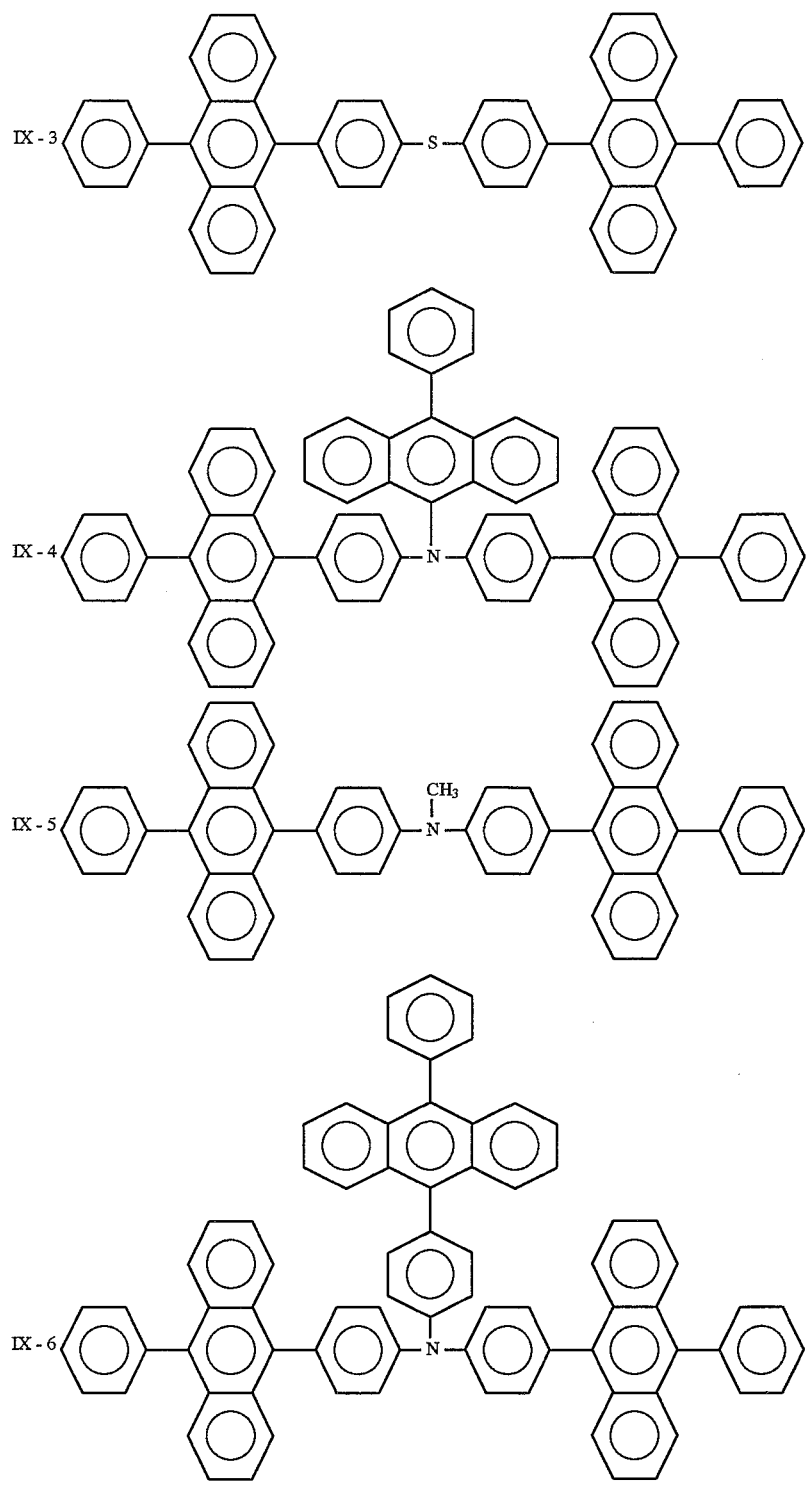

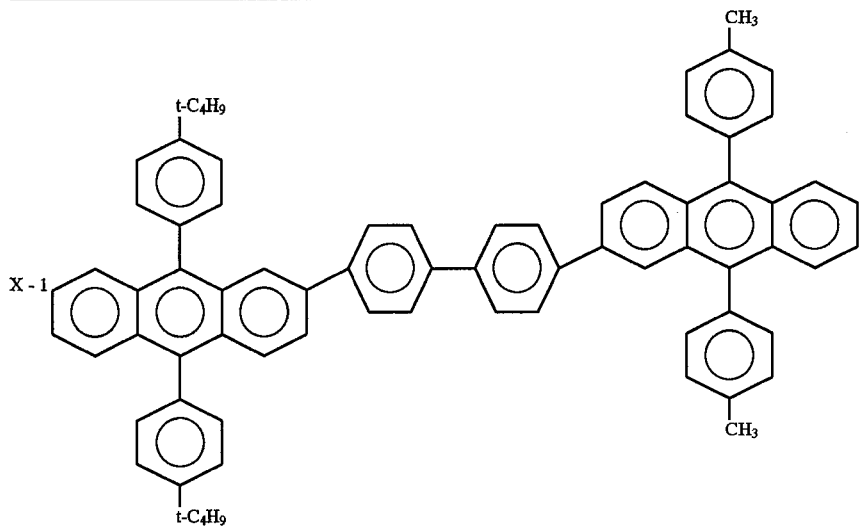

X-1

The phenylanthracene derivatives according to the present invention, which are sometimes referred to as inventive compounds, can be prepared by coupling a halogenated diphenylanthracene compound with Ni(cod)$_2$ wherein cod represents 1,5-cyclooctadiene, or cross-coupling a Grignard reagent of a dihalogenated aryl with a nickel complex such as NiCl$_2$(dppe) and NiCl$_2$(dppp) wherein dppe represents diphenylphosphinoethane and dppp represents diphenylphosphinopropane. Alternatively, the phenylanthracene derivatives are prepared by a cross-coupling process involving reacting anthraquinone, benzoquinone, phenylanthrone or bianthrone with a Grignard reagent of aryl or a lithiated aryl followed by reduction. These compounds can be identified by elemental analysis, mass analysis, infrared absorption spectroscopy (IR), nuclear magnetic resonance spectroscopy ($^1$H and $^{13}$C NMR), etc.

In general, the inventive compounds have a molecular weight of about 400 to about 2,000, preferably about 400 to about 1,000, a high melting point of about 200° to about 500° C., and a high glass transition temperature (Tg) of about 80° to about 250° C., preferably about 100° to 250° C., more preferably about 130° to 250° C., especially about 150° to 250° C. By conventional vacuum deposition or the like, they form a transparent, smooth film of quality which maintains a stable amorphous state even above room temperature and over a long period of time. The inventive compounds may be used alone or in admixture of two or more.

The organic EL element of the invention includes at least one organic compound layer. The organic compound layer or at least one of organic compound layers contains the inventive compound. One exemplary structure of the organic EL element according to the present invention is shown in FIG. 1. The EL element generally designated at 1 in FIG. 1 includes on a substrate 2, an anode 3, a hole injecting and transporting layer 4, a light emitting layer 5, an electron injecting and transporting layer 6, and a cathode 7 stacked in the described order from bottom to top.

The light emitting layer has multi-functions of injecting holes and electrons, transporting them, and recombining holes and electrons to create excitons. The hole injecting and transporting layer has functions of facilitating injection of holes from the anode, transporting them, and obstructing electron transportation. The electron injecting and transporting layer has functions of facilitating injection of electrons from the cathode, transporting them, and obstructing hole transportation. These two layers are effective for increasing the number of holes and electrons injected into the light emitting layer and confining holes and electrons therein for optimizing the recombination region to improve light emission efficiency. Therefore the hole and electron injecting and transporting layers are optionally provided by taking into account the magnitude of the respective functions of the compound used in the light emitting layer for electron injection and transportation and hole injection and transportation. For example, if the compound used in the light emitting layer has an enhanced hole or electron injecting and transporting function, the hole or electron injecting and transporting layer may be omitted because the light emitting layer itself can also serve as a hole or electron injecting and transporting layer. In some cases, both the hole and electron injecting and transporting layers may be omitted. Each of the hole and electron injecting and transporting layers may consist of two sublayers, one sublayer having an injecting function and another sublayer having a transporting function.

The inventive compound is preferably used in a light emitting layer because it is relatively neutral although it is also applicable to either a hole injecting and transporting layer or an electron injecting and transporting layer.

A freedom of design of the recombination/light emitting region is available by controlling the film thickness in consideration of the carrier mobility and carrier density (which is dependent on ionization potential and electron affinity) of the light emitting layer, hole injecting and transporting layer, and electron injecting and transporting layer to be combined. This enables free design of luminous color, control of the luminance and spectrum of light emission by the interference of the electrodes, and control of the space distribution of light emission.

Described below is the embodiment wherein the inventive compounds are used in the light emitting layer. The light emitting layer may additionally contain another luminescent material. The luminescent material may be selected from compounds as disclosed in JP-A 264692/1988, for example, quinacridone, rubrene, and styryl series dyes alone or in admixture. Such a luminescent material is preferably contained in the light emitting layer in an amount of less than 10 mol % of the inventive compound. By adding a selected luminescent material, the light emitted by the layer can be shifted to a longer wavelength side.

The light emitting layer may further contain a singlet oxygen quencher. Exemplary quenchers include nickel complexes, rubrene, diphenylisobenzofuran, and tertiary amines. Such a quencher is preferably present in an amount of less than 10 mol % of the inventive compound.

In the preferred embodiment wherein the inventive compounds are used in the light emitting layer, any of various organic compounds used in conventional organic EL elements, for example, the organic compounds described in JP-A 295695/1988, 191694/1990, and 000792/1991 may be used in the hole injecting and transporting layer and electron injecting and transporting layer. For example, in the hole injecting and transporting layer, any of aromatic tertiary amines, hydrazone derivatives, carbazole derivatives, triazole derivatives, and imidazole derivatives may be used. For the electron injecting and transporting layer, organic metal complex derivatives such as aluminum quinolinol, oxadiazole derivatives, pyridine derivatives, pyrimidine derivatives, quinoline derivatives, quinoxaline derivatives, diphenylquinone derivatives, perylene derivatives, and fluorene derivatives may be used.

Where the hole injecting and transporting layer is formed as comprising a hole injecting layer and a hole transporting layer, two or more compounds are selected in a proper combination from the compounds commonly used in hole injecting and transporting layers. In this regard, it is preferred to laminate layers such that a layer of a compound having a lower ionization potential may be disposed adjacent to the anode (ITO etc.). It is also preferred to use a compound having good thin film forming ability at the anode surface. This order of lamination also applies where a plurality of hole injecting and transporting layers are provided. Such an order of lamination is effective for lowering drive voltage and preventing current leakage and development and growth of local dark spots. Since evaporation is utilized in manufacturing elements, thin films of about 1 to 10 nm thick can be formed uniform and pinhole-free, which restrains any change in color tone of light emission and a drop of efficiency by re-absorption even if a compound having a low ionization potential and absorption in the visible range is used in the hole injecting layer.

Where the electron injecting and transporting layer is formed as comprising an electron injecting layer and an electron transporting layer, two or more compounds are selected in a proper combination from the compounds commonly used in electron injecting and transporting layers. In this regard, it is preferred to laminate layers such that a layer of a compound having a greater electron affinity may be disposed adjacent to the cathode. This order of lamination also applies where a plurality of electron injecting and transporting layers are provided.

In the practice of the invention, it is preferred that the light emitting layer be a mix layer containing a mixture of a hole injecting and transporting compound and an electron injecting and transporting compound. The inventive compound is contained in the mix layer. Since the inventive compound is generally contained as a fluorescent material, in one embodiment wherein the inventive compound is an electron injecting and transporting compound, it is preferred to further add a hole injecting and transporting compound. In another embodiment wherein the inventive compound is a hole injecting and transporting compound, it is preferred to further add an electron injecting and transporting compound. In the mix layer, the electron injecting and transporting compound and hole injecting and transporting compound are preferably mixed such that the weight ratio of electron injecting and transporting compound to hole injecting and transporting compound may range from about 60:40 to about 40:60, especially about 50:50.

For this mixture, an electron injecting and transporting compound may be selected from the above-mentioned electron injecting and transporting compounds and a hole injecting and transporting compound may be selected from the above-mentioned hole injecting and transporting compounds. If desired, any of the inventive compounds may be selected. In the mix layer, each of the electron injecting and transporting compound and hole injecting and transporting compound may be used alone or in admixture of two or more. The mix layer may be doped with the inventive compound or another fluorescent material for enhancing luminous intensity.

Alternatively, a mix layer of an electron injecting and transporting compound and a hole injecting and transporting compound both other than the above-mentioned ones may be doped with the inventive compound.

With such a mix layer incorporated, an EL element is improved in stability.

It is also preferable to use the inventive compound in the electron injecting and transporting layer. In this embodiment, the fluorescent material used in the light emitting layer may be selected from those capable of fluorescence at an equal or longer wavelength as compared with the inventive compound, for example, from those fluorescent materials which can be used in combination with the inventive compound in the light emitting layer. In this embodiment, the inventive compound may be further used in the light emitting layer. Alternatively, the inventive compound may be further used in the light emitting layer which also serves as an electron injecting and transporting layer.

It is also preferable to use the inventive compound in the hole injecting and transporting layer. In this embodiment, the fluorescent material used in the light emitting layer may be selected from those capable of fluorescence at a longer wavelength as compared with the inventive compound, for example, from those fluorescent materials which can be used in combination with the inventive compound in the light emitting layer. In this embodiment, the inventive compound may be further used in the light emitting layer.

Where a fluorescent material (other than the inventive compound) is used mainly in the light emitting layer in these embodiments, the inventive compound may be added and combined as an additional fluorescent material in an amount of less than 10 mol %.

The thicknesses of the light emitting layer, hole injecting and transporting layer, and electron injecting and transporting layer are not critical and varies with a particular formation technique. Usually a single layer is about 5 to 1,000 nm thick, especially about 8 to 200 nm thick.

The thicknesses of the hole injecting and transporting layer and electron injecting and transporting layer are equal to or range from $\frac{1}{10}$ to 10 times the thickness of the light emitting layer although they depend on the design of a recombination/light emitting region. When the electron or hole injecting and transporting layer is divided into an injecting layer and a transporting layer, preferably the injecting layer is at least 1 nm thick and the transporting layer is at least 20 nm thick. The upper limit of thickness is about 100 nm for the injecting layer and about 1,000 nm for the transporting layer.

In the practice of the invention, the cathode is preferably made of a material having a low work function, for example, Li, Na, Mg, Al, Ag, In and alloys containing at least one of these metals. The cathode should preferably be of fine grains, especially amorphous. The cathode is preferably about 10 to 1,000 nm thick. In order that the EL element produce plane light emission, at least one of the electrodes should be transparent or translucent. Since the material of the cathode is limited as mentioned just above, it is preferred to select the material and thickness of the anode so as to provide a transmittance of at least 80% to the emitted radiation. For example, the anode is preferably made of indium tin oxide (ITO), $SnO_2$, Ni, Au, Pt, Pd, and doped polypyrrole. The anode preferably has a thickness of about 10 to 500 nm. In order that the element be more reliable, the drive voltage should be low. To this end, ITO having 10 to 30Ω/cm² or less than 10Ω/cm² (commonly about 5 to 10Ω/cm²) is preferred, for example.

The substrate may be made of any desired material although a transparent or translucent material such as glass and resins is used in the illustrated embodiment wherein light exits from the substrate side. The substrate may be provided with a color filter layer or dielectric reflecting film for controlling emission light color. Where the substrate is made of an opaque material, the layer stacking order may be reversed from that shown in FIG. 1.

Next, it is described how to prepare the EL element using the phenylanthracene derivative of the present invention. The cathode and anode are preferably formed by gas phase deposition techniques such as vacuum evaporation and sputtering. The light emitting layer and hole and electron injecting and transporting layers are preferably formed by vacuum evaporation because homogeneous thin films are available. By utilizing vacuum evaporation, there is obtained a homogeneous thin film which is amorphous or has a grain size of less than 0.1 µm and typically upward of 0.01 µm. If the grain size is more than 0.1 µm, uneven light emission takes place and the drive voltage of the element must be increased with a substantial lowering of electric charge injection efficiency.

The conditions for vacuum evaporation are not critical although a vacuum of $10^{-5}$ Torr or lower and an evaporation rate of about 0.1 to 1 nm/sec. are preferred. It is preferred to successively form layers in vacuum because the successive formation in vacuum can avoid adsorption of impurities at the interface between the layers, thus ensuring higher quality and a lower drive voltage.

In the embodiment wherein the respective layers are formed by vacuum evaporation, where it is desired for a single layer to contain two or more compounds, boats having the compounds received therein are individually temperature controlled to achieve co-deposition while monitoring the film thickness by means of a quartz oscillator film thickness gage.

The EL element of the invention is generally of the DC drive type while it can be of the AC or pulse drive type. The applied voltage is generally about 2 to 20 volts.

EXAMPLE

Examples of the present invention are given below by way of illustration and not by way of limitation. DSC is differential scanning calorimetry, mp is a melting point, Tg is a glass transition temperature, and THF is tetrahydrofuran.

Example 1

Synthesis of compound I-1

In a nitrogen atmosphere, 0.37 g (1.5 mmol) of bis(1,5-cyclooctadiene) nickel Ni(cod)$_2$, 0.20 g (1.50 mmol) of 2,2'-bipyridine, and 0.20 ml of 1,5-cyclooctadiene were mixed with 20 ml of N,N-dimethylformamide. 1.00 g (3.00 mmol) of 2-chloro-9,10-diphenylanthracene was added to the mixture, which was stirred for 24 hours at 60° C. The reaction solution was poured into 1N aqueous hydrochloric acid, from which the product was extracted with toluene and chloroform, washed with water and then dried over magnesium sulfate. The product was precipitated from acetone again, recrystallized three times from chloroform, and purified through a silica column using toluene as the extracting solvent, yielding 0.53 g of a yellowish white solid. This yellowish white solid, 0.5 g, was purified through sublimation, yielding 0.23 g of a yellowish white solid having blue fluorescence.

Elemental analysis

|  | C | H |
|---|---|---|
| Calcd. (%) | 94.80 | 5.20 |
| Found (%) | 94.96 | 4.90 |

Mass analysis: m/e 658 (M⁺)

Figure 2:
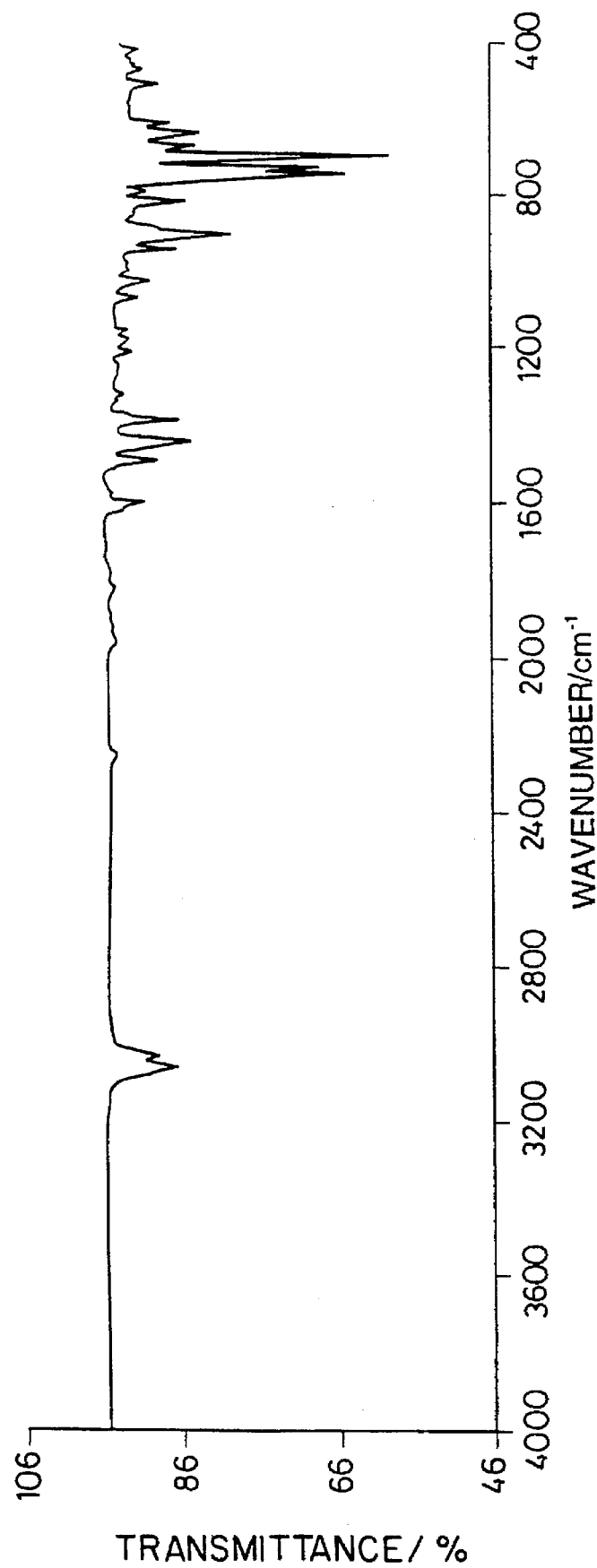
FIGS. 2 and 3 are graphs showing IR and NMR spectra of compound I-1 in Example 1, respectively.

IR absorption spectrum: FIG. 2

Figure 3:
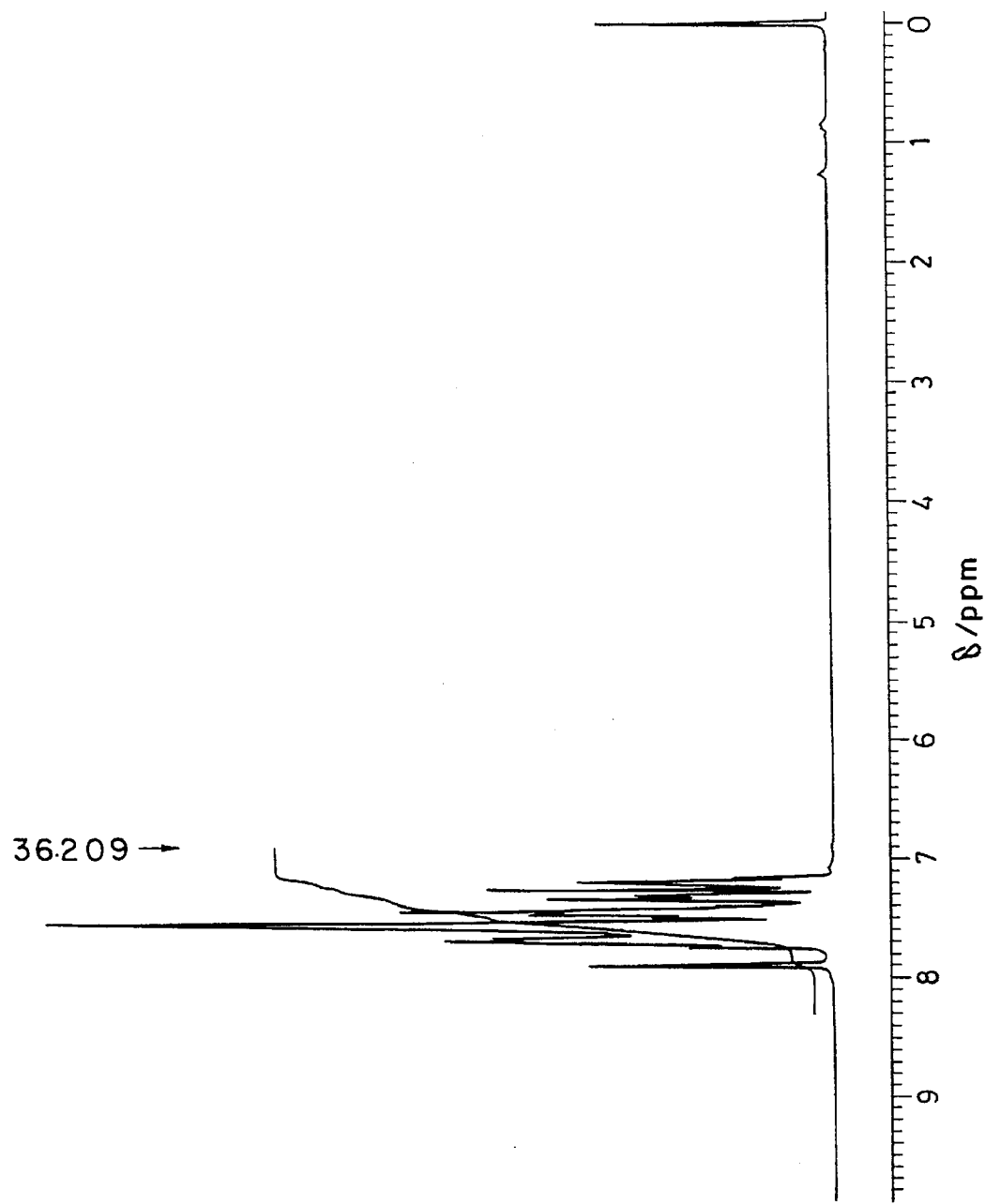

NMR spectrum: FIG. 3 DSC: mp 450° C., Tg 181° C.

Example 2

Synthesis of compound II-1

In a nitrogen atmosphere, 0.37 g (1.5 mmol) of bis(1,5-cyclooctadiene) nickel Ni(cod)$_2$, 0.20 g (1.50 mmol) of 2,2'-bipyridine, and 0.20 ml of 1,5-cyclooctadiene were mixed with 20 ml of N,N-dimethylformamide. 1.00 g (3.00 mmol) of 1-chloro-9,10-diphenylanthracene was added to the mixture, which was stirred for 24 hours at 60° C. The reaction solution was poured into 1N aqueous hydrochloric acid, from which the product was extracted with toluene and chloroform, washed with water and then dried over magnesium sulfate. The product was precipitated from acetone again, recrystallized three times from chloroform, and purified through a silica column using toluene as the extracting solvent, yielding 0.20 g of a yellowish white solid.

Elemental analysis

|  | C | H |
|---|---|---|
| Calcd. (%) | 94.80 | 5.20 |
| Found (%) | 94.60 | 4.97 |

Mass analysis: m/e 658 (M⁺)

Figure 4:
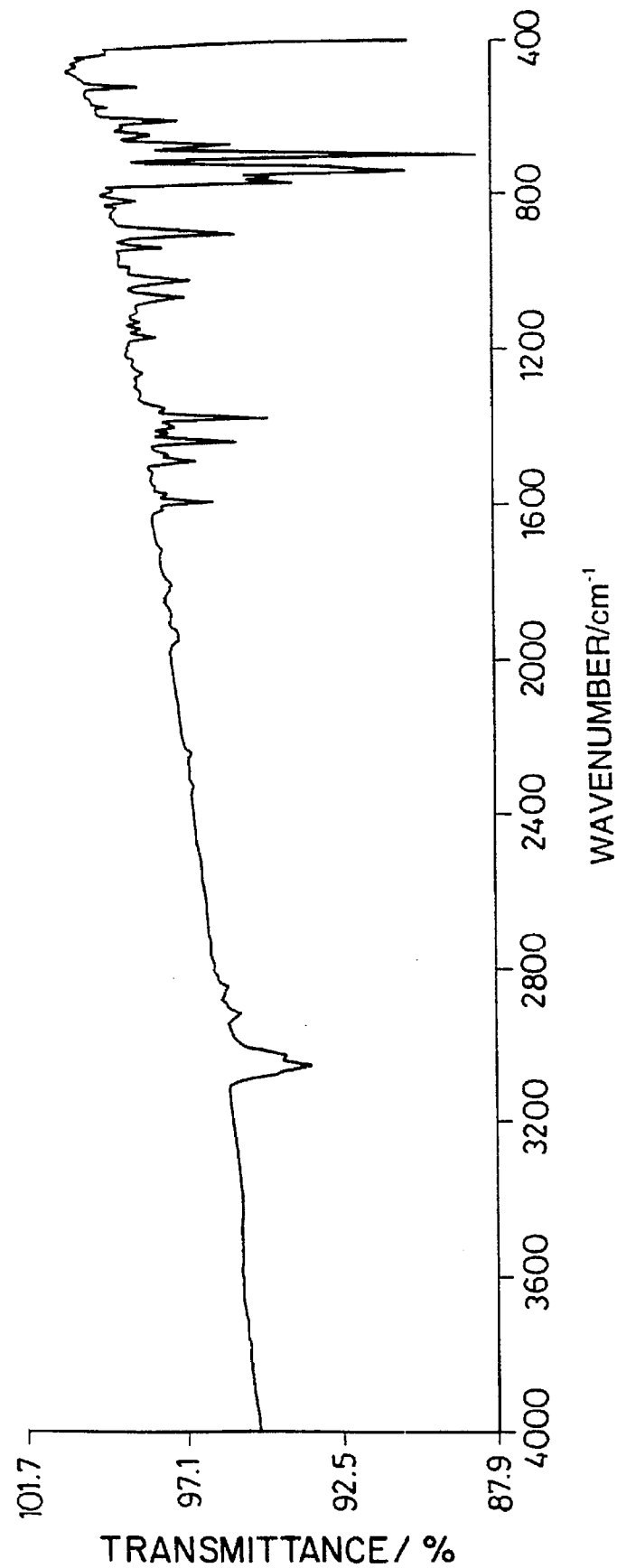
FIGS. 4 and 5 are graphs showing IR and NMR spectra of compound II-1 in Example 2, respectively.

IR absorption spectrum: FIG. 4

Figure 5:
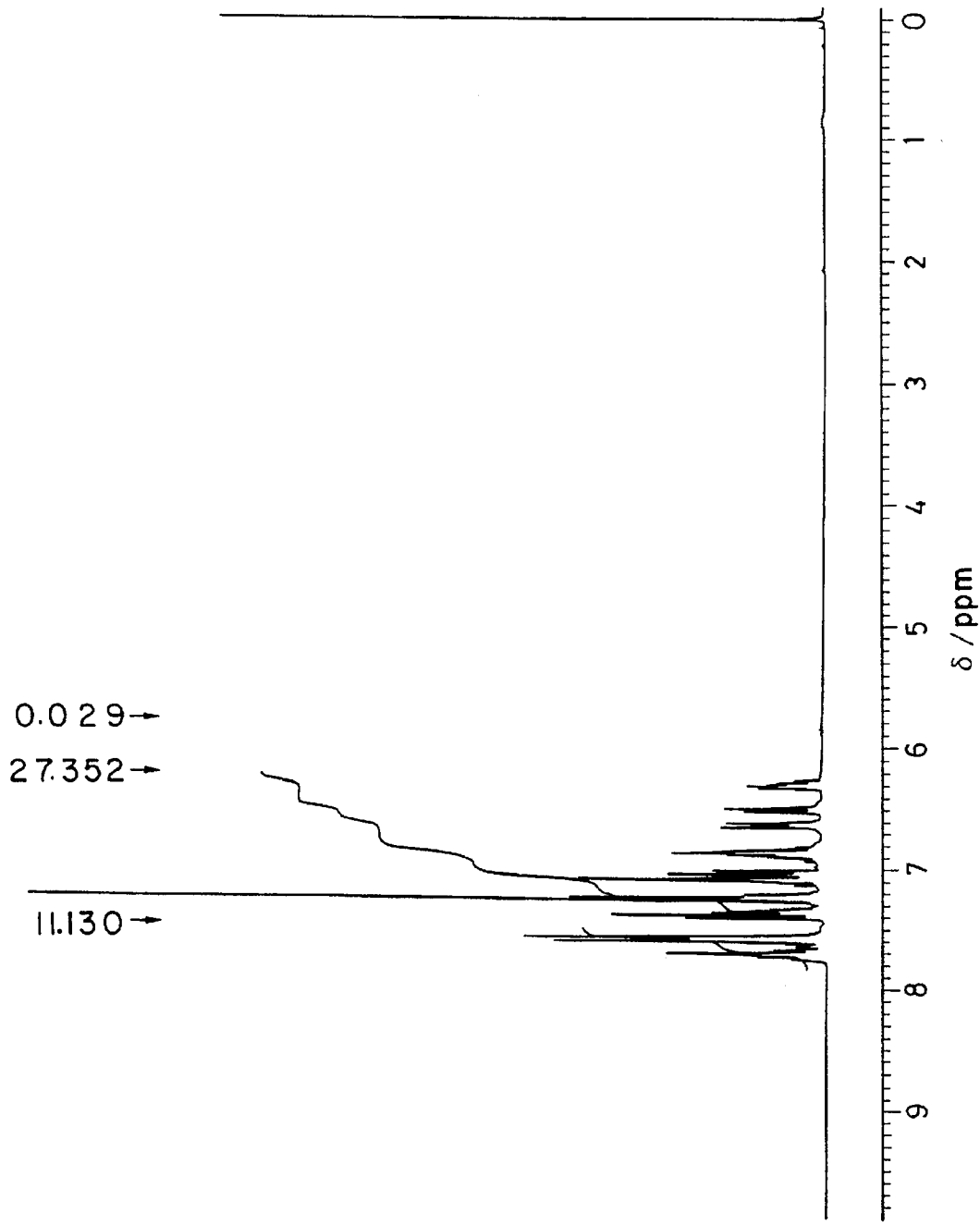

NMR spectrum: FIG. 5

Example 3

Synthesis of compound III-1

In a Schlenk flask purged with argon, 50 ml of THF solution of 2.22 g (5.46 mmol) of 4,4'-iodobiphenyl was added dropwise to 0.267 g (10 mmol) of activated magnesium, forming a Grignard reagent. To this reaction solution were added 0.4 g of NiCl$_2$ (dppe) and 4.00 g (10 mmol) of 2-chloro-9,10-diphenylanthracene. The reaction solution was refluxed at 60° C. for 4 hours. The reaction solution was poured into 1N aqueous hydrochloric acid, from which the product was extracted with toluene and chloroform, washed with water and then dried over magnesium sulfate. After the solvent was distilled off, the product was recrystallized from acetone/dichloromethane and purified through a silica column using toluene and hexanol as the extracting solvent, yielding 2.0 g of a yellowish white solid having blue-green fluorescence. This yellowish white solid, 1.0 g, was purified through sublimation, yielding 0.6 g of a pure yellowish white solid.

Mass analysis: m/e 586 (M$^+$)

Elemental analysis

|  | C | H |
|---|---|---|
| Calcd. (%) | 94.54 | 5.45 |
| Found (%) | 94.50 | 5.40 |

DSC: mp 350° C., Tg 120° C. Ionization potential: 5.95 eV

Note that the compound was also identified from the results of an IR absorption spectrum and NMR spectrum.

Example 4

Synthesis of compound V-1

In a Schlenk flask purged with argon, 50 ml of a THF solution of 2.02 g (4.97 mmol) of 4,4'-iodobiphenyl was added dropwise to 0.267 g (10 mmol) of activated magnesium, forming a Grignard reagent. This reaction solution was added dropwise to a THF solution of 1.04 g (5 mmol) of anthraquinone and stirred for one hour. Thereafter a THF solution of phenylmagnesium iodide was added dropwise to the reaction solution, which was refluxed at 60° C. for 2 hours. The reaction solution was poured into 1N aqueous hydrochloric acid, from which the product was extracted with toluene and chloroform, washed with water and then dried over magnesium sulfate. The product was dissolved in 100 ml of acetic acid, to which an aqueous solution of hydrogen iodide was added dropwise. The solution was stirred for 4 hours. A hydrochloric acid solution of tin dichloride (SnCl$_2$) was added to the solution until the liberated iodine disappeared. The product was extracted with chloroform and toluene and dried over magnesium sulfate. After the solvent was distilled off, the product was purified through a silica column using toluene as the extracting solvent and recrystallized from acetone/toluene.

Mass analysis: m/e 658 (M$^+$)

Elemental analysis

|  | C | H |
|---|---|---|
| Calcd. (%) | 94.80 | 5.20 |
| Found (%) | 94.58 | 5.10 |

Note that the compound was also identified from the results of an IR absorption spectrum and NMR spectrum.

Example 5

Synthesis of compound VII-2

In a Schlenk flask purged with argon, 1.0 g (2.6 mmol) of bianthrone was dissolved in 50 ml of THF, to which an ether solution of 6.0 mmol of 4-methylphenylmagnesium bromide was added dropwise. The solution was refluxed for 4 hours. The reaction solution was poured into an aqueous ammonium chloride solution, from which the product was extracted with toluene and chloroform, washed with water and then dried over magnesium sulfate. The product was dissolved in 100 ml of acetic acid, to which an aqueous solution of hydrogen iodide was added dropwise. The solution was stirred for 4 hours. A hydrochloric acid solution of tin dichloride (SnCl$_2$) was added dropwise to the solution, which was stirred for a further 1 hour at 100° C. Thereafter water was added to the solution, from which the product was extracted with chloroform and toluene and dried over magnesium sulfate. After the solvent was distilled off, the product was washed with acetone and methanol, purified through a silica column using a mixture of toluene and hexane (1:4) as the extracting solvent, and recrystallized from toluene, yielding 0.8 g of a white solid.

Mass analysis: m/e 535 (M+1)$^+$

Figure 6:
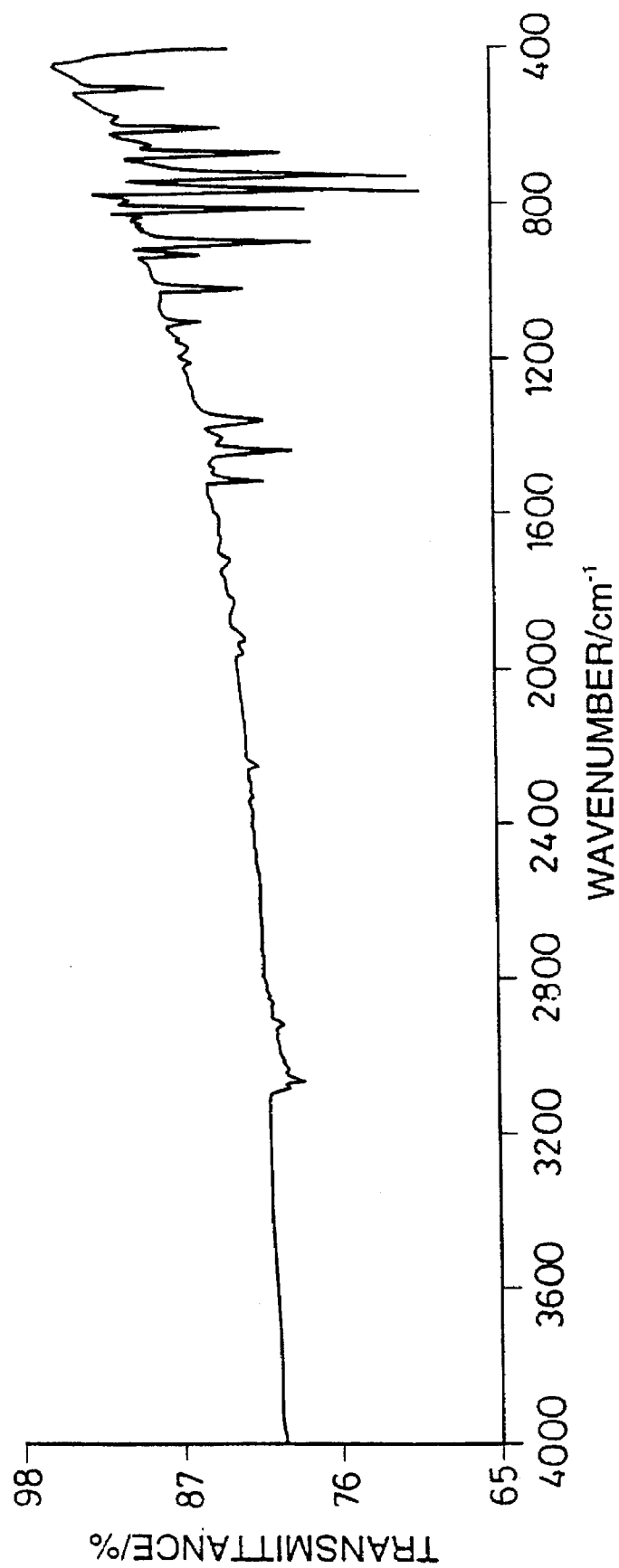
FIGS. 6 and 7 are graphs showing IR and NMR spectra of compound VII-2 in Example 5, respectively.

IR absorption spectrum: FIG. 6

Figure 7:
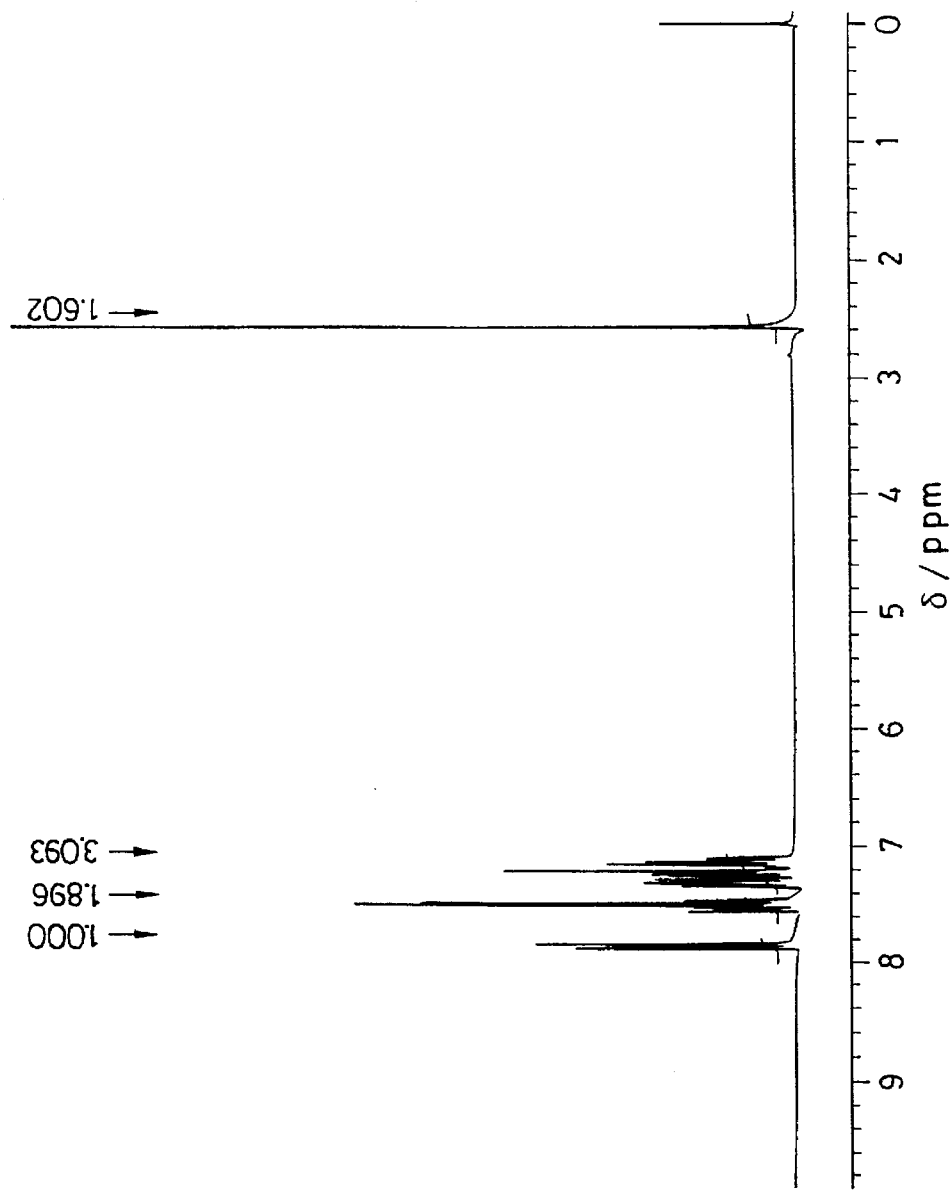

NMR spectrum: FIG. 7

DSC: mp 365° C., Tg 162° C.

On elemental analysis, the found values were well coincident with the calculated values.

Example 6

Synthesis of compound VII-1

It was synthesized as in Example 5.

Mass analysis: m/e 506 (M$^+$)

Figure 8:
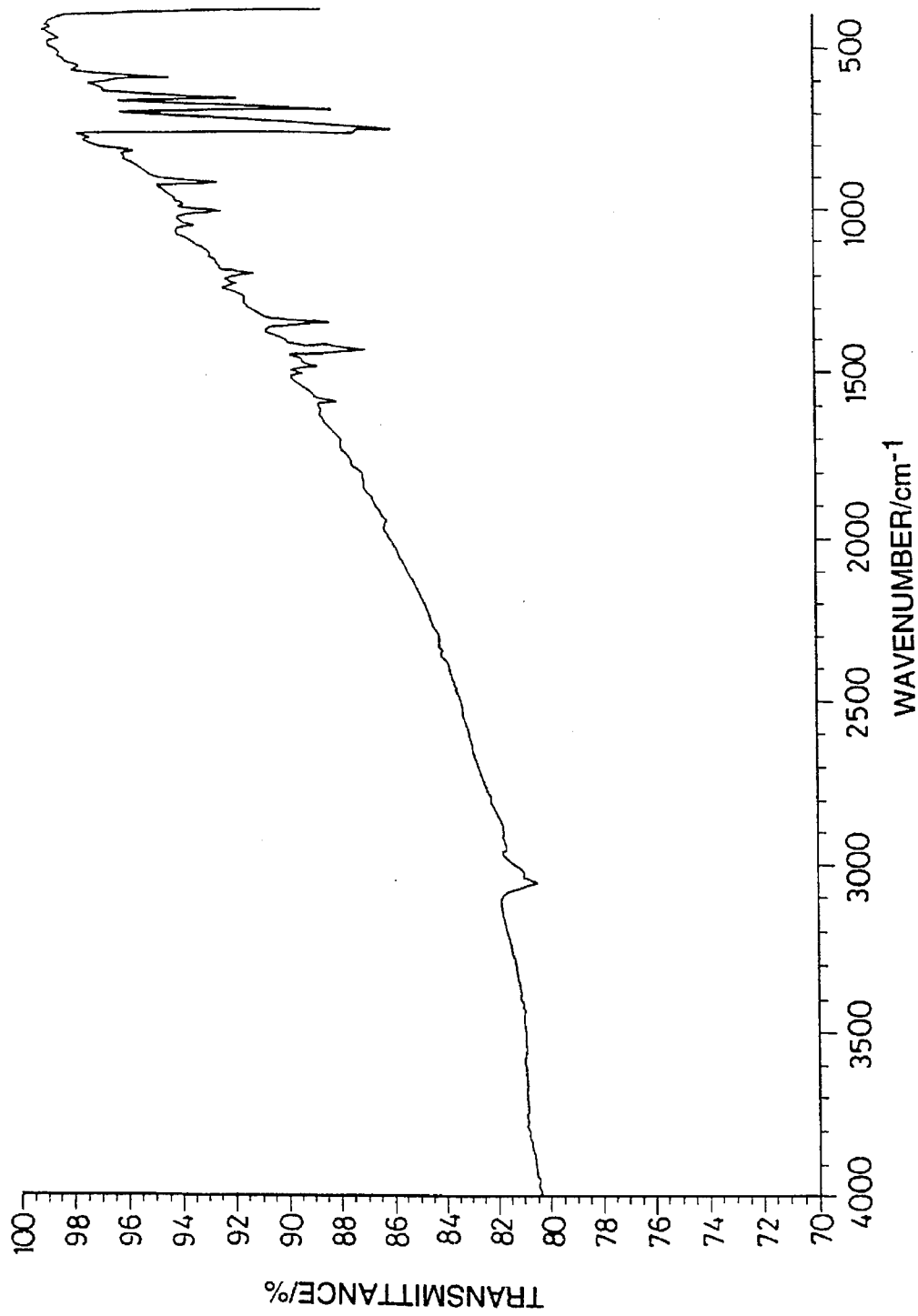
FIGS. 8 and 9 are graphs showing IR and NMR spectra of compound VII-1 in Example 6, respectively.

IR spectrum: FIG. 8

Figure 9:
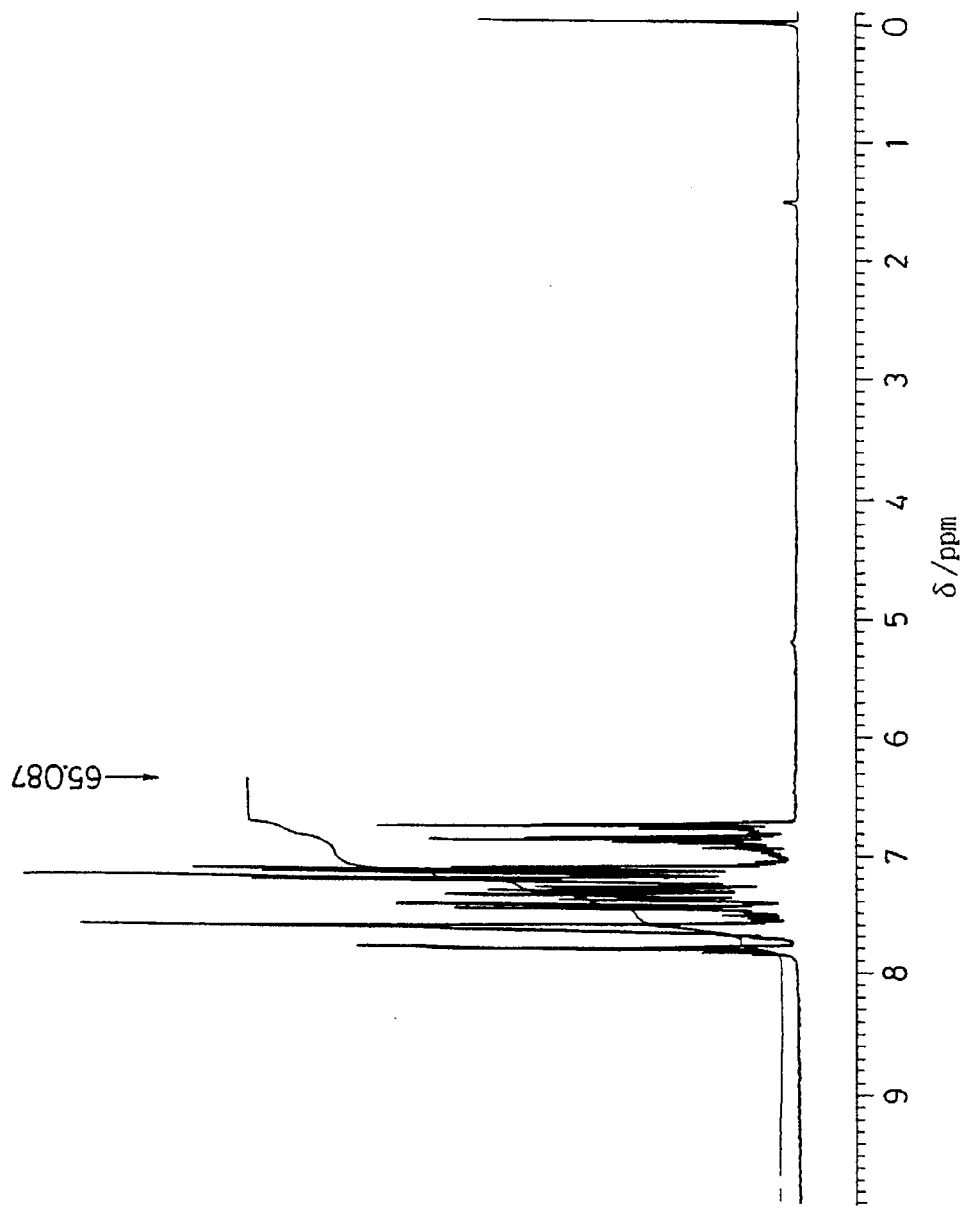

NMR spectrum: FIG. 9

DSC: mp 350° C., Tg 130° C.

On elemental analysis, the found values were well coincident with the calculated values.

Example 7

Synthesis of compound VII-3

It was synthesized as in Example 5.

Mass analysis: m/e 619 (M+1)$^+$

Figure 10:
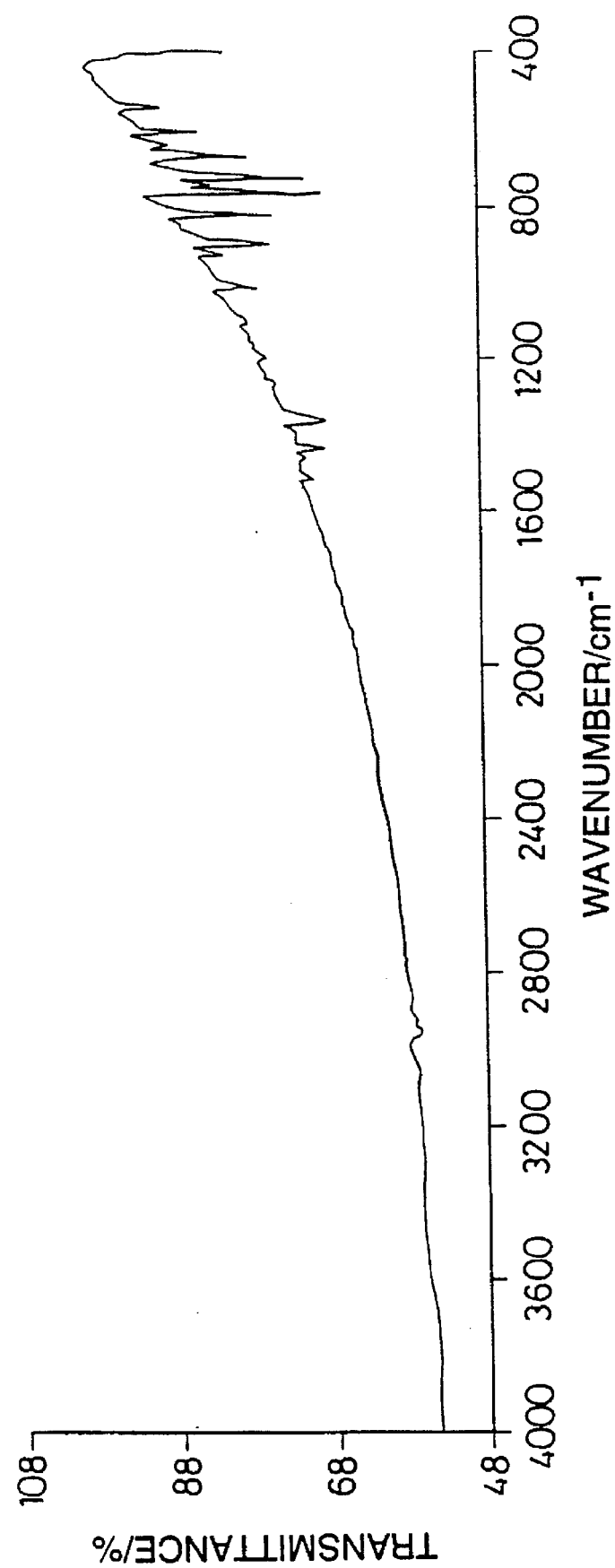
FIGS. 10 and 11 are graphs showing IR and NMR spectra of compound VII-3 in Example 7, respectively.

IR spectrum: FIG. 10

Figure 11:
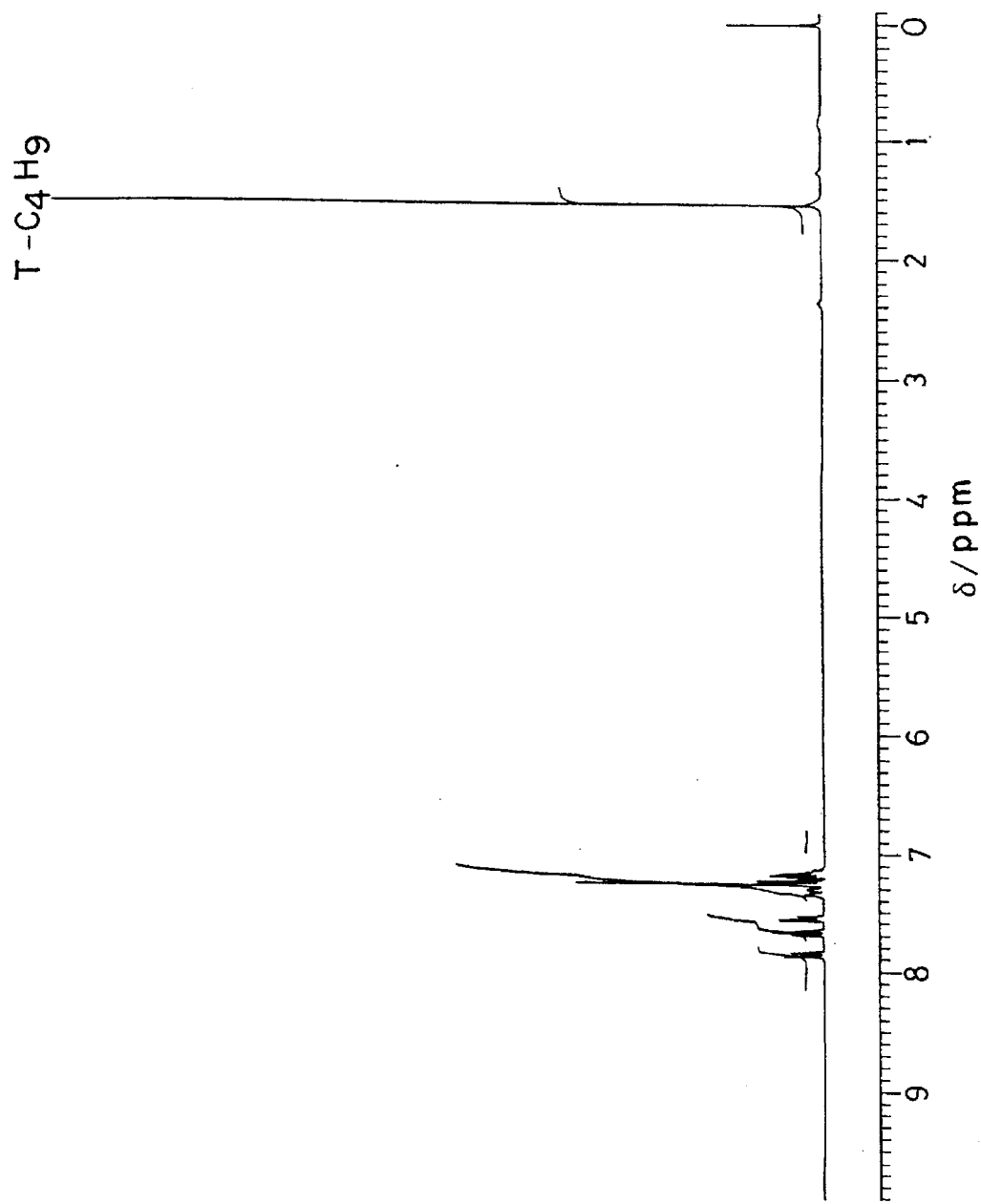

NMR spectrum: FIG. 11

DSC: mp 411° C.

On elemental analysis, the found values were well coincident with the calculated values.

Example 8

Synthesis of compound VII-4

It was synthesized as in Example 5.

Mass analysis: m/e 566 (M+1)$^+$

Figure 12:
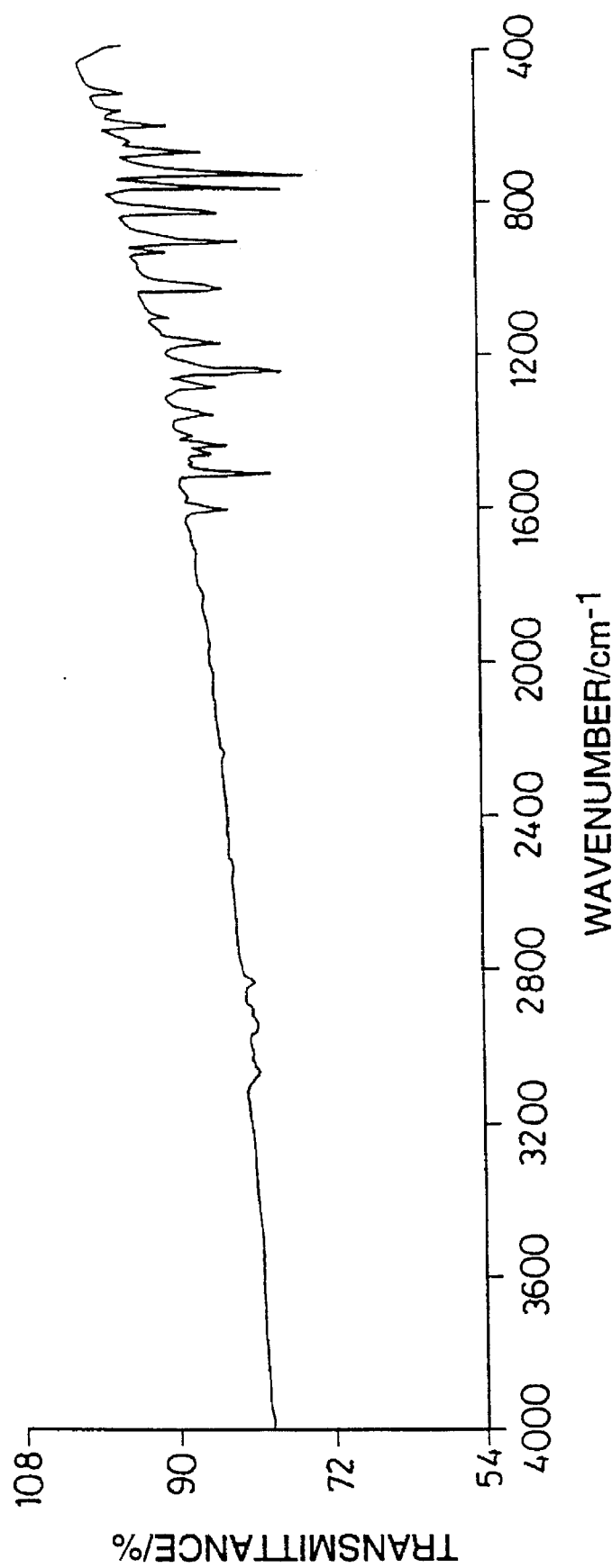
FIGS. 12 and 13 are graphs showing IR and NMR spectra of compound VII-4 in Example 8, respectively.

IR spectrum: FIG. 12

Figure 13:
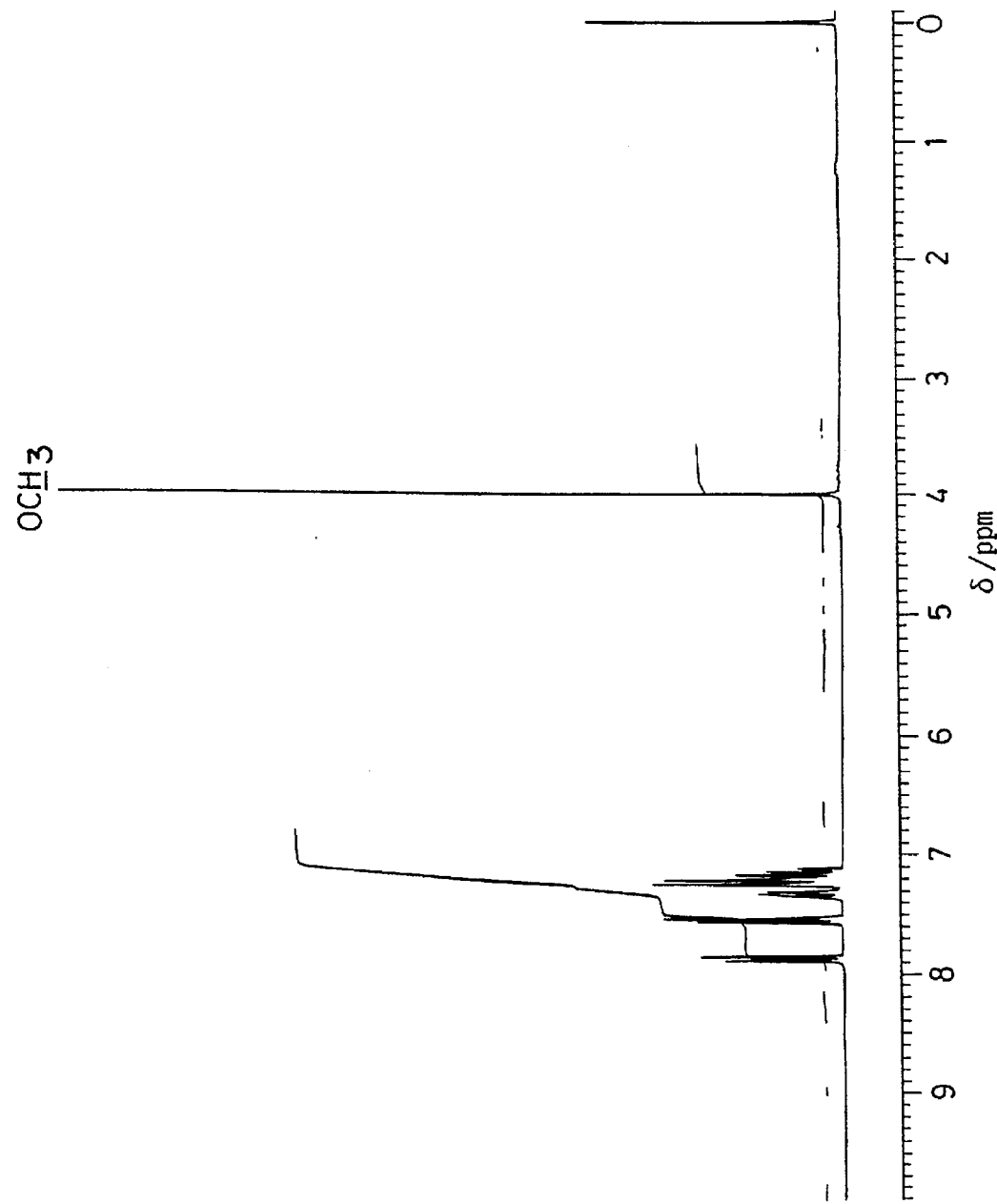
Figure 14:
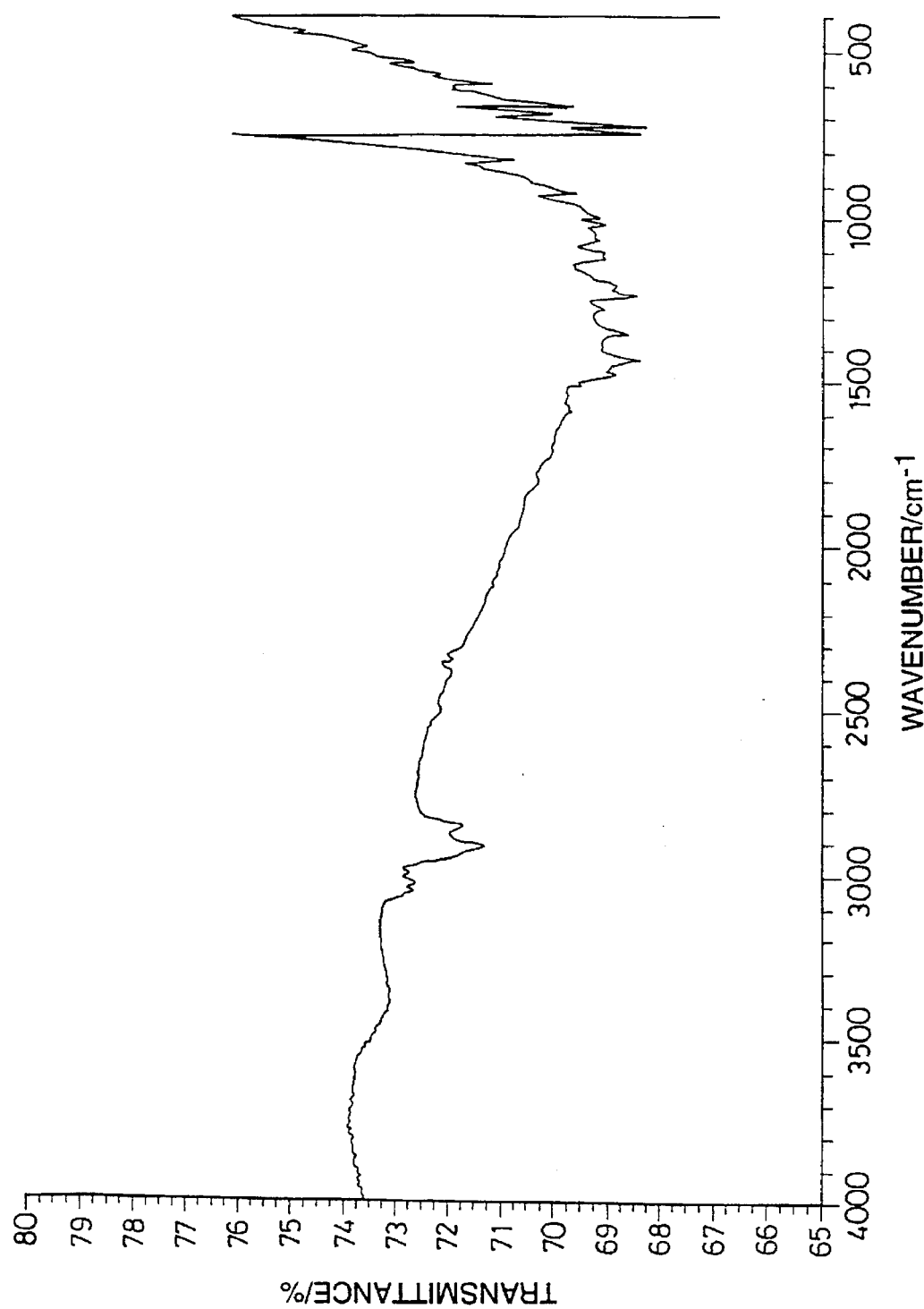
FIGS. 14 and 15 are graphs showing IR and NMR spectra of compound VII-8 in Example 9, respectively.

NMR spectrum: FIG. 13

On elemental analysis, the found values were well coincident with the calculated values.

Example 9

Synthesis of compound VII-8

It was synthesized as in Example 5.

Mass analysis: m/e 658 (M$^+$)

IR spectrum: FIG.

Figure 15:
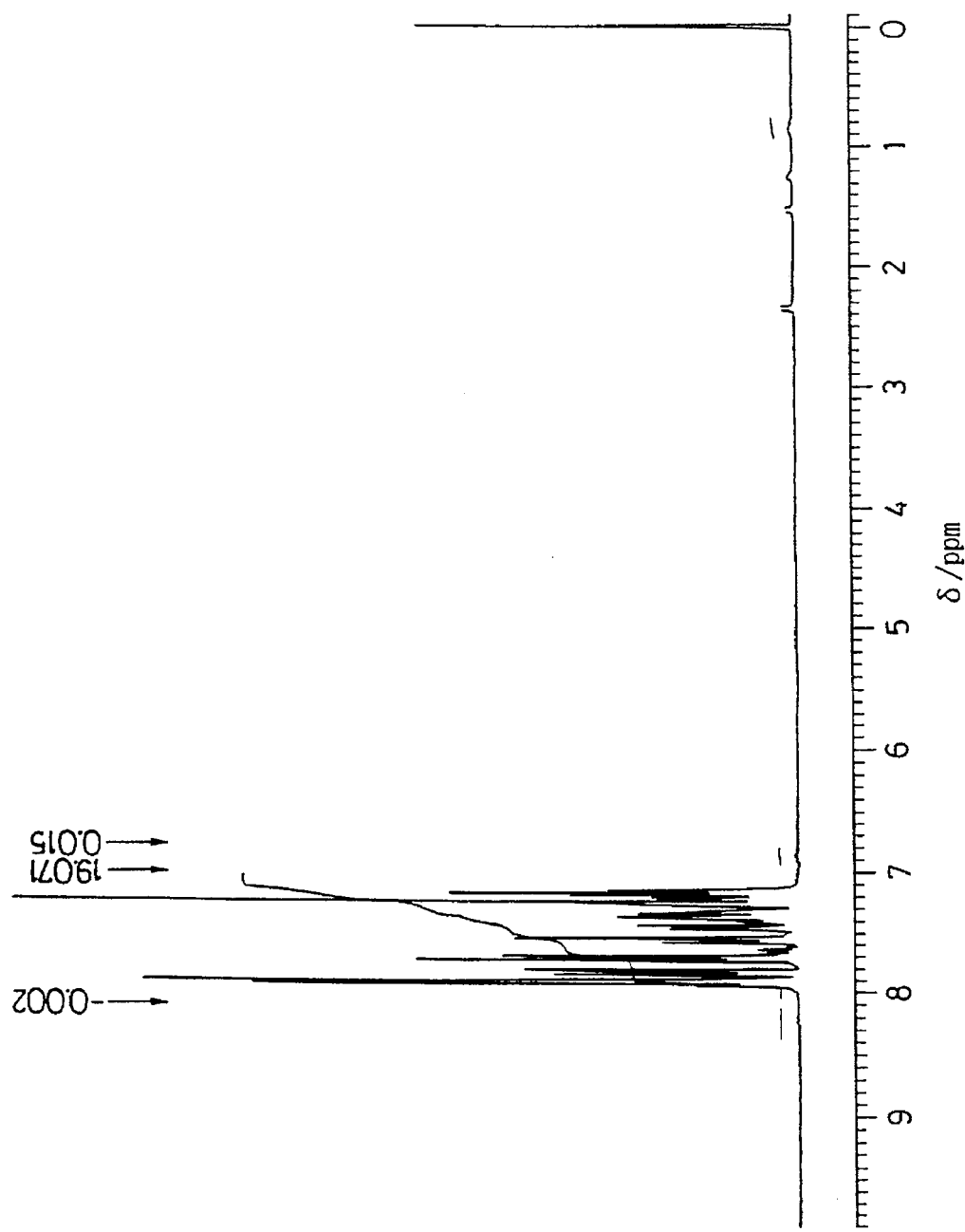

NMR spectrum: FIG. 15

DSC: mp 345° C., Tg 188° C.

On elemental analysis, the found values were well coincident with the calculated values.

Example 10

Synthesis of compound VII-12

It was synthesized as in Example 5.

Figure 16:
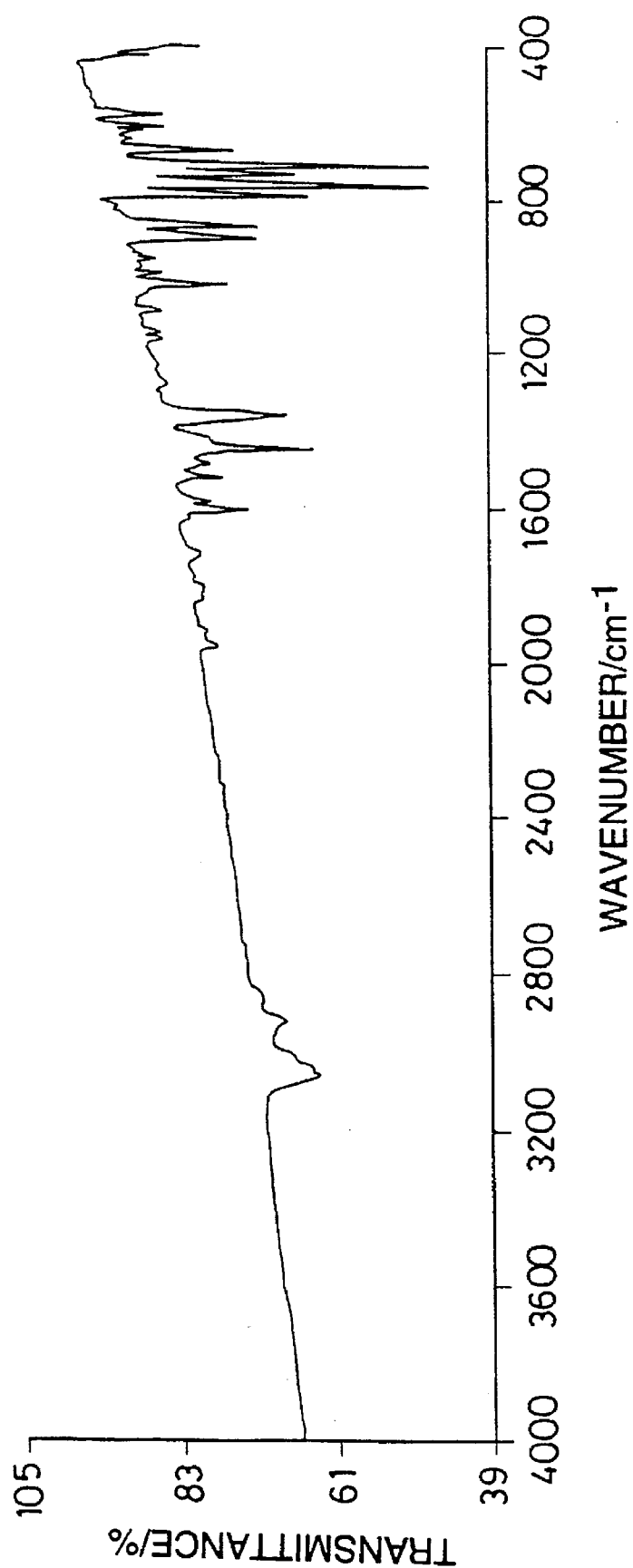
FIGS. 16 and 17 are graphs showing IR and NMR spectra of compound VII-12 in Example 10, respectively.
Figure 17:
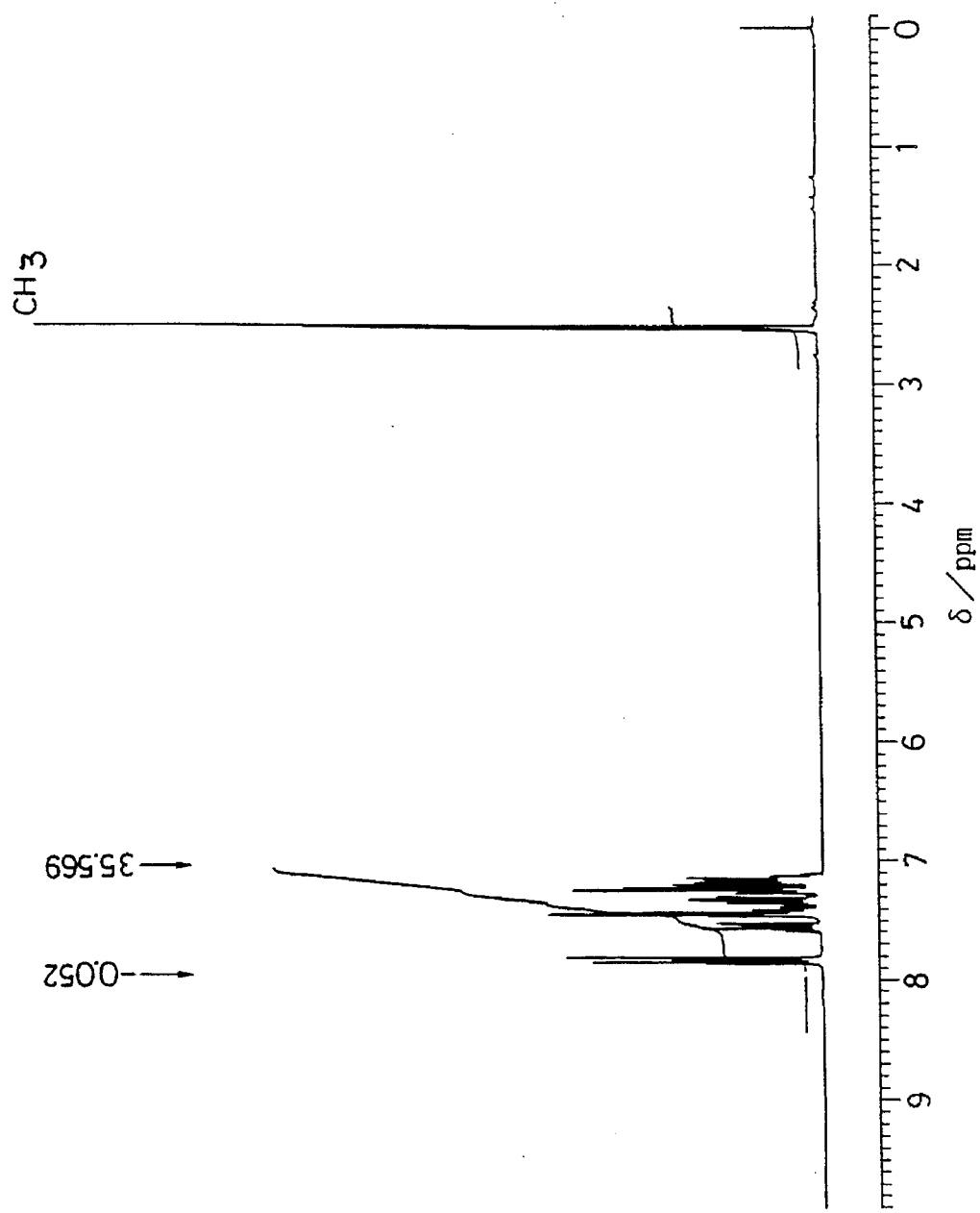

Mass analysis: m/e 535 (M+1)$^+$
IR spectrum: FIG. 16
NMR spectrum: FIG. 17
DSC: mp 391° C., Tg 166° C.

On elemental analysis, the found values were well coincident with the calculated values.

Example 11

Synthesis of compound VII-14

Figure 18:
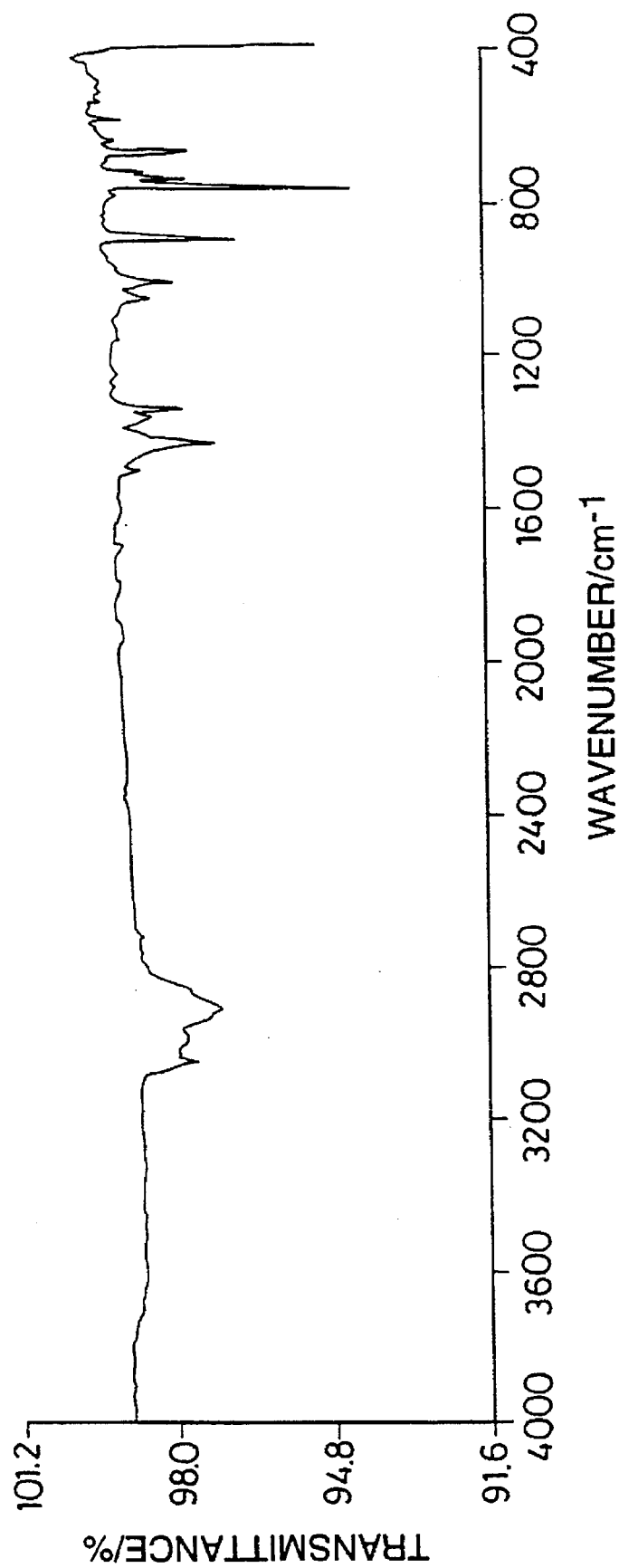
FIGS. 18 and 19 are graphs showing IR and NMR spectra of compound VII-14 in Example 11, respectively.
Figure 19:
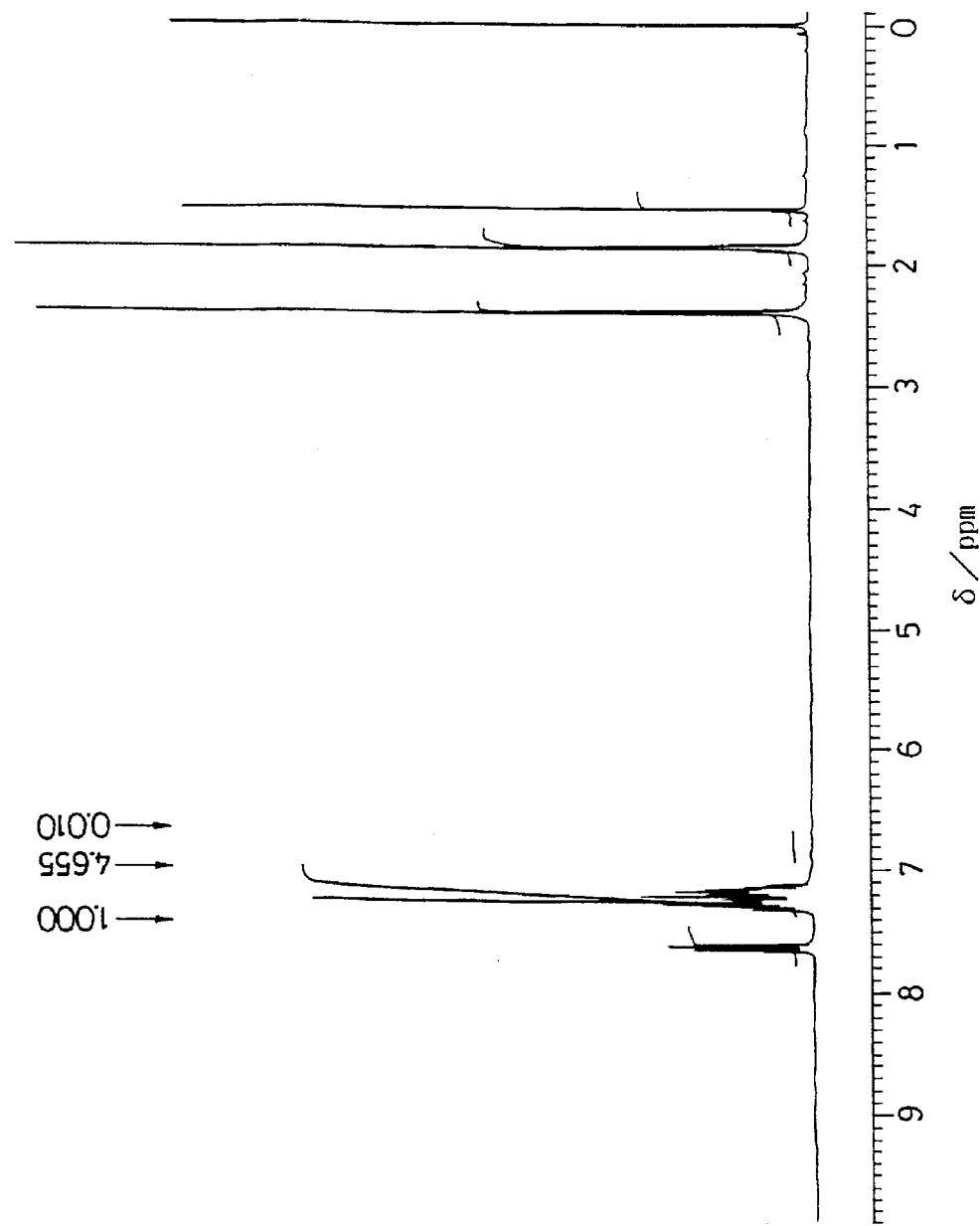

It was synthesized as in Example 5.
Mass analysis: m/e 647 (M+1)$^+$
IR spectrum: FIG. 18
NMR spectrum: FIG. 19
DSC: sublimated at 414° C.

On elemental analysis, the found values were well coincident with the calculated values.

Example 12

Synthesis of compound VII-15

Figure 20:
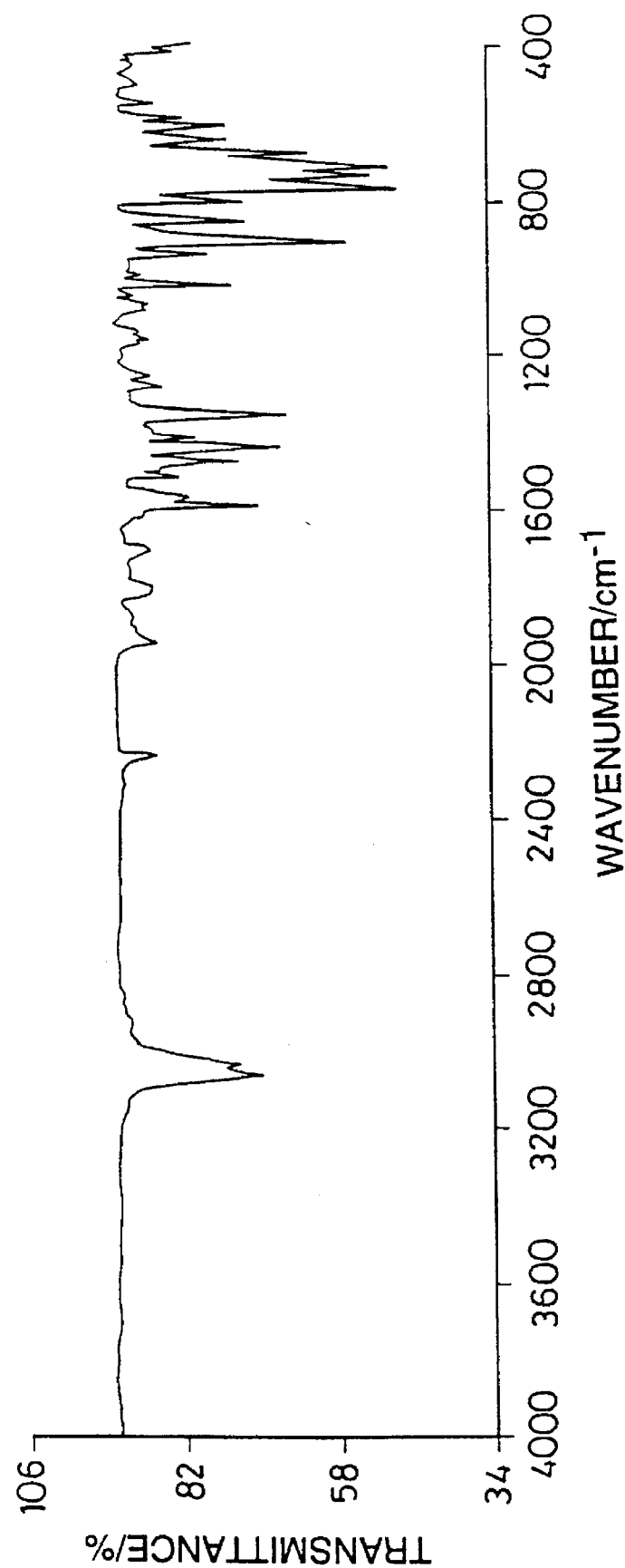
FIGS. 20 and 21 are graphs showing IR and NMR spectra of compound VII-15 in Example 12, respectively.
Figure 21:
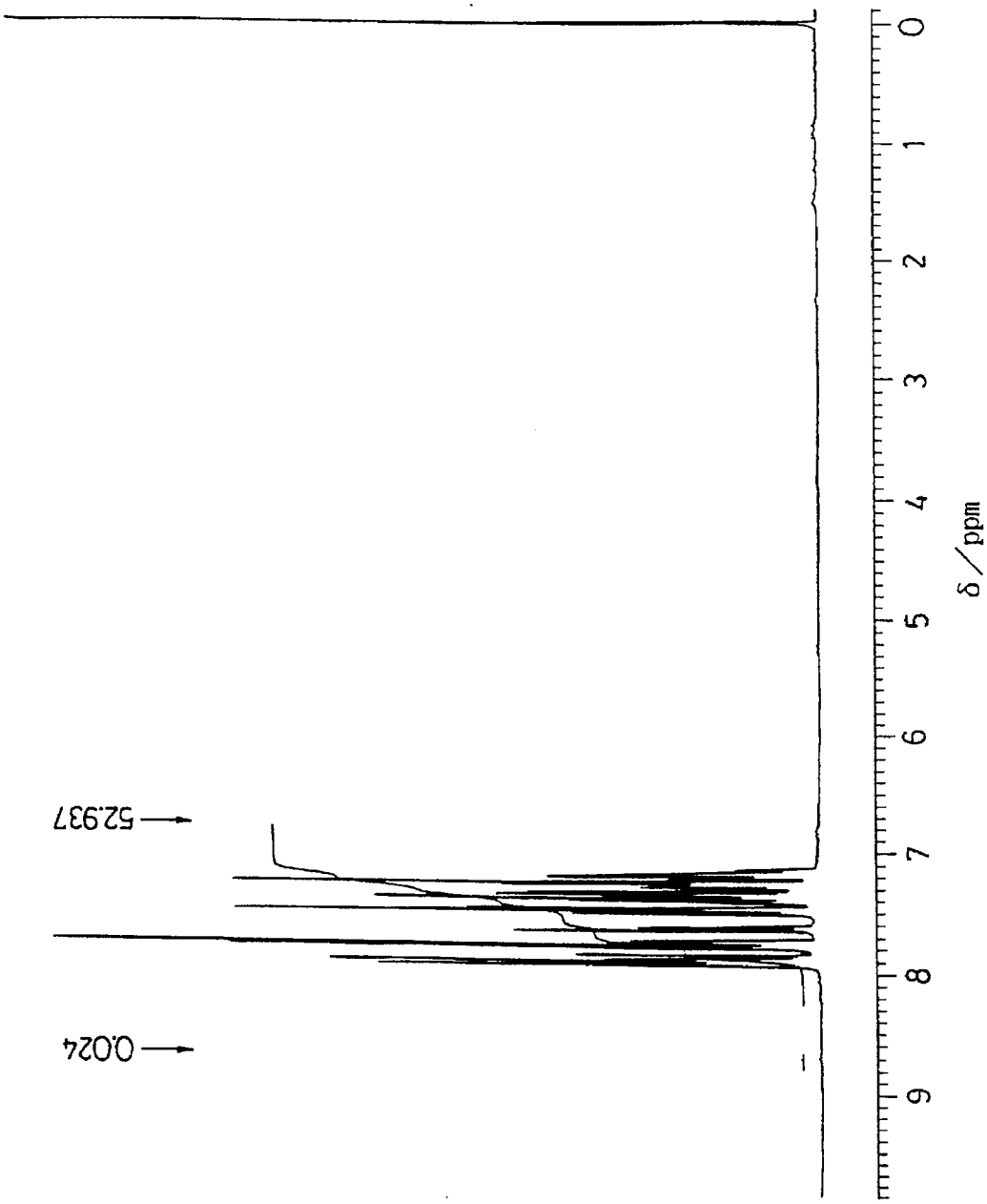

It was synthesized as in Example 5.
Mass analysis: m/e 659 (M+1)$^+$
IR spectrum: FIG. 20
NMR spectrum: FIG. 21
DSC: mp 323° C., Tg 165° C.

On elemental analysis, the found values were well coincident with the calculated values.

Example 13

Synthesis of compound VII-16

Figure 22:
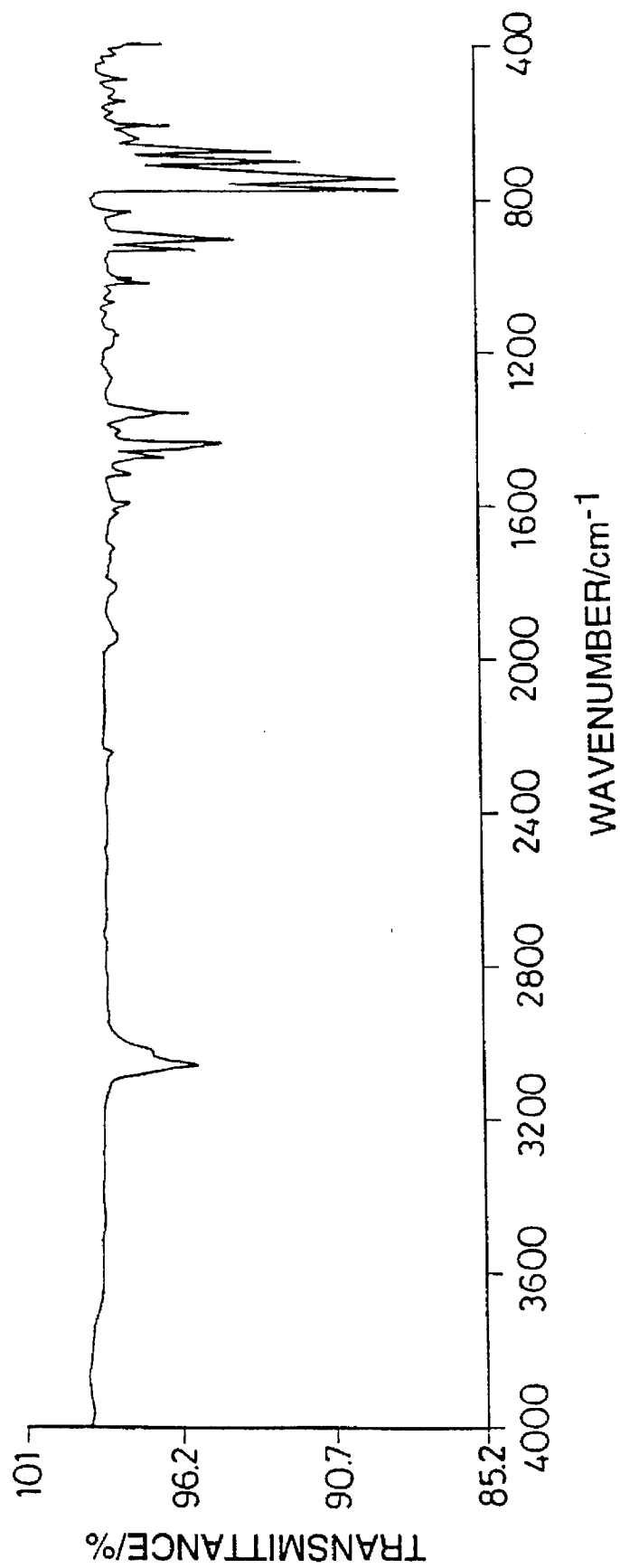
FIGS. 22 and 23 are graphs showing IR and NMR spectra of compound VII-16 in Example 13, respectively.
Figure 23:
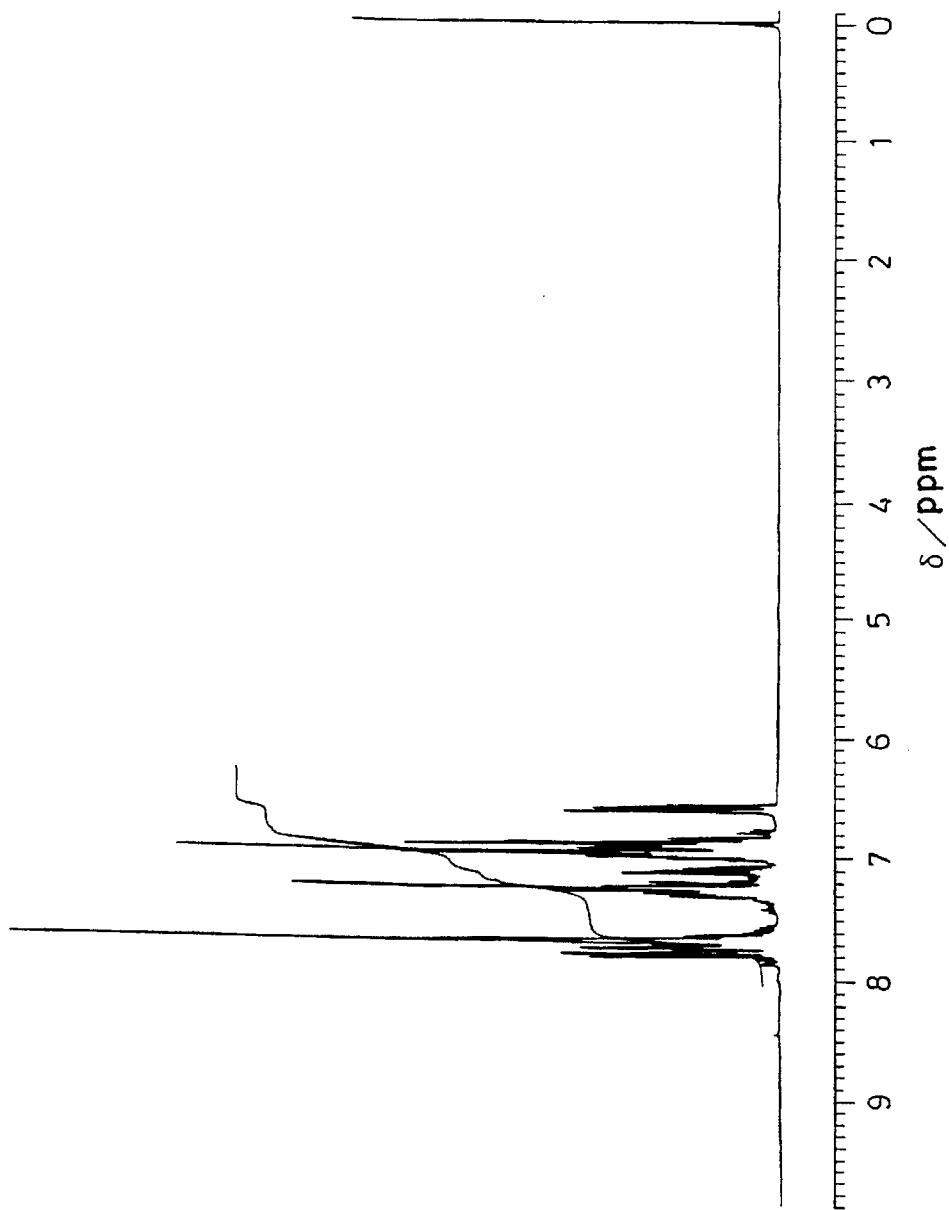

It was synthesized as in Example 5.
Mass analysis: m/e 659 (M+1)$^+$
IR spectrum: FIG. 22
NMR spectrum: FIG. 23
DSC: mp 295° C., Tg 141° C.

On elemental analysis, the found values were well coincident with the calculated values.

Example 14

Synthesis of compound VII-24

Figure 24:
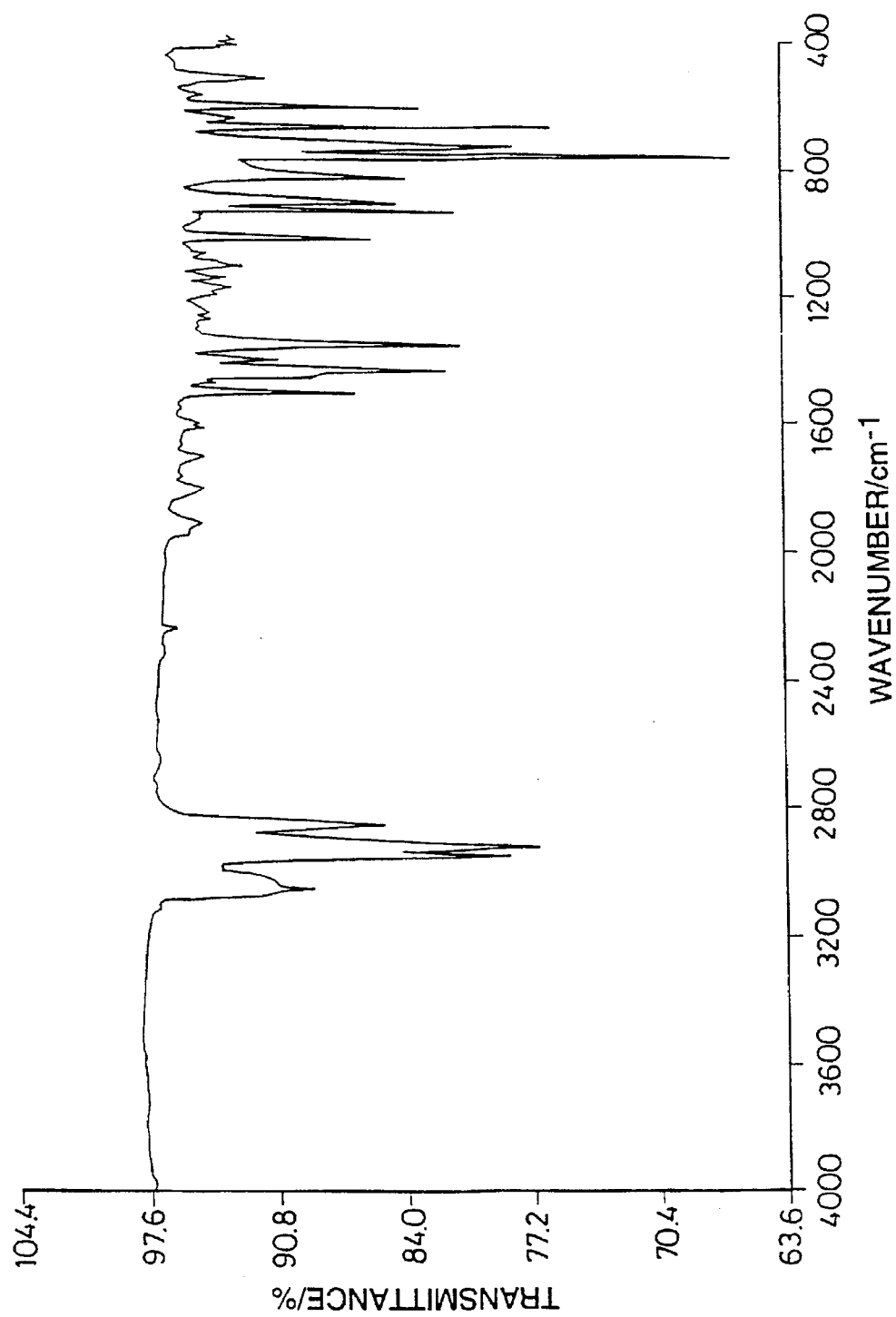
FIGS. 24 and 25 are graphs showing IR and NMR spectra of compound VII-24 in Example 14, respectively.
Figure 25:
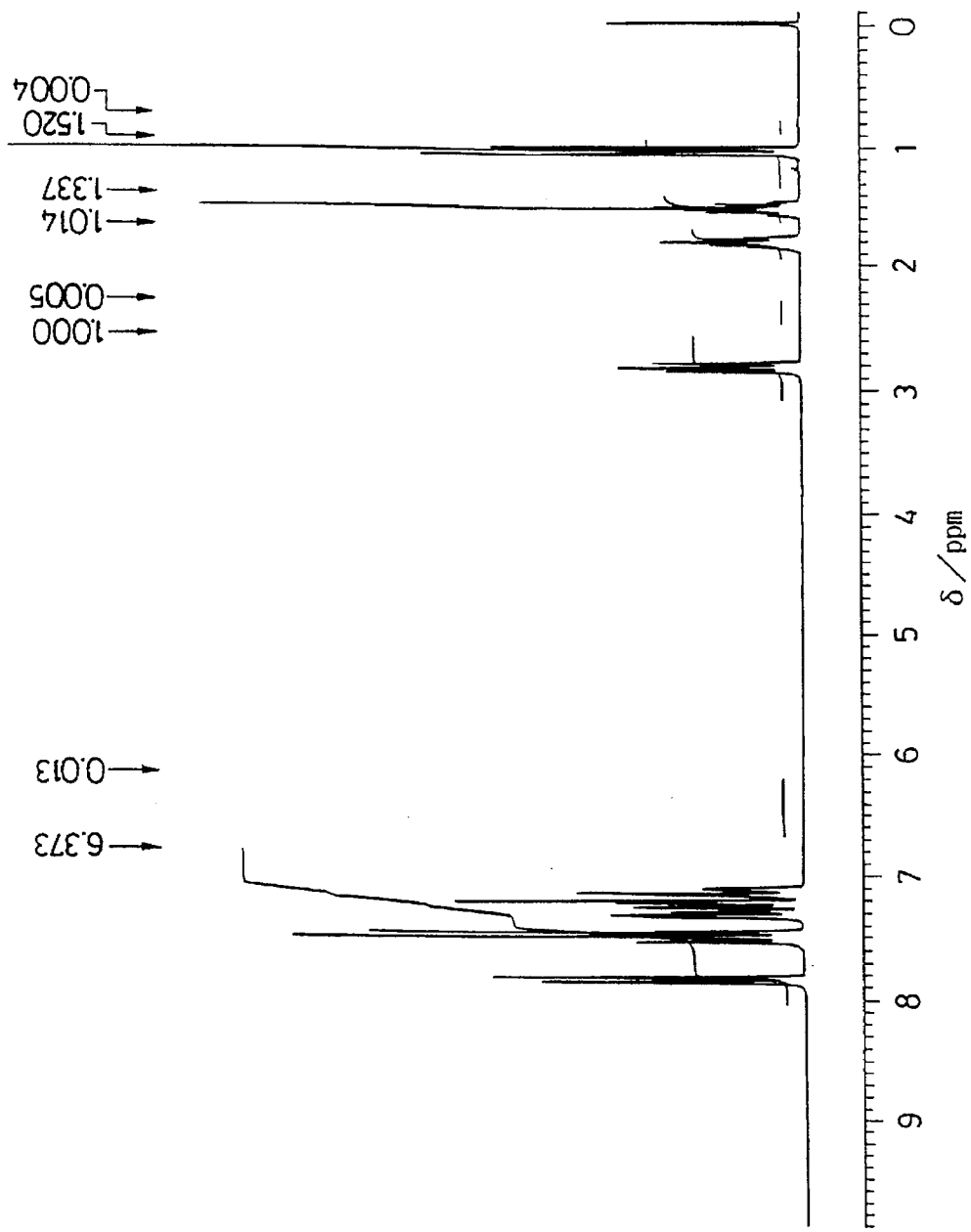

It was synthesized as in Example 5.
Mass analysis: m/e 618 (M$^+$)
IR spectrum: FIG. 24
NMR spectrum: FIG. 25
DSC: mp 273° C., Tg 105° C.

On elemental analysis, the found values were well coincident with the calculated values.

Example 15

Synthesis of compound VII-25

Figure 26:
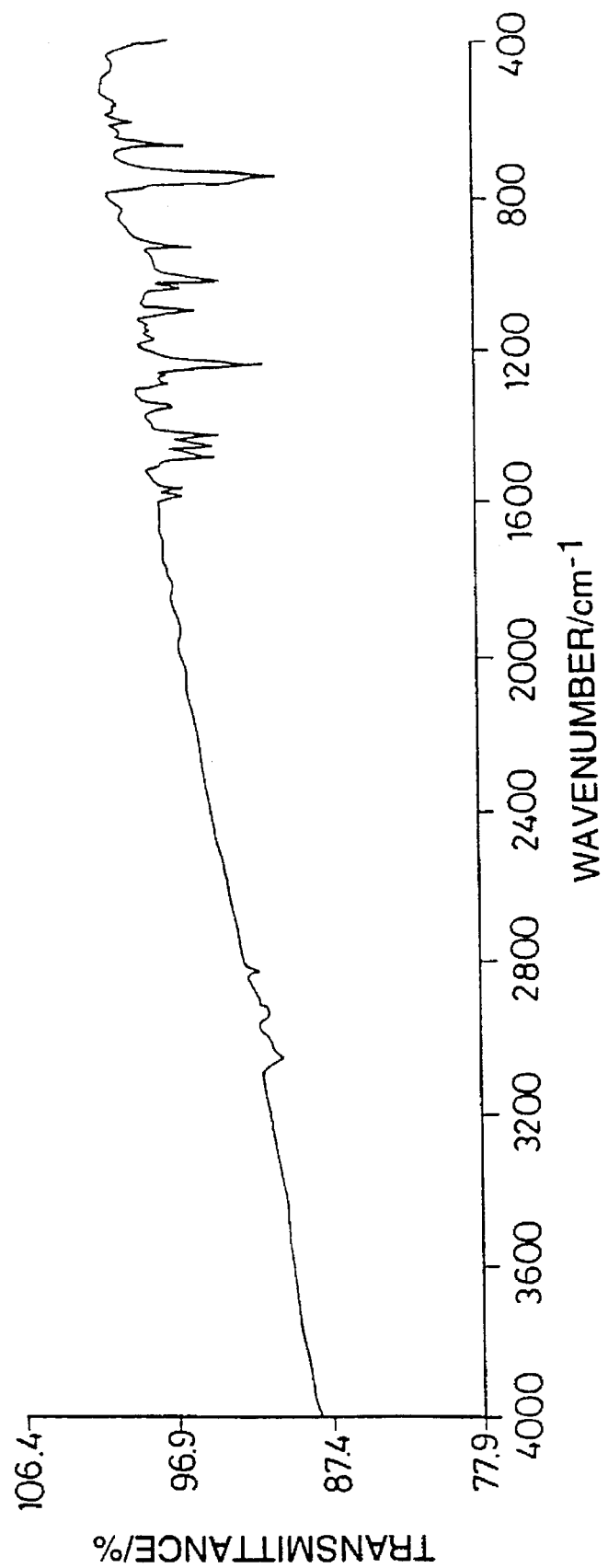
FIGS. 26 and 27 are graphs showing IR and NMR spectra of compound VII-25 in Example 15, respectively.
Figure 27:
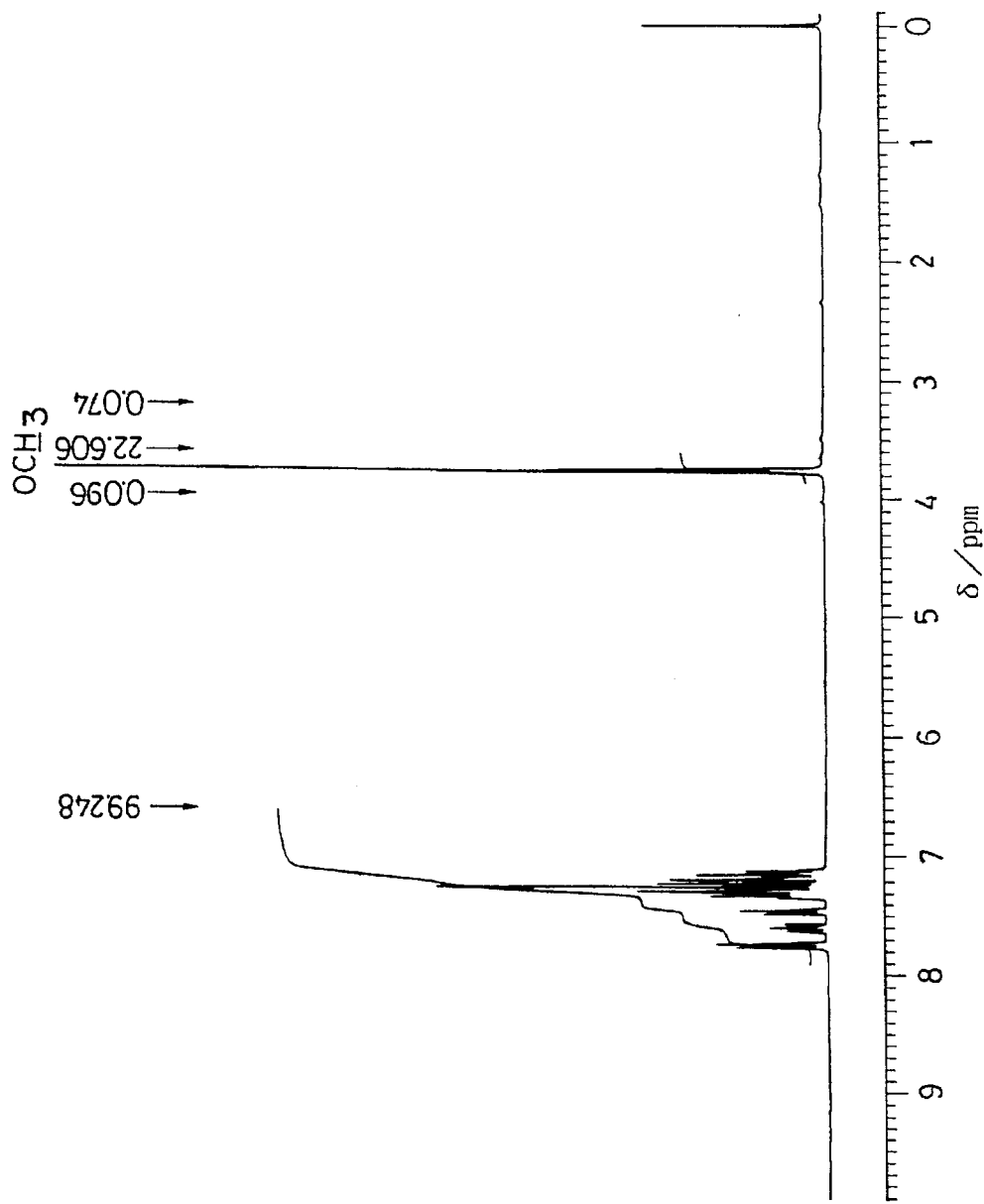

It was synthesized as in Example 5.
Mass analysis: m/e 567 (M+1)$^+$
IR spectrum: FIG. 26
NMR spectrum: FIG. 27

On elemental analysis, the found values were well coincident with the calculated values.

Example 16

Synthesis of compound VII-26

Figure 28:
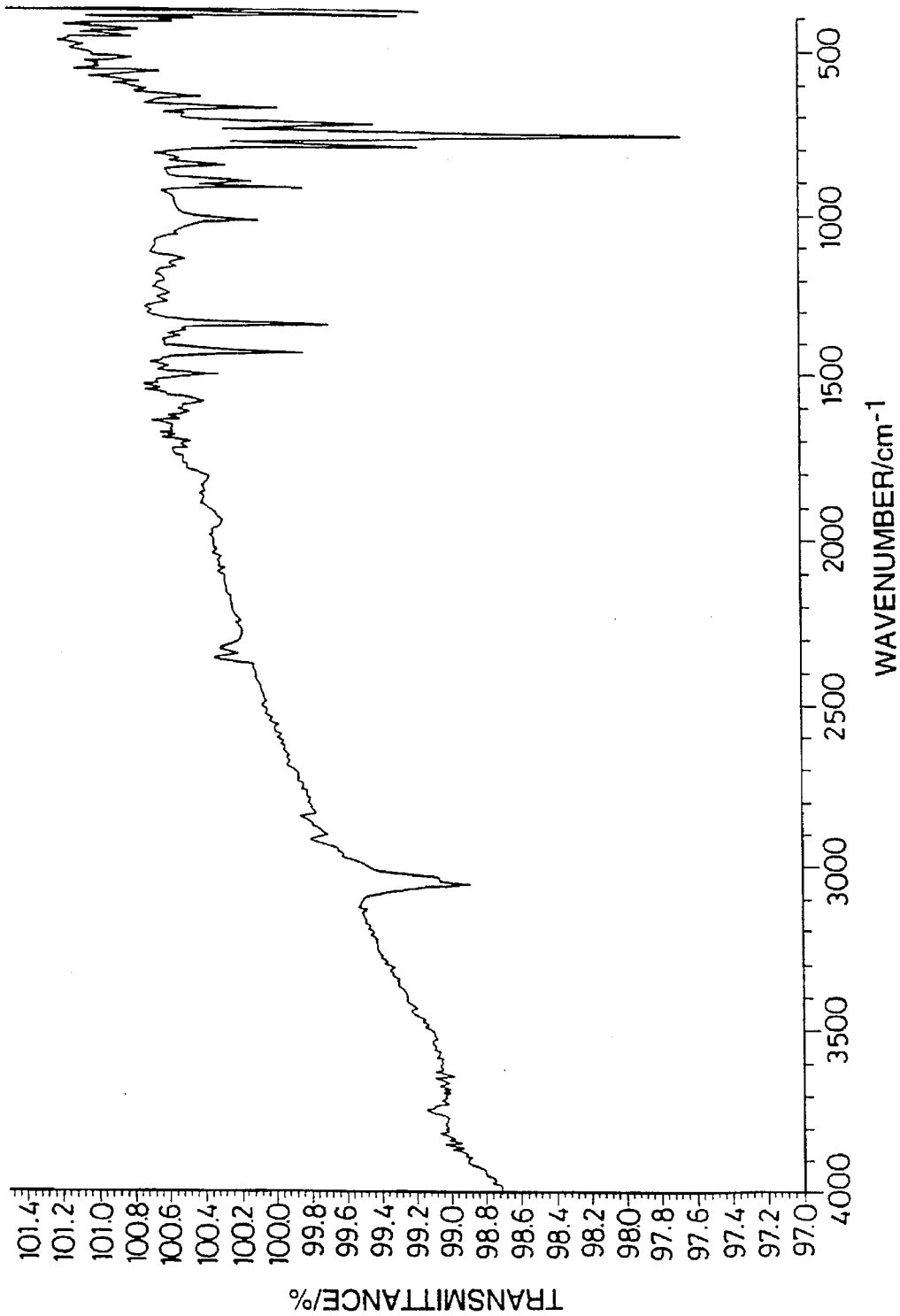
FIGS. 28 and 29 are graphs showing IR and NMR spectra of compound VII-26 in Example 16, respectively.
Figure 29:
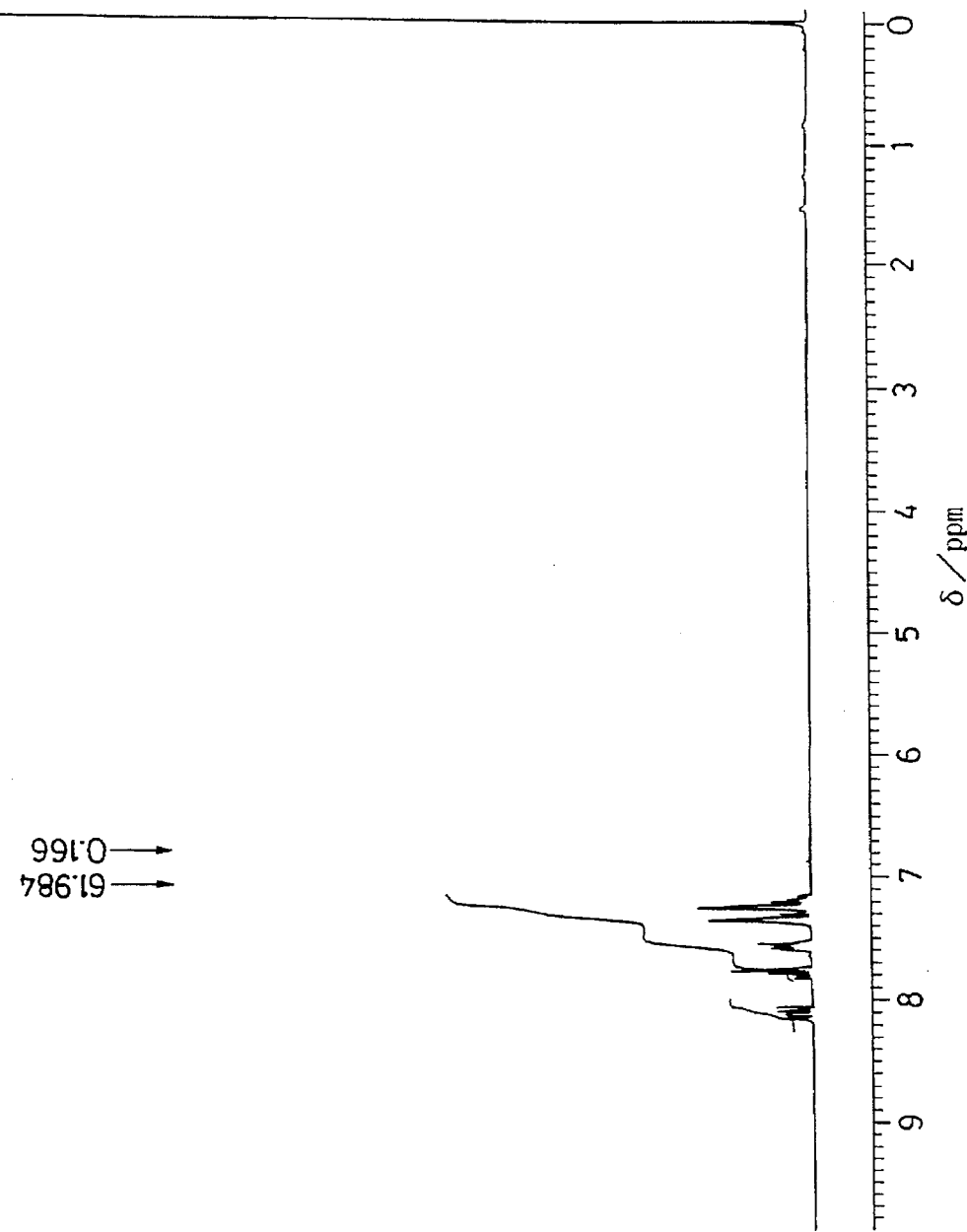

It was synthesized as in Example 5.
Mass analysis: m/e 606 (M$^+$)
IR spectrum: FIG. 28
NMR spectrum: FIG. 29
DSC: mp 453° C., Tg 235° C.

On elemental analysis, the found values were well coincident with the calculated values.

Example 17

Synthesis of compound I-20

Figure 30:
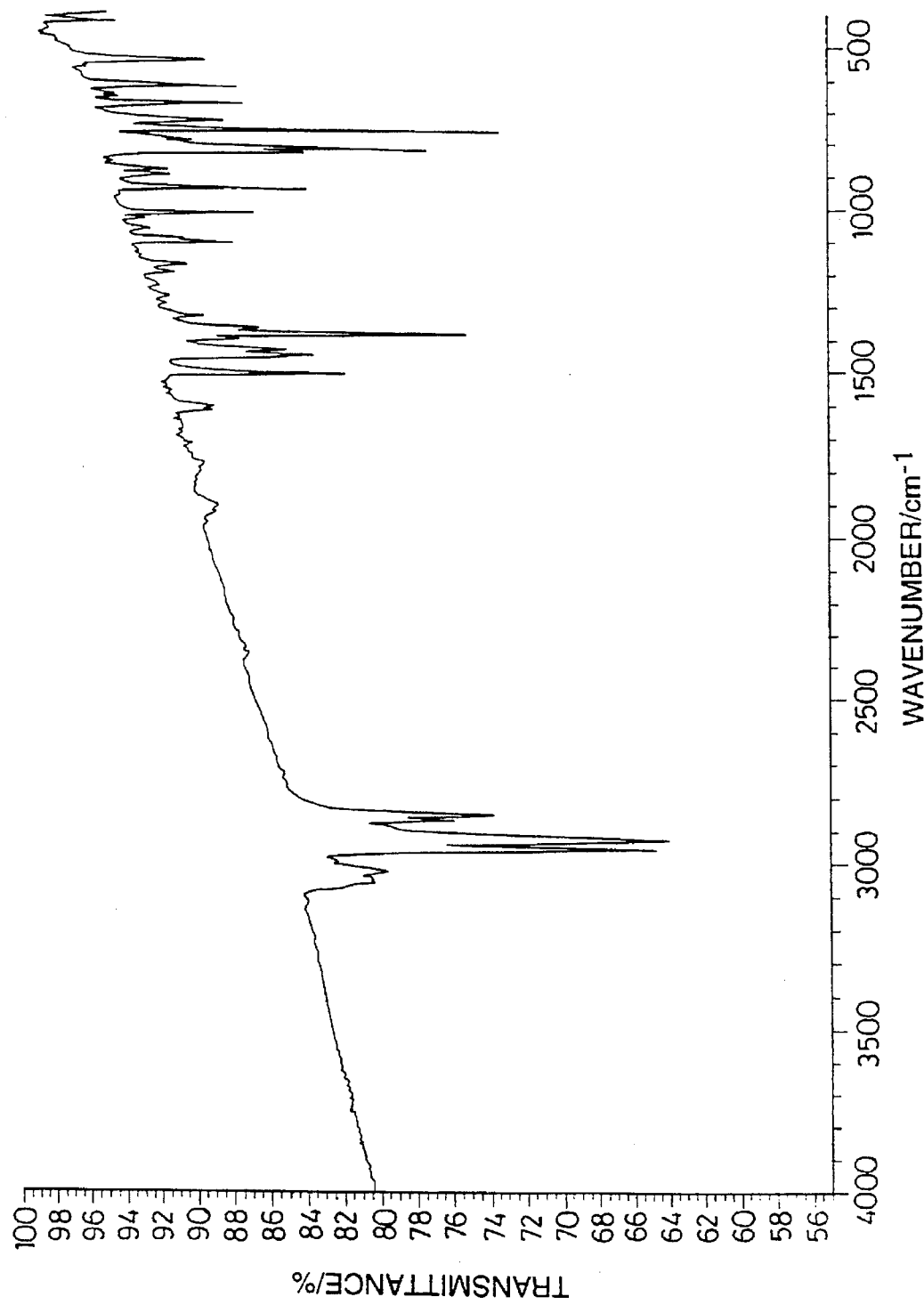
FIGS. 30 and 31 are graphs showing IR and NMR spectra of compound I-20 in Example 17, respectively.
Figure 31:
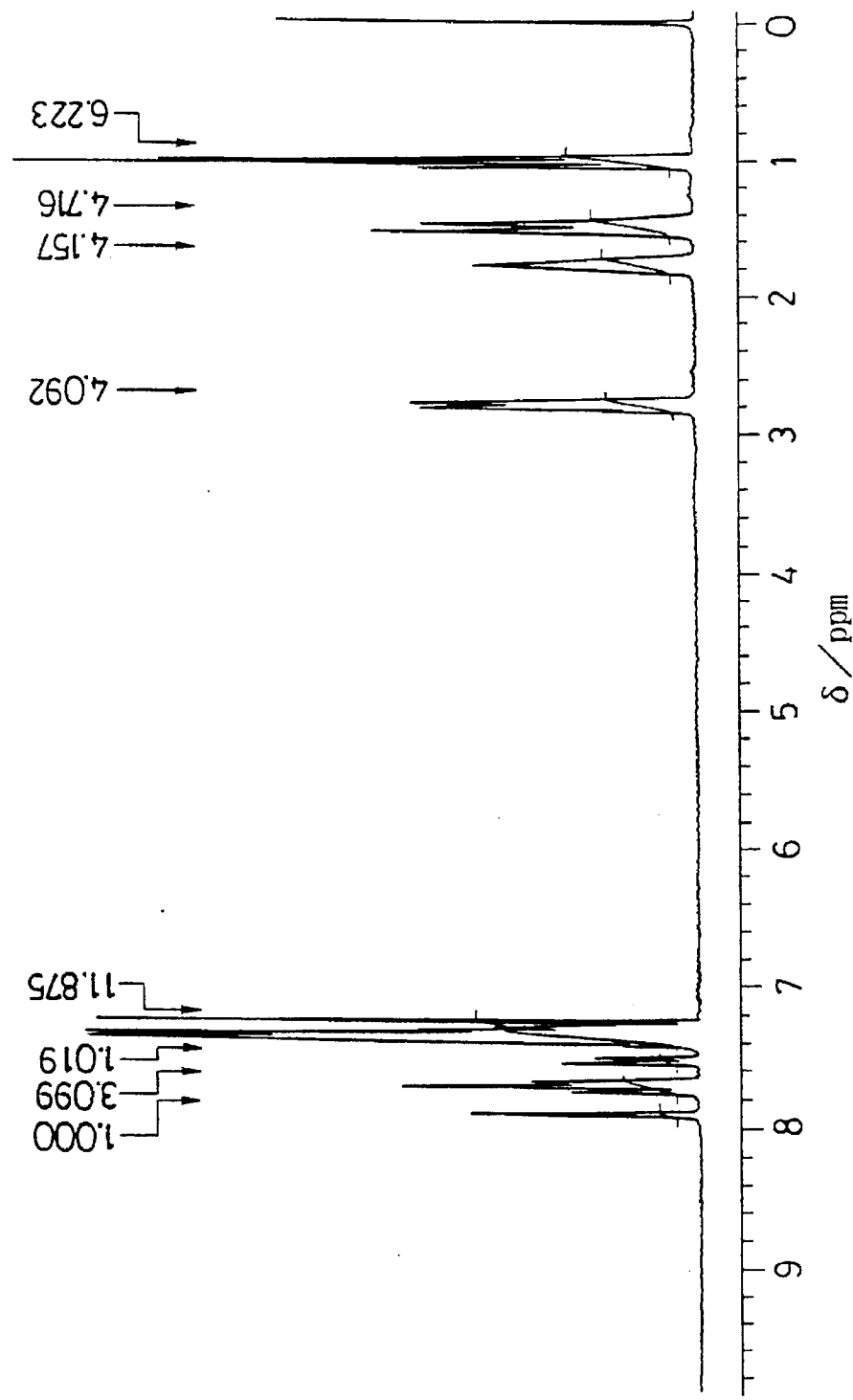

It was synthesized as in Example 1.
Mass analysis: m/e 883 (M+1)$^+$
IR spectrum: FIG. 30
NMR spectrum: FIG. 31
DSC: mp 342.6° C., Tg 103° C.

On elemental analysis, the found values were well coincident with the calculated values.

Example 18

Synthesis of compound VII-27

Figure 32:
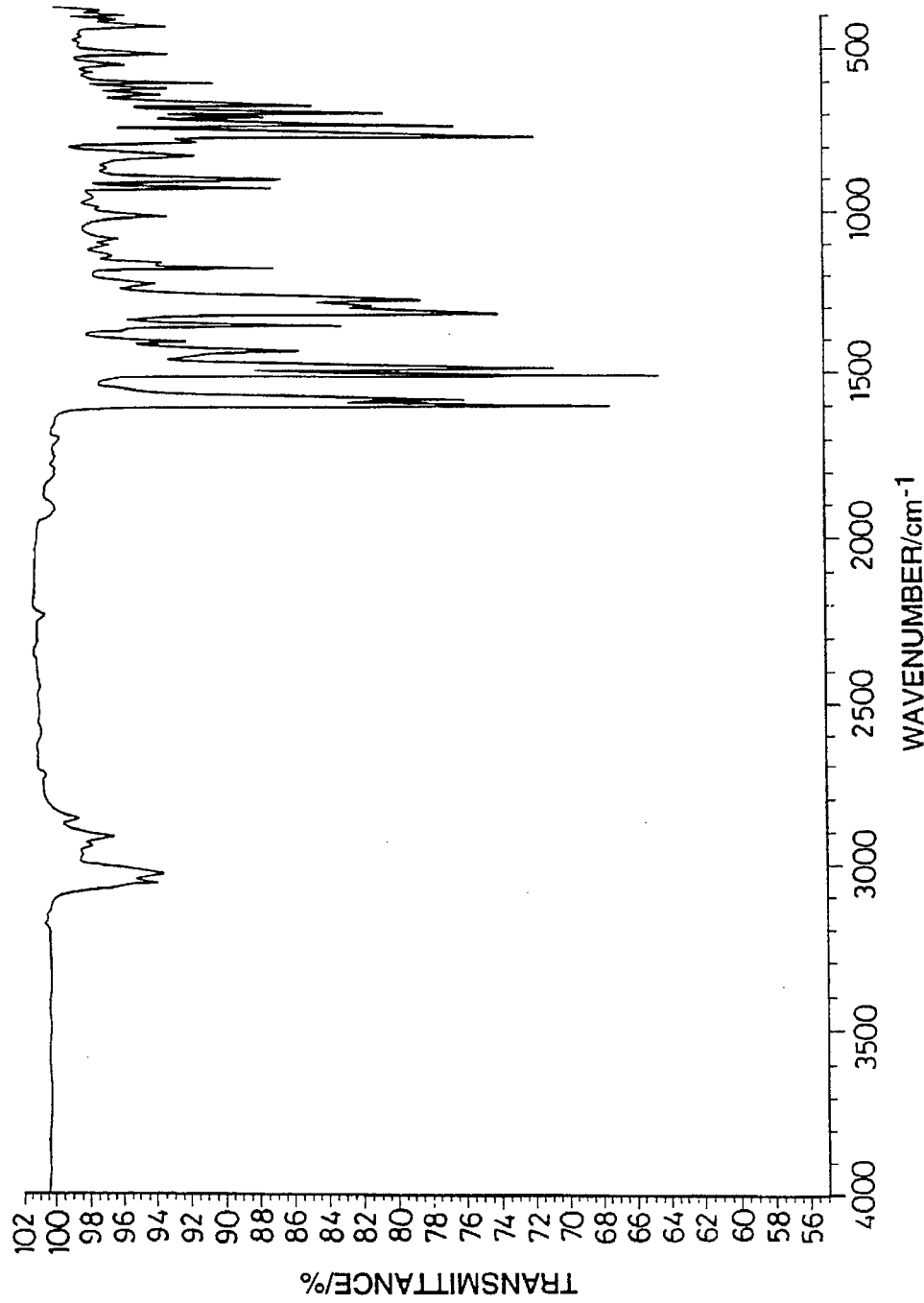
FIGS. 32 and 33 are graphs showing IR and NMR spectra of compound VII-27 in Example 18, respectively.
Figure 33:
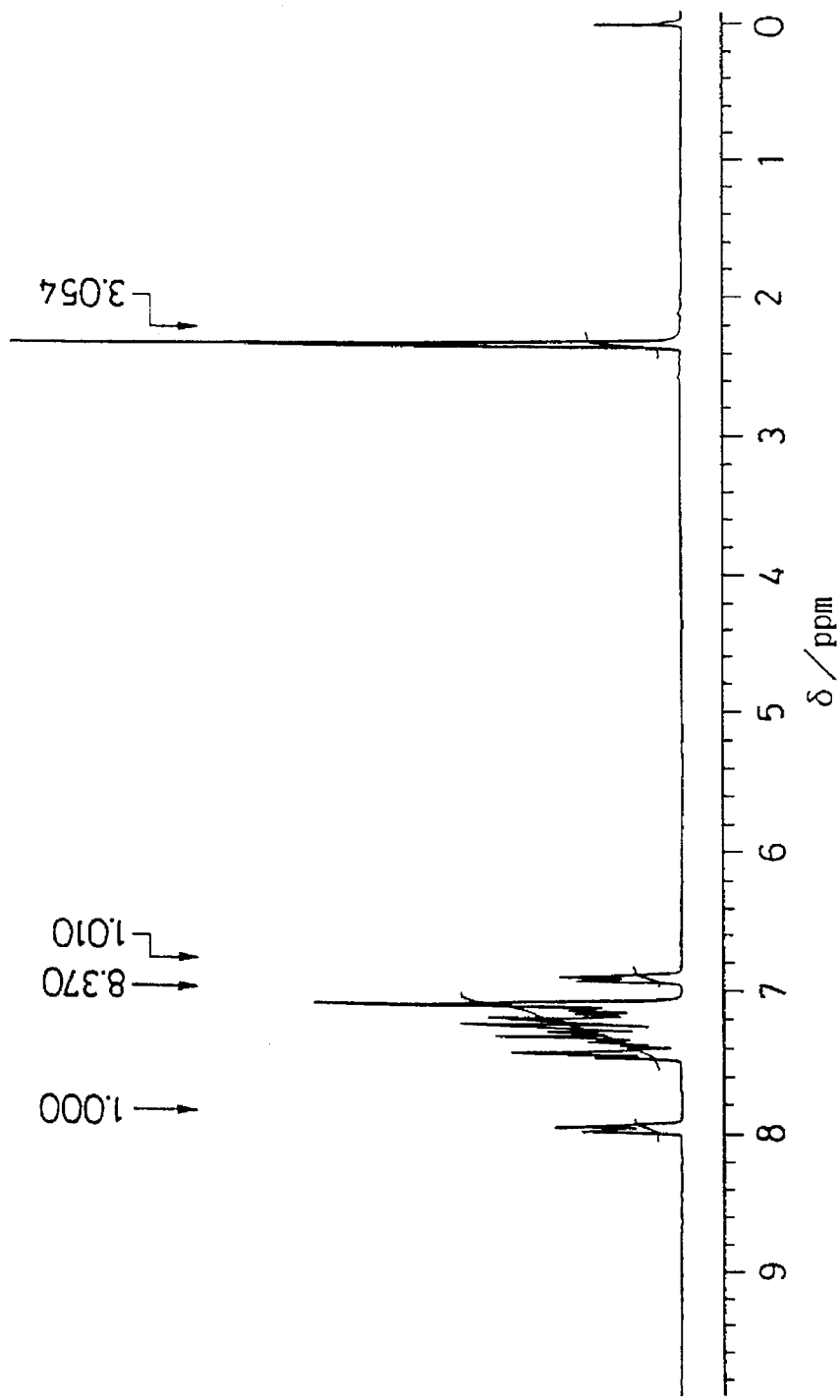

It was synthesized as in Example 5.
Mass analysis: m/e 896 (M$^+$)
IR spectrum: FIG. 32
NMR spectrum: FIG. 33
DSC: mp 361.5° C., Tg 164° C.

On elemental analysis, the found values were well coincident with the calculated values.

Example 19

Synthesis of compound VII-23

Figure 34:
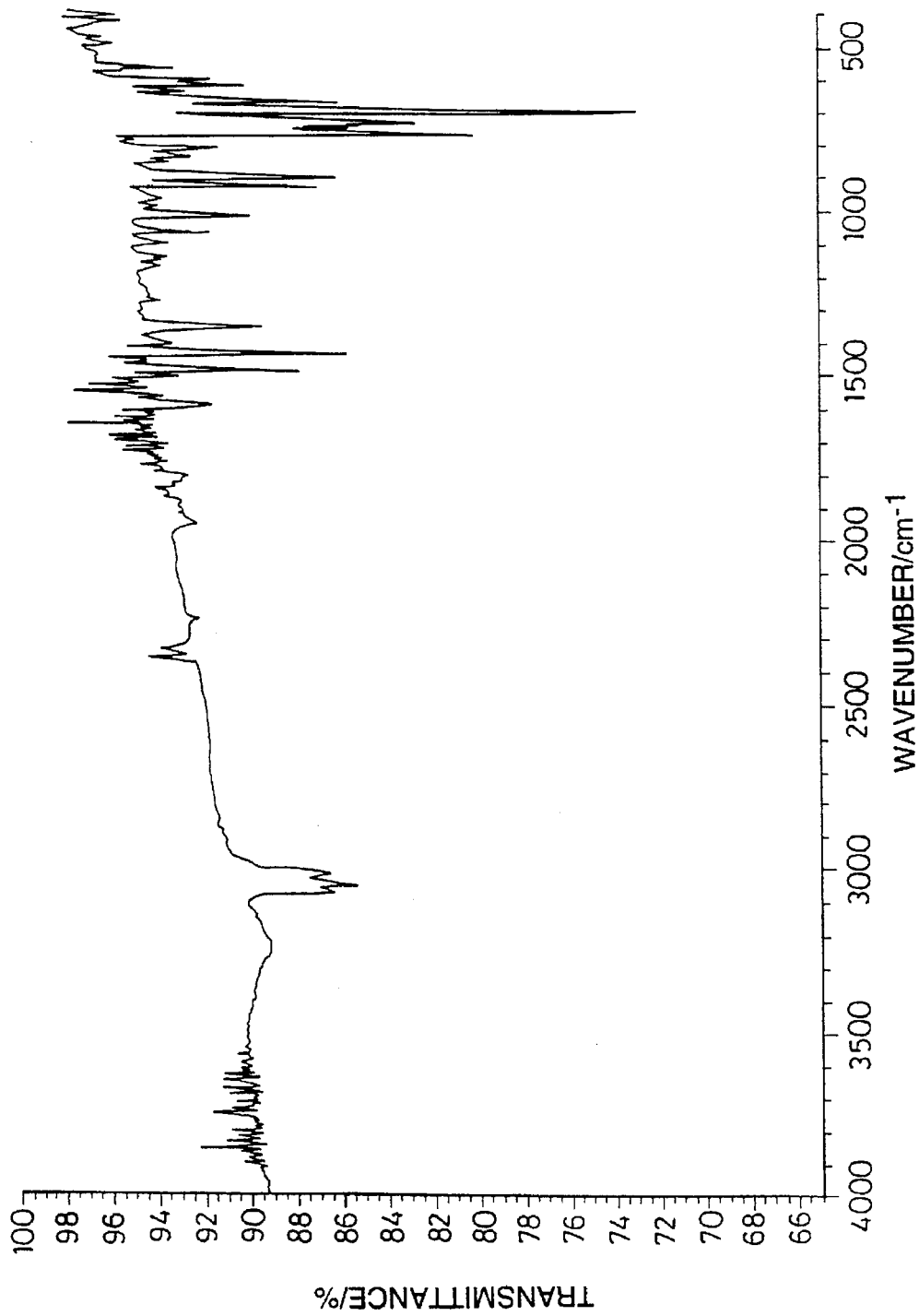
FIGS. 34 and 35 are graphs showing IR and NMR spectra of compound VII-23 in Example 19, respectively.
Figure 35:
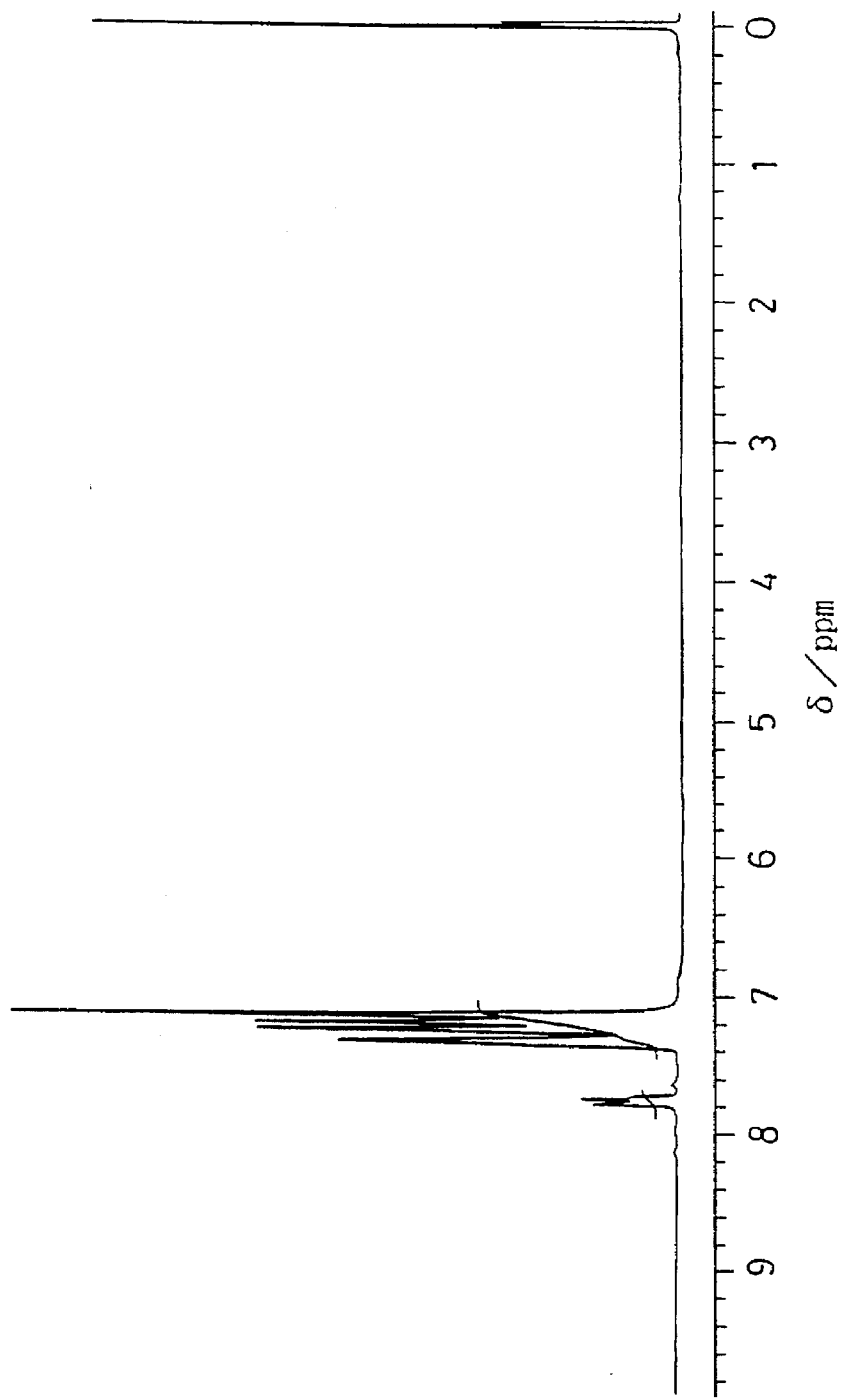

It was synthesized as in Example 5.
IR spectrum: FIG. 34
NMR spectrum: FIG. 35
DSC: mp 423° C., Tg 190° C.

On elemental analysis, the found values were well coincident with the calculated values.

Example 20

Synthesis of compound I-17

Figure 36:
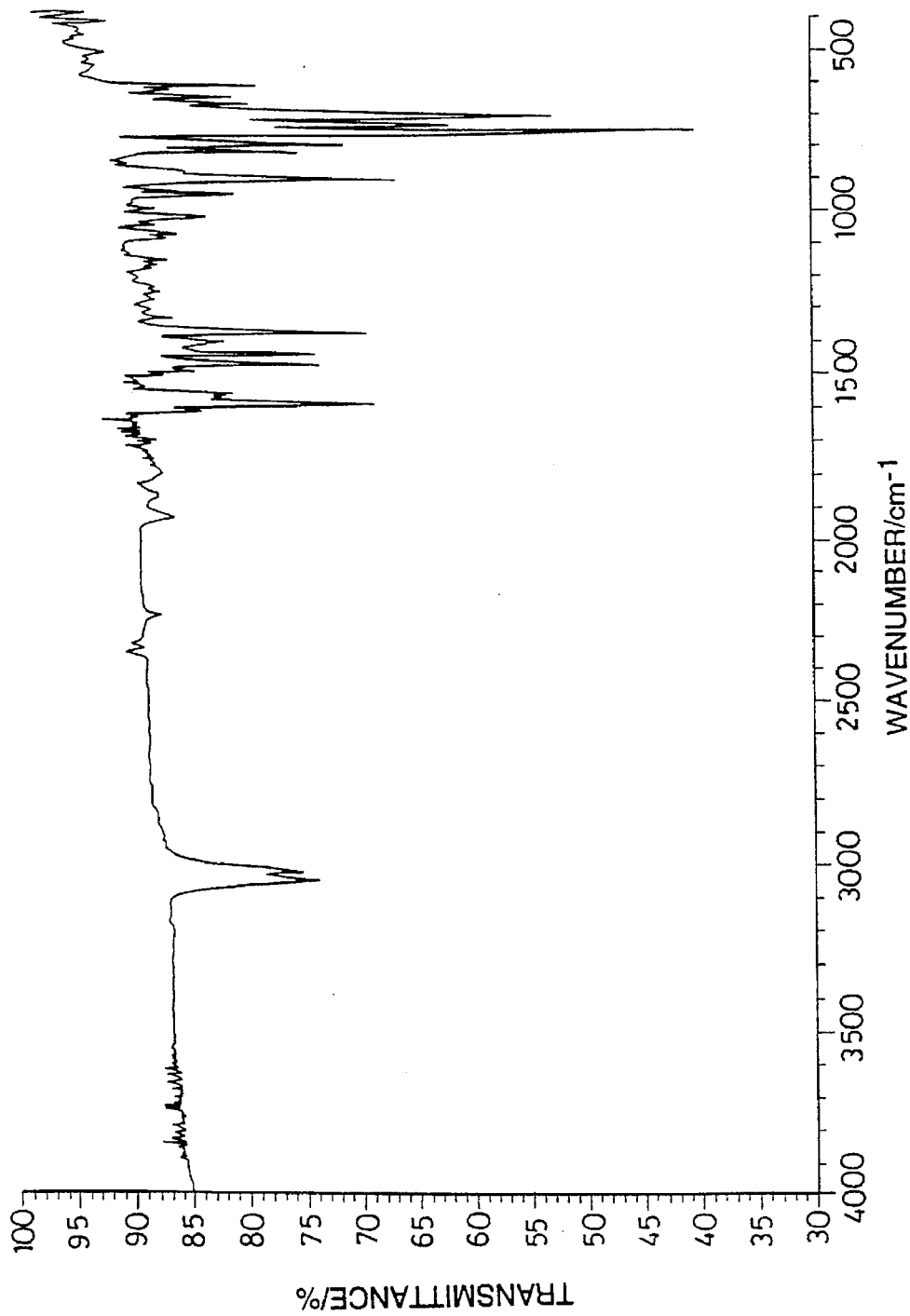
FIGS. 36 and 37 are graphs showing IR and NMR spectra of compound I-17 in Example 20, respectively.
Figure 37:
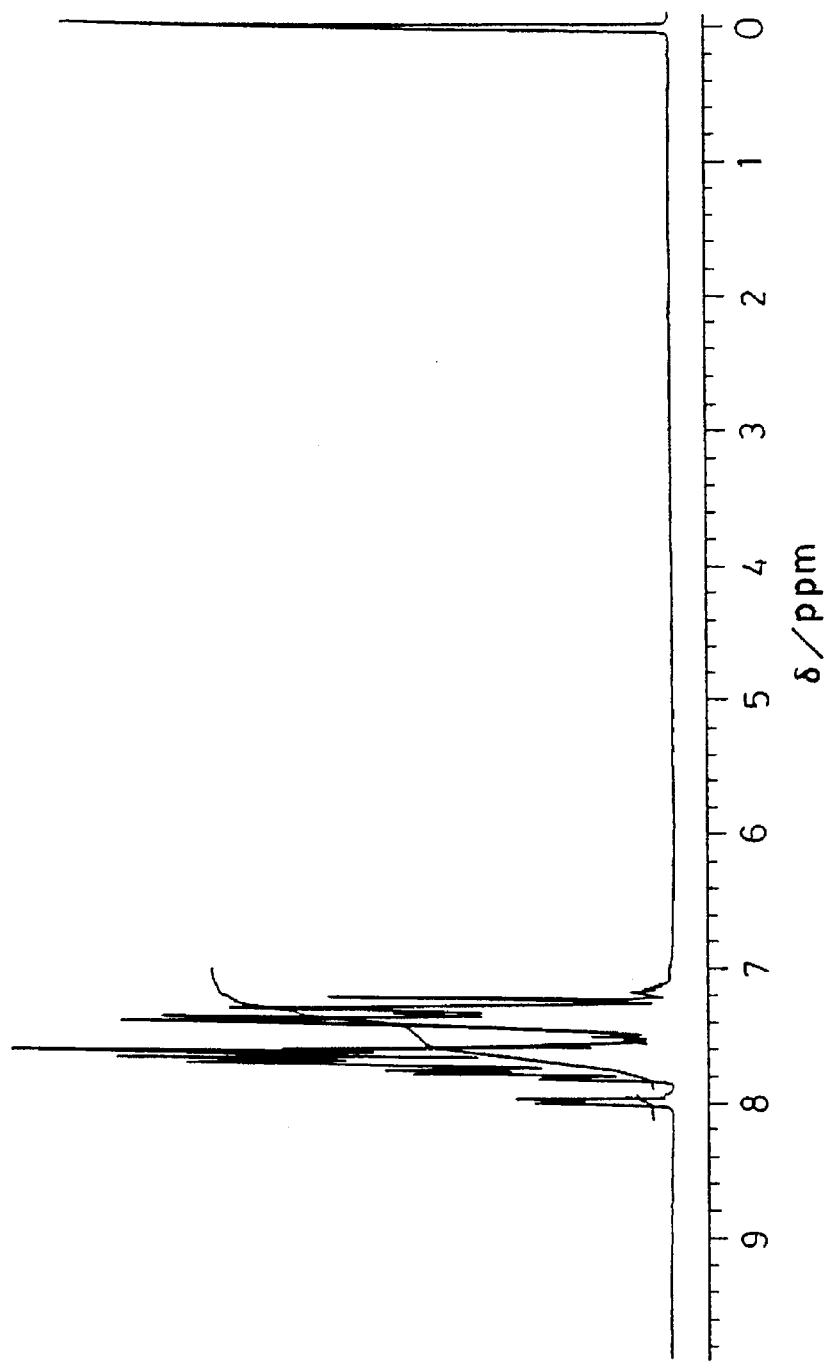

It was synthesized as in Example 1.
IR spectrum: FIG. 36
NMR spectrum: FIG. 37
DSC: Tg 177° C.

On elemental analysis, the found values were well coincident with the calculated values.

Other exemplary compounds represented by formulae (I) to (X) were synthesized in accordance with Examples 1 to 20. These compounds were identified from the results of elemental analysis, IR absorption spectrum, NMR spectrum, and mass analysis.

Example 21

A glass substrate having an ITO transparent electrode (anode) of 100 nm thick was subjected to ultrasonic cleaning with neutral detergent, acetone, and ethanol, pulled up from boiling ethanol, and dried. The substrate was secured by a holder in an evaporation chamber, which was evacuated to a vacuum of 1×10$^{-6}$ Torr.

Then N,N'-diphenyl-N,N'-m-tolyl-4,4'-diamino-1,1'-biphenyl (designated TPD-1) was evaporated at a deposition rate of 0.2 nm/sec. to a thickness of 50 nm, forming a hole injecting and transporting layer.

Then compound I-1 of Example 1 was evaporated at a deposition rate of 0.2 nm/sec. to a thickness of 50 nm, forming a light emitting layer.

With the vacuum kept, tris(8-quinolinolato)aluminum was evaporated at a deposition rate of 0.2 nm/sec. to a thickness of 10 nm, forming an electron injecting and transporting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 15 V and a current density of 217 mA/cm$^2$, emission of blue light (maximum wavelength λmax=485 nm) at a luminance of 4,500 cd/m$^2$ was observed. This light emission continued and remained stable over 500 hours in a dry nitrogen atmosphere without development or growth of local dark spots. The half life of luminance was 100 hours when the element was driven with a constant current of 10 mA/cm$^2$.

Example 22

A glass substrate having an ITO transparent electrode (anode) of 100 nm thick was subjected to ultrasonic cleaning with neutral detergent, acetone, and ethanol, pulled up from boiling ethanol, and dried. The substrate was secured by a holder in an evaporation chamber, which was evacuated to a vacuum of 1×10$^{-6}$ Tort.

Then poly(thiophene-2,5-diyl) was evaporated to a thickness of 10 nm, forming a hole injecting layer.

Then N,N'-diphenyl-N,N'-m-tolyl-4,4'-diamino-1,1'-biphenyl (TPD-1) was evaporated at a deposition rate of 0.2 nm/sec. to a thickness of 50 nm, forming a hole transporting layer.

Then compound I-1 of Example 1 was evaporated to a thickness of 50 nm to form a light emitting layer.

With the vacuum kept, tris(8-quinolinolato)aluminum was evaporated at a deposition rate of 0.2 nm/sec. to a thickness of 10 nm, forming an electron injecting and transporting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 12 V and a current density of 625 mA/cm$^2$, emission of blue light (maximum wavelength λmax=485 nm) at a luminance of 10,000 cd/m$^2$ was observed. This light emission continued and remained stable over 1,000 hours in a dry nitrogen atmosphere without development or growth of local dark spots. The half life of luminance was 400 hours when the element was driven with a constant current of 10 mA/cm$^2$.

Example 23

An EL element was fabricated by the same procedure as in Example 22 except that the electron injecting and transporting layer was omitted.

Electric current was conducted across the EL element with voltage applied. With a voltage of 12 V and a current density of 825 mA/cm$^2$, emission of blue light (maximum wavelength λmax=485 nm) at a luminance of 2,260 cd/m$^2$ was observed. This light emission continued and remained stable over 500 hours in a dry nitrogen atmosphere without development or growth of local dark spots. The half life of luminance was 100 hours when the element was driven with a constant current of 10 mA/cm$^2$.

Example 24

An EL element was fabricated by the same procedure as in Example 22 except that the hole transporting material TPD-1 was replaced by N,N,N',N'-tetrakis(3-biphenyl)-4,4'-diamino-1,1'-biphenyl (designated TPD-2).

Electric current was conducted across the EL element with voltage applied. With a voltage of 12 V and a current density of 675 mA/cm$^2$, emission of blue light (maximum wavelength λmax=485 nm) at a luminance of 5,500 cd/m$^2$ was observed. This light emission continued and remained stable over 1,000 hours in a dry nitrogen atmosphere without development or growth of local dark spots. The half life of luminance was 600 hours when the element was driven with a constant current of 10 mA/cm$^2$.

Example 25

A hole transporting layer was formed as in Example 24 before a light emitting layer was formed by co-evaporating TPD-2 and compound I-1 of Example 1 in a weight ratio of 1:1 at a deposition rate of 0.2 nm/sec. to a thickness of 20 nm.

With the vacuum kept, compound I-1 of Example 1 was evaporated to a thickness of 50 nm, forming an electron transporting layer.

With the vacuum kept, tris(8-quinolinolato)aluminum was evaporated at a deposition rate of 0.2 nm/sec. to a thickness of 10 nm, forming an electron injecting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 12 V and a current density of 540 mA/cm$^2$, emission of blue light (maximum wavelength λmax=480 nm) at a luminance of 12,000 cd/m$^2$ was observed. This light emission continued and remained stable over 5,000 hours in a dry nitrogen atmosphere without development or growth of local dark spots and current leakage. The half life of luminance was 1,500 hours when the element was driven with a constant current of 10 mA/cm$^2$.

Example 26

A glass substrate having an ITO transparent electrode (anode) of 100 nm thick was subjected to ultrasonic cleaning with neutral detergent, acetone, and ethanol, pulled up from boiling ethanol, and dried. The substrate was secured by a holder in an evaporation chamber, which was evacuated to a vacuum of 1×10$^{-6}$ Torr.

Then poly(thiophene-2,5-diyl) was evaporated to a thickness of 10 nm, forming a hole injecting layer.

Then N,N'-diphenyl-N,N'-m-tolyl-4,4'-diamino-1,1'-biphenyl (TPD-1) was evaporated at a deposition rate of 0.2 nm/sec. to a thickness of 50 nm, forming a hole transporting layer.

Then compound II-1 of Example 2 was evaporated to a thickness of 50 nm to form a light emitting layer.

With the vacuum kept, tris(8-quinolinolato)aiuminum was evaporated at a deposition rate of 0.2 nm/sec. to a thickness of 10 nm, forming an electron injecting and transporting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 12 V and a current density of 625 mA/cm$^2$, emission of blue-green light (maximum wavelength λmax=495 nm) at a luminance of 12,000 cd/m$^2$ was observed. This light emission continued and remained stable over 1,000 hours in a dry nitrogen atmosphere without development or growth of local dark spots. The half life of luminance was 100 hours when the element was driven with a constant current of 10 mA/cm$^2$.

Example 27

An EL element was fabricated by the same procedure as in Example 21 except that compound VII-2 of Example 5 was used instead of compound I-1.

Electric current was conducted across the EL element with voltage applied. With a voltage of 14 V and a current density of 450 mA/cm$^2$, emission of blue light (maximum wavelength λmax=460 nm) at a luminance of 1,921 cd/m$^2$ was observed. This light emission continued and remained stable over 1,000 hours in a dry nitrogen atmosphere without development or growth of local dark spots. The half life of luminance was 300 hours when the element was driven with a constant current of 10 mA/cm$^2$.

Example 28

An EL element was fabricated by the same procedure as in Example 22 except that after formation of the light emitting layer, tris(8-quinolinolato)aluminum was evaporated at a deposition rate of 0.2 nm/sec. to a thickness of 20 nm to form an electron transporting layer and thereafter, tetrabutyldiphenoquinone was evaporated to a thickness of 10 nm to form an electron injecting layer.

Electric current was conducted across the EL element with voltage applied. With a voltage of 12 V and a current density of 625 mA/cm$^2$, emission of blue light (maximum wavelength λmax=485 nm) at a luminance of 10,000 cd/m$^2$ was observed. This light emission continued and remained stable over 1,000 hours in a dry nitrogen atmosphere without development or growth of local dark spots. The half life of luminance was 80 hours when the element was driven with a constant current of 10 mA/cm$^2$.

Example 29

A glass substrate having an ITO transparent electrode (anode) of 100 nm thick was subjected to ultrasonic cleaning with neutral detergent, acetone, and ethanol, pulled up from boiling ethanol, and dried. The substrate was secured by a holder in an evaporation chamber, which was evacuated to a vacuum of 1×10$^{-6}$ Torr.

Then poly(thiophene-2,5-diyl) was evaporated to a thickness of 10 nm, forming a hole injecting layer.

Then N,N'-diphenyl-N,N'-m-tolyl-4,4'-diamino-1,1'-biphenyl (TPD-1) was evaporated at a deposition rate of 0.2 nm/sec. to a thickness of 50 nm, forming a hole transporting layer.

Then tetraphenylcyclopentadiene was evaporated to a thickness of 50 nm to form a light emitting layer.

With the vacuum kept, compound I-1 of Example 1 was evaporated at a deposition rate of 0.2 nm/sec. to a thickness of 10 nm, forming an electron injecting and transporting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 12 V and a current density of 100 mA/cm$^2$, emission of blue light (maximum wavelength λmax=460 nm) at a luminance of 800 cd/m$^2$ was observed. This light emission continued and remained stable over 100 hours in a dry nitrogen atmosphere without development or growth of local dark spots. The half life of luminance was 10 hours when the element was driven with a constant current of 10 mA/cm$^2$.

Additional organic EL elements were fabricated in accordance with Examples 21 to 29 by appropriately selecting one or more compounds from the inventive compounds of formulae (I) to (X) and using them as the light emitting layer or the electron injecting and transporting layer in appropriate combinations other than the above-mentioned combinations. Equivalent results were obtained in accordance with the layer structure of the respective EL elements.

Comparative Example 1

A glass substrate having an ITO transparent electrode (anode) of 100 nm thick was subjected to ultrasonic cleaning with neutral detergent, acetone, and ethanol, pulled up from boiling ethanol, and dried. The substrate was secured by a holder in an evaporation chamber, which was evacuated to a vacuum of 1×10$^{-6}$ Torr.

Then N,N'-diphenyl-N,N'-m-tolyl-4,4'-diamino-1,1'-biphenyl (TPD-1) was evaporated to a thickness of 50 nm, forming a hole injecting and transporting layer.

With the vacuum kept, 1,3-bis(5-(4-t-butylphenyl)-1,3,4-oxadiazo-2-yl)benzene (designated OXD-7) was evaporated at a deposition rate of 0.2 nm/sec. to a thickness of 50 nm, forming a light emitting layer.

With the vacuum kept, tris(8-quinolinolato)aluminum was evaporated at a deposition rate of 0.2 nm/sec. to a thickness of 10 nm, forming an electron injecting and transporting layer.

With the vacuum kept, MgAg (weight ratio 10:1) was evaporated at a deposition rate of 0.2 nm/sec. to a thickness of 200 nm to form a cathode, obtaining an EL element.

Electric current was conducted across the EL element with voltage applied. With a voltage of 14 V and a current density of 127 mA/cm$^2$, emission of blue light (maximum wavelength λmax=480 nm) at a luminance of 550 cd/m$^2$ was observed. When this light emission continued in a dry nitrogen atmosphere, development and growth of local dark spots was observed at 10 hours of operation and dielectric breakdown occurred at 20 hours of operation. The half life of luminance was 20 minutes on driving with a constant current of 10 mA/cm$^2$.

Comparative Example 2

An organic EL element was fabricated in accordance with C. Adachi et al., Applied Phys. Lett., 56, 799 (1990) using 9,10-diphenylanthracene described therein as a light emitting layer. More specifically, in Comparative Example 1, the electron injecting and transporting layer was omitted and instead, 9,10-diphenylanthracene was evaporated to a thickness of 50 nm to form a light emitting layer also serving as an electron injecting and transporting layer.

In this EL element, the organic compound layer was crystalline. When voltage was applied in an electrically short-circuit condition, emission of blue light was observed, but dielectric breakdown occurred shortly.

There have been described phenylanthracene derivatives which are effective for forming good thin films in a less crystalline or amorphous state. They can be used as compounds for organic EL elements, especially as blue light emitting material and electron injecting and transporting material.

In fact, organic EL elements using phenylanthracene derivatives according to the present invention are free of current leakage and eliminate development and growth of dark spots. These, combined with restrained crystallization in the film of phenylanthracene derivative, result in a reliable element capable of continuous light emission. Particularly when used in the light emitting layer, the phenylanthracene derivatives ensure emission of blue light at a high luminance of 10,000 cd/m² or more.

Japanese Patent Application No. 110569/1994 are incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. An organic electroluminescent element comprising at least one organic compound layer, said layer comprising a phenylanthracene derivative of formula (1):

$$A_1\text{—}L\text{—}A_2 \qquad (1)$$

wherein each of $A_1$ and $A_2$, which may be identical or different, is a monophenylanthryl or diphenylanthryl group, and L is a valence bond or a divalent linkage group.

2. The organic electroluminescent element of claim 1 wherein said organic compound layer containing the phenylanthracene derivative is a light emitting layer.

3. The organic electroluminescent element of claim 2 further comprising at least one hole injecting layer, at least one hole transporting layer, and at least one electron injecting and transporting layer.

4. The organic electroluminescent element of claim 2 further comprising at least one hole injecting layer, at least one hole transporting layer, at least one electron transporting layer, and at least one electron injecting layer.

5. The organic electroluminescent element of claim 1 wherein said organic compound layer containing the phenylanthracene derivative is an electron injecting and transporting layer and said element further includes a light emitting layer.

6. The organic electroluminescent element of claim 1 comprising at least one light emitting layer which is a mix layer of an electron injecting and transporting compound and a hole injecting and transporting compound, said mix layer containing the phenylanthracene derivative.

7. The electroluminescent element of claim 1, wherein the phenylanthracene derivative is of the following formula (2):

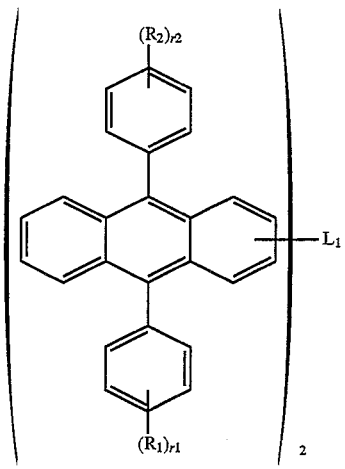

wherein each of $R_1$ and $R_2$, which may be identical or different, is selected from the group consisting of an alkyl, cycloalkyl, aryl, alkenyl, alkoxy, aryloxy, amino and heterocyclic group, each of r1 and r2 is 0 or an integer of 1 to 5, wherein when $r_1$ is an integer of at least 2, the $R_1$ groups may be identical or different or the $R_1$ groups, taken together, may form a ring, and wherein when $r_2$ is an integer of at least 2, the $R_2$ groups may be identical or different or the $R_2$ groups, taken together, may form a ring, and $L_1$ is a valence bond or an arylene group which may have an intervening group in the form of an alkylene group, —O—, —S— or —NR— wherein R is an alkyl or aryl group.

8. The electroluminescent element of claim 1, wherein the phenylanthracene derivative is of the following formula (3):

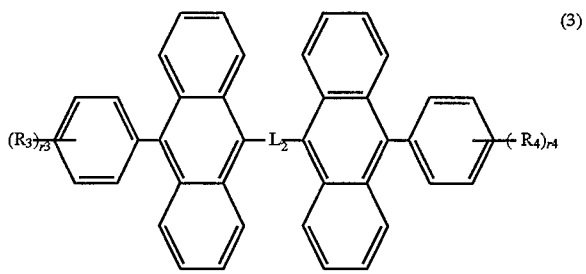

wherein each of $R_3$ and $R_4$, which may be identical or different, is selected from the group consisting of an alkyl, cycloalkyl, aryl, alkenyl, alkoxy, aryloxy, amino and heterocyclic group, each of r3 and r4 is 0 or an integer of 1 to 5, wherein when $r_3$ is an integer of at least 2, the $R_3$ groups may be identical or different or the $R_3$ groups, taken together, may form a ring, and wherein when $r_4$ is an integer of at least 2, the $R_4$ groups may be identical or different or the $R_4$ groups, taken together, may form a ring, and $L_2$ is a valence bond or an arylene group which may have an intervening group in the form of an alkylene group, —O—, —S— or —NR— wherein R is an alkyl or aryl group.

9. A phenylanthracene derivative which is of the following formula (2):

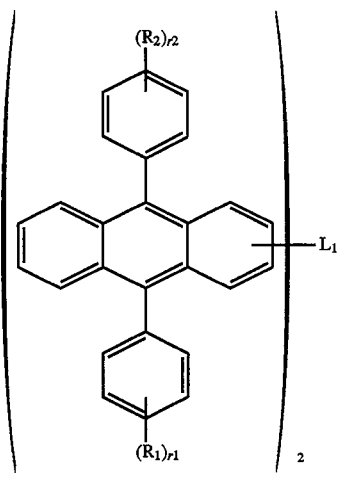

(2)

wherein each of $R_1$ and $R_2$, which may be identical or different, is selected from the group consisting of an alkyl, cycloalkyl, aryl, alkenyl, alkoxy, aryloxy, amino and heterocyclic group, each of $r_1$ and $r_2$ is 0 or an integer of 1 to 5, wherein when $r_1$ is an integer of at least 2, the $R_1$ groups may be identical or different or the $R_1$ groups, taken together, may form a ring, and wherein when $r_2$ is an integer of at least 2, the $R_2$ groups may be identical or different or the $R_2$ groups, taken together, may form a ring, and $L_1$ is a valence bond or an arylene group which may have an intervening group in the form of an alkylene group, —O—, —S—, or —NR— wherein R is an alkyl or aryl group.

10. A phenylanthracene derivative which is of the following formula (3):

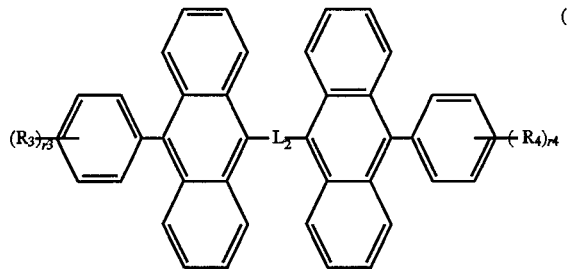

(3)

wherein each of $R_3$ and $R_4$, which may be identical or different, is selected from the group consisting of an alkyl, cycloalkyl, aryl, alkenyl, alkoxy, aryloxy, amino and heterocyclic group, each of r3 and r4 is 0 or an integer of 1 to 5, r3+r4 being at least 1, and wherein when r3 is an integer of at least 2, the $R_3$ groups may be identical or different or the $R_3$ groups taken together, may form a ring, and wherein when $r_4$ is an integer of at least 2, the $R_4$ groups may be identical or different or the $R_4$ groups, taken together, may form a ring, and $L_2$ is a valence bond or an arylene group which may have an intervening group in the form of an alkylene group, —O—, —S—, or —NR— wherein R is an alkyl or aryl group.

11. A phenylanthracene derivative which is of the following formula (3):

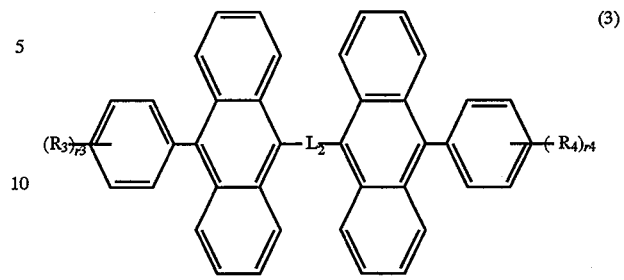

(3)

wherein each of $R_3$ and $R_4$, which may be identical or different, is selected from the group consisting of an alkyl, cycloalkyl, aryl, alkenyl, alkoxy, aryloxy, amino and heterocyclic group, each of $r_3$ and $r_4$ is 0 or an integer of 1 to 5, wherein when $r_3$ is an integer of at least 2, the $R_3$ groups may be identical or different or the $R_3$ groups, taken together, may form a ring, and wherein when $r_4$ is an integer of at least 2, the $R_4$ groups may be identical or different or the $R_4$ groups, taken together, may form a ring, and $L_2$ is or an arylene group which may have an intervening group in the form of an alkylene group, —O—, —S—, or —NR— wherein R is an alkyl or aryl group.

12. A phenylanthracene derivative which is of the following formula (3):

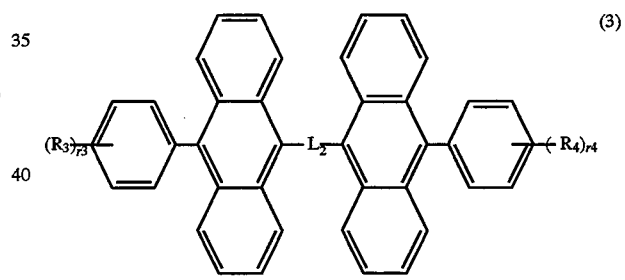

(3)

wherein each of $R_3$ and $R_4$, which may be identical or different, is selected from the group consisting of an alkyl, cycloalkyl, aryl, alkenyl, alkoxy, aryloxy, amino and heterocyclic group, each of $r_3$ and r4 is an integer of 1 to 5, wherein when $r_3$ is an integer of at least 2, the $R_3$ groups, may be identical or different or the $R_3$ groups, taken together, may form a ring, and wherein when $r_4$ is an integer of at least 2, the $R_4$ groups, may be identical or different or the $R_4$ groups, taken together, may form a ring, and $L_2$ is a valence bond or an arylene group which may have an intervening group in the form of an alkylene group, —O—, —S—, or —NR— wherein R is an alkyl or aryl group.

* * * * *